United States Patent
Long et al.

(10) Patent No.: US 10,745,405 B2
(45) Date of Patent: Aug. 18, 2020

(54) GLUCURONIDE PRODRUGS OF JANUS KINASE INHIBITORS

(71) Applicant: THERAVANCE BIOPHARMA R&D IP, LLC, South San Francisco, CA (US)

(72) Inventors: Daniel D. Long, San Francisco, CA (US); Donna A. A. Wilton, San Francisco, CA (US); Mandy M. Loo, San Jose, CA (US); Ryan Hudson, San Jose, CA (US); Patrick J. Brassil, Redwood City, CA (US)

(73) Assignee: Theravance Biopharma R&D IP, LLC, South San Francisco, CA (US)

( * ) Notice: Subject to any disclaimer, the term of this patent is extended or adjusted under 35 U.S.C. 154(b) by 0 days.

(21) Appl. No.: 15/986,028

(22) Filed: May 22, 2018

(65) Prior Publication Data

US 2018/0339990 A1 Nov. 29, 2018

Related U.S. Application Data

(60) Provisional application No. 62/509,847, filed on May 23, 2017.

(51) Int. Cl.
| | |
|---|---|
| *C07D 487/04* | (2006.01) |
| *A61P 29/00* | (2006.01) |
| *C07H 17/02* | (2006.01) |
| *C07H 15/26* | (2006.01) |
| *C07H 1/00* | (2006.01) |
| *C07H 13/12* | (2006.01) |

(52) U.S. Cl.
CPC .......... *C07D 487/04* (2013.01); *A61P 29/00* (2018.01); *C07H 1/00* (2013.01); *C07H 13/12* (2013.01); *C07H 15/26* (2013.01); *C07H 17/02* (2013.01)

(58) Field of Classification Search
CPC .................................................. C07D 487/04
See application file for complete search history.

(56) References Cited

U.S. PATENT DOCUMENTS

| | | | |
|---|---|---|---|
| 5,811,388 | A | 9/1998 | Friend et al. |
| 7,598,257 | B2 | 10/2009 | Rodgers et al. |
| RE41,783 | E | 9/2010 | Blumenkopf et al. |
| 8,133,899 | B2 | 3/2012 | Mitton-Fry et al. |
| 8,158,616 | B2 | 4/2012 | Rodgers et al. |
| 2011/0086810 | A1 | 4/2011 | Rodgers et al. |
| 2011/0152207 | A1 | 6/2011 | Goff et al. |
| 2012/0289571 | A1 | 11/2012 | Zhao et al. |
| 2014/0357557 | A1 | 12/2014 | Cole et al. |
| 2017/0145044 | A1 | 5/2017 | Hudson et al. |

FOREIGN PATENT DOCUMENTS

| | | |
|---|---|---|
| CN | 106496233 A | 3/2017 |
| WO | 93/22334 A1 | 11/1993 |
| WO | 2011097087 A1 | 8/2011 |

OTHER PUBLICATIONS

Danese, Silvio. Am. J. Physiol Gastrointest Liver Physiol 310, 2016.*
U.S. Appl. No. 15/914,189, unpublished, Long et al.
U.S. Appl. No. 15/986,018, unpublished Long.
Amidon et al., "Colon-targeted oral drug delivery systems: Design trends and approaches", AAPS PharmSciTech, 16 (4): 731-741 (2015).
Azad Khan et al., "Tissue and bacterial splitting of sulphasalazine", Clinical Science, 64: 349-354 (1983).
Bouvier et al., "First enzymatically activated Taxotere prodrugs designed for ADEPT and PMT", Bioorganic & Medicinal Chemistry, 12: 969-977 (2004).
Bunnelle, "Reagents for stereoselective preparation of N-carbamyl beta-D-glucuronides", The Journal of Organic Chemistry, 76: 5429-5432 (2011).
Burke et al., "Development of novel quaternary ammonium linkers for antibody-drug conjugates", Molecular Cancer Therapeutics, 15(5): 938-945 (May 2016).
Chourasia et al., "Pharmaceutical approaches to colon targeted drug delivery systems", J Pharm Pharmaceut Sci, 6 (1): 33-66 (2003).
Clark et al., "Discovery and development of Janus Kinase (JAK) inhibitors for inflammatory diseases", Journal of Medicinal Chemistry, 57: 5023-5038 (2014).
Danese, "New therapies for inflammatory bowel disease: from the bench to the bedside", Gut, 61: 918-932 (2012).
Friend et al., "A colon-specific drug-delivery system based on drug glycosides and the glycosidases of colonic bacteria", J Med Chem, 27: 261-266 (1984).
Friend et al., "Drug glycosides: Potential prodrugs for colon-specific drug delivery", J Med Chem, 28: 51-57 (1985).

(Continued)

*Primary Examiner* — Emily A Berhardt
*Assistant Examiner* — Laura M Daniel
(74) *Attorney, Agent, or Firm* — Jeffrey A. Hagenah; Florence Jovic

(57) ABSTRACT

The invention relates to glucuronide prodrug compounds of Janus kinase (JAK) inhibitors having formula I:

where $W^1$, $R^1$ and $A^1$ are as defined. The invention also relates to pharmaceutical compositions comprising such compounds; methods of using such compounds to treat gastrointestinal inflammatory diseases; and processes and intermediates for preparing such compounds.

31 Claims, No Drawings

(56) References Cited

OTHER PUBLICATIONS

Friend, "Glycosides in colonic drug delivery", Oral colon-specific drug delivery, pp. 153-187 (1992).
Goff et al., "Targeted delivery of vitamin D to the colon using beta-glucuronides of vitamin D: therapeutic effects in a murine model of inflammatory bowel disease", Am J Physiol Gastrointest Liver Physiol, 302: G460-G469 (2012).
Jeffrey et al., "Expanded utility of the beta-glucuronide linker: ADCs that deliver phenolic cytotoxic agents", ACS Medicinal Chemisty Letters, 1: 277-280 (2010).
Kagan et al., "Systems for region selective drug delivery in the gastrointestinal tract: biopharmaceutical considerations", Expert Opin Drug Deliv, 5(6): 681-692 (2008).
Kolakowski et al., "The methylene alkoxy carbamate self-immolative unit: utilization for the targeted delivery of alcohol-containing payloads with antibody-drug conjugates", Angew Chem Int Ed, 55: 1-5 (2016).
Kolakowski et al., "The methylene alkoxy carbamate self-immolative unit: utilization for the targeted delivery of alcohol-containing payloads with antibody-drug conjugates", Angew Chem Int Ed, 55: 1-5 Supporting Information (2016).
Lam et al., "Vedolizumab for ulcerative colitis and Crohn's disease: results and implications of GEMINI studies", Immunotherapy, 6(9): 963-971 (2014).
Lougerstay-Madec et al., "Synthesis of self-immolative glucuronide-based prodrugs of a phenol mustard", Anti-Cancer Drug Design, 13: 995-1007 (1998).
Mozaffari et al., "New biologic therapeutics for ulcerative colitis and Crohn's disease", Expert Opin Biol Ther, 14(5): 583-600 (2014).
Panes et al., "Randomized trial of tofacitinib in active ulcerative colitis: analysis of efficacy based on patient-reported outcomes", BMC Gastroenterology, 15: 14-23 (2015).
Philip et al., "Colon targeted drug delivery systems: A review on primary and novel approaches", Oman Medical Journal, 25(2): 70-78 (2010).
Ruxolitinib, Prescribing Information, (2016).
Sandborn et al., "Tofacitinib, an oral janus kinase inhibitor, in active ulcerative colitis", The New England Journal of Medicine, pp. 616-624 (2012).
Scheline, "Drug metabolism by intestinal microorganisms", Journal of Pharmaceutical Sciences, 57(12): 2021-2037 (1968).
Schmidt et al., "Glucuronide prodrugs of hydoxy compounds for antibody directed enzyme prodrug therapy (ADEPT): a phenol nitrogen mustard carbamate", Bioorganic & Medicinal Chemistry Letters, 7(8): 1071-1076 (1997).
Thomas et al., "Efficient regio- and stereoselective synthesis of 1-beta-O-glucuronyl carbamates and carbonates from unprotected 1,2,3,4-Hydroxyl glucuronates", Synlett, 12: 1966-1968 (2007).

Tranoy-Opalinski et al., "Beta-glucuronidase-responsive prodrugs for selective cancer chemotherapy: An update", European Journal of Medicinal Chemistry, 74: 302-313 (2014).
Wolk et al., "New targeting strategies in drug therapy of inflammatory bowel disease: mechanistic approaches and opportunities", Expert Opin Drug Deliv, 10(9): 1275-1286 (2013).
Friend, "Colon-specific drug delivery", Advanced Drug Delivery Reviews, 7: 149-199 (1991).
Goracinova et al., "Drug targeting in IBD treatment—Existing and new approaches", Inflammatory Bowel Disease Advances in Pathogenesis and Management, pp. 301-332 (2012).
Nolen et al., "Budesonide-Beta-D-glucuronide: a potential prodrug for treatment of ulcerative colitis", Journal of Pharmaceutical Sciences, 84 (6): 677-681 (Jun. 1995).
Angenault et al., "Cancer chemotherapy: A SN-38 (7-ethyl-10-hydroxycamptothecin)glucuronide prodrug for treatment by a PMT(prodrug montherapy)strategy", Bioorganic & Medicinal Chemistry Letters, 13: 947-950 (2003).
Desbene et al., "Application of the ADEPT strategy to the MDR resistance in cancer chemotherapy", Anti-cancer Drug Design, 14(2): 93-106 (1999).
Desbene et al., "Application of the ADEPT strategy to the MDR resistance in cancer chemotherapy", XP-002780712 (1999).
Goto et al., "Synthesis and biological activity of the metabolites of diethyl 4[(4-bromo-2-cyanophenyl)carbamoyl] benzylphosphonate (NO-1886)", Chem Pharm Bull, 44(3): 547-551 (1996).
Kiss et al., "Synthesis and O.R.D./C.D. spectra of the anomers of 2-amino-5-ethoxyphenyl d-glucopyranosiduronic acid and some derivatives thereof", Carbohydrate Research, 12: 115-129 (1970).
Kreuzer et al., "Aufbau von oligosacchariden mit glycosylfluoriden unter lewissaure-katalyse", Carbohydrate Research, 149: 347-361 (1986).
Papot et al., "Design of selectively activated anticancer prodrugs: Elimination and cyclization strategies", Current Medicinal Chemistry, 2(2):155-185 (2002).
Schmidt et al., "Cancer chemotherapy: A paclitaxel prodrug for ADEPT (Antibody-directed enzyme prodrug therapy)", European Journal of Organic Chemistry, pp. 2129-2134 (2001).
Schmidt et al., "In vitro fluorine-19 nuclear magnetic resonance study of the liberation of antitumor nitrogen mustard from prodrugs", Royal Society of Chemistry, J. Chem. Soc., Perkin Transactions, 1:1302-1308 (2002).
Thomas et al., "Synthesis and biological evaluation of glucuronide prodrugs of the histone deacetylase inhibitor CI-994 application in selective cancer chemotherapy", Bioorganic & Medicinal Chemistry, 16: 8109-8116 (2008).
PCT International Preliminary Report and Written Opinion for PCT/US2018/033818 dated Aug. 9, 2018.

* cited by examiner

GLUCURONIDE PRODRUGS OF JANUS KINASE INHIBITORS

CROSS-REFERENCE TO RELATED APPLICATIONS

This application claims the benefit of U.S. Provisional Application No. 62/509,847, filed on May 23, 2017, the disclosure of which is incorporated herein by reference in its entirety.

BACKGROUND OF THE INVENTION

Field of the Invention

This invention relates to glucuronide prodrug compounds of certain Janus kinase (JAK) inhibitors. The invention also relates to pharmaceutical compositions comprising such compounds; methods of using such compounds to treat gastrointestinal inflammatory diseases; and processes and intermediates for preparing such compounds.

State of the Art

Ruxolitinib, baricitinib and oclacitinib are Janus kinase (JAK) inhibitors having the following chemical structures:

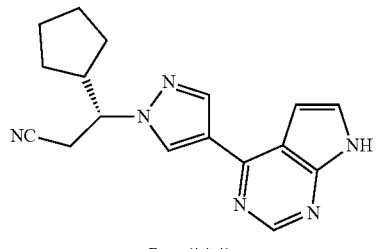
Ruxolitinib

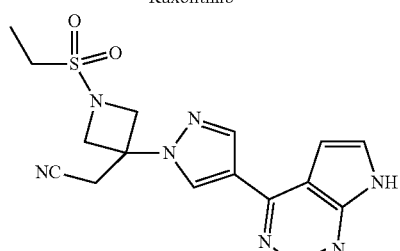
Baricitinib

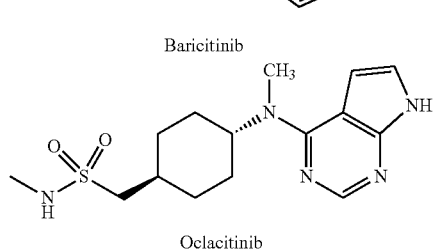
Oclacitinib

Ruxolitinib, baricitinib and oclacitinib are described in, e.g., U.S. Pat. Nos. 7,798,257 B2; 8,158,616 B2; and 8,133,899 B2, respectively, as being useful as immunosuppressive agents for treating various medical conditions and disorders. JAK inhibitors, however, are also known to have a number of systemically-mediated side effects including, e.g., thrombocytopenia, anemia and neutropenia; risk of serious infections; non-melanoma skin cancers; and lipid elevations. See, e.g., JAKAFI® (ruxolitinib) Prescribing Information, Incyte Corporation, Wilmington, Del., Revised 3/2016.

Recently, a JAK inhibitor (i.e., tofacitinib) has been investigated for the treatment of ulcerative colitis (UC), a gastrointestinal inflammatory disease. See, e.g., Sandborn et al., *N. Engl. J. Med.*, 2011, 365, 1713-1725; and Panes et al., *BMC Gastroenterol*, 2015, 15, 14. When using a JAK inhibitor to treat gastrointestinal inflammatory conditions such as UC, it would be particularly useful to deliver and release the JAK inhibitor in the gastrointestinal tract (such as in the colon), thereby increasing the level of the JAK inhibitor at site of the inflammation while minimizing systemic exposure.

SUMMARY OF THE INVENTION

In one aspect, the present invention provides novel glucuronide prodrugs of JAK inhibitors which are designed to be cleaved by β-glucuronidase enzymes such as those produced by the microbiome in the gastrointestinal tract. Such cleavage releases the JAK inhibitor in the gastrointestinal tract thereby increasing levels of the JAK inhibitor at the site of gastrointestinal inflammation and minimizing systemic exposure to the JAK inhibitor.

Accordingly, in one aspect, the present invention relates to a compound of formula I:

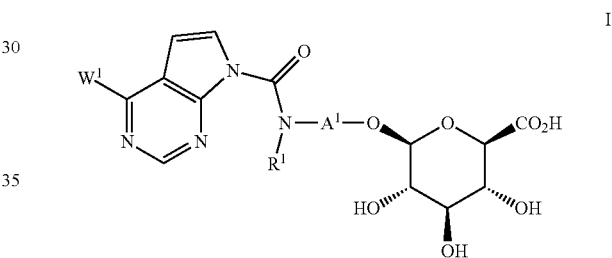

wherein
$R^1$ is hydrogen or $C_{1-3}$alkyl;
$W^1$ is selected from:

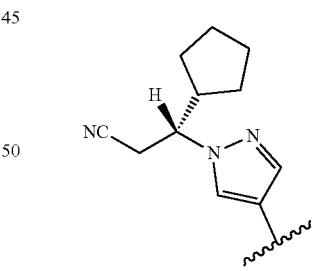

(1)

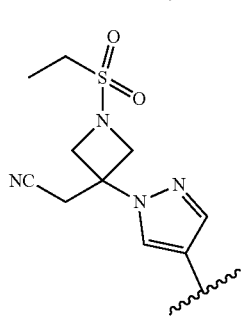

(2)

and

-continued (3)

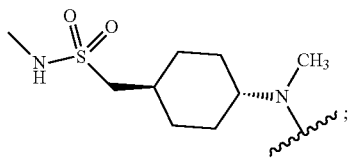

and A¹ is selected from:
(a) a group having formula (i):

—[CH₂]ₐ—N(R²)C(O)—  (i)

wherein a is 2 or 3; and R² is hydrogen or $C_{1-3}$alkyl;
(b) a group having formula (ii):

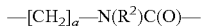

(ii)

wherein b is 0 or 1; c is 0 or 1; R³ is hydrogen or $C_{1-3}$alkyl; and B¹ is selected from $C_{6-10}$aryl, $C_{1-9}$heteroaryl, $C_{3-10}$cycloalkyl and $C_{2-9}$heterocyclic; wherein the heteroaryl group contains from 1 to 4 heteroatoms selected from nitrogen, oxygen and sulfur; the aryl or heteroaryl group is unsubstituted or substituted with 1 to 3 substituents independently selected from $C_{1-4}$alkyl, $C_{1-3}$alkoxy, amino, cyano, halo, hydroxy, nitro and trifluoromethyl; the heterocyclic group contains from 1 to 3 heteroatoms selected from nitrogen, oxygen and sulfur; and the cycloalkyl or heterocyclic group is unsubstituted or substituted with 1 to 4 substituents independently selected from $C_{1-4}$alkyl, $C_{1-3}$alkoxy, hydroxy, and trifluoromethyl;
(c) a group having formula (iii):

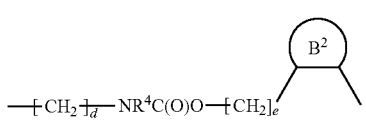

(iii)

wherein d is 2 or 3; e is 0 or 1; R⁴ is hydrogen or $C_{1-3}$alkyl; and B² is selected from $C_{6-10}$aryl, $C_{1-9}$heteroaryl, $C_{3-10}$cycloalkyl and $C_{2-9}$heterocyclic; wherein the heteroaryl group contains from 1 to 4 heteroatoms selected from nitrogen, oxygen and sulfur; the aryl or heteroaryl group is unsubstituted or substituted with 1 to 3 substituents independently selected from $C_{1-4}$alkyl, $C_{1-3}$alkoxy, amino, cyano, halo, hydroxy, nitro and trifluoromethyl; the heterocyclic group contains from 1 to 3 heteroatoms selected from nitrogen, oxygen and sulfur; and the cycloalkyl or heterocyclic group is unsubstituted or substituted with 1 to 4 substituents independently selected from $C_{1-4}$alkyl, $C_{1-3}$alkoxy, hydroxy, and trifluoromethyl; and
(d) a group having the formula (iv)

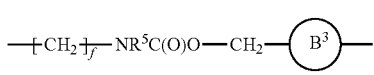

(iv)

wherein f is 2 or 3; R⁵ is hydrogen or $C_{1-3}$alkyl; and B³ is selected from $C_6$-$C_{10}$aryl and $C_{1-9}$heteroaryl; wherein the heteroaryl group contains from 1 to 4 heteroatoms selected from nitrogen, oxygen and sulfur; the aryl or heteroaryl group is unsubstituted or substituted with 1 to 3 substituents independently selected from $C_{1-4}$alkyl, $C_{1-3}$alkoxy, amino, cyano, halo, hydroxy, nitro and trifluoromethyl;

or a pharmaceutically-acceptable salt thereof.

In another aspect, the present invention relates to a compound of formula II:

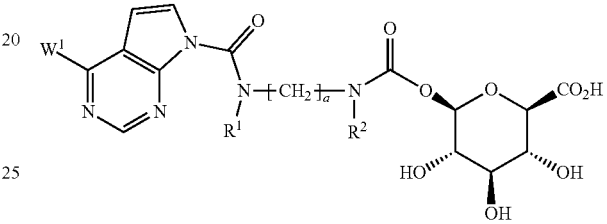

II wherein W¹ is as defined herein; a is 2 or 3; R¹ is hydrogen or $C_{1-3}$alkyl; and R² is hydrogen or $C_{1-3}$alkyl; or a pharmaceutically-acceptable salt thereof.

In another aspect, the present invention relates to a compound of formula III:

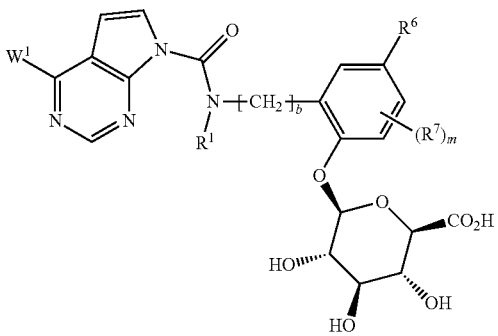

III wherein W¹ is as defined herein; b is 0 or 1; m is 0, 1 or 2; R¹ is hydrogen or $C_{1-3}$ alkyl; R⁶ is hydrogen, $C_{1-4}$alkyl, $C_{1-3}$alkoxy, amino, cyano, halo, hydroxy, nitro or trifluoromethyl; and each R⁷, when present, is independently selected from $C_{1-4}$alkyl, $C_{1-3}$ alkoxy, amino, cyano, halo, hydroxyl, nitro and trifluoromethyl; or a pharmaceutically-acceptable salt thereof.

In another aspect, the present invention relates to a compound of formula IV:

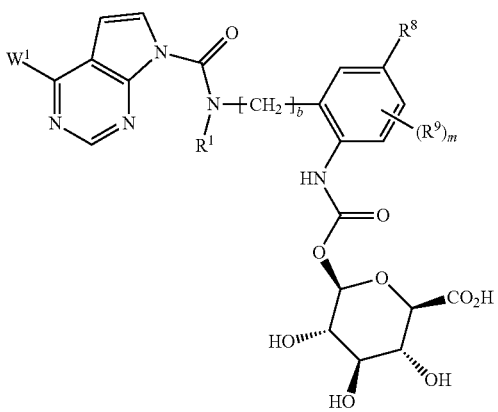

wherein $W^1$ is as defined herein; b is 0 or 1; n is 0, 1 or 2; $R^1$ is hydrogen or $C_{1-3}$ alkyl; $R^8$ is hydrogen, $C_{1-3}$ alkyl, $C_{1-4}$alkyl, $C_{1-3}$alkoxy, amino, halo, cyano, hydroxy, nitro or trifluoromethyl; and each $R^9$, when present, is independently selected from $C_{1-4}$alkyl, $C_{1-3}$ alkoxy, amino, nitro, halo, cyano, hydroxyl, and trifluoromethyl; or a pharmaceutically-acceptable salt thereof.

In another aspect, the present invention relates to a compound of formula V:

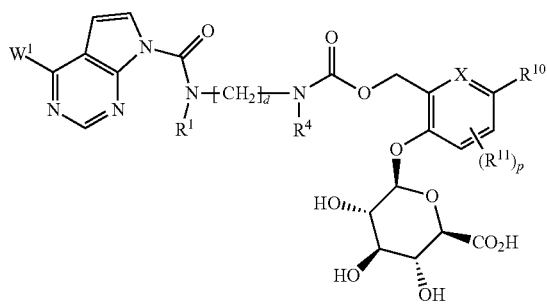

wherein $W^1$ is as defined herein; d is 2 or 3; p is 0, 1 or 2; X is C or N; $R^1$ is hydrogen or $C_{1-3}$alkyl; $R^4$ is hydrogen or $C_{1-3}$alkyl; $R^{10}$ is hydrogen, $C_{1-4}$alkyl, $C_{1-3}$ alkoxy, amino, cyano, halo, hydroxy, nitro or trifluoromethyl; and each $R^{11}$, when present, is independently selected from $C_{1-4}$alkyl, $C_{1-3}$alkoxy, amino, cyano, halo, hydroxyl, nitro and trifluoromethyl; or a pharmaceutically-acceptable salt thereof.

In another aspect, the present invention relates to a compound of formula VI:

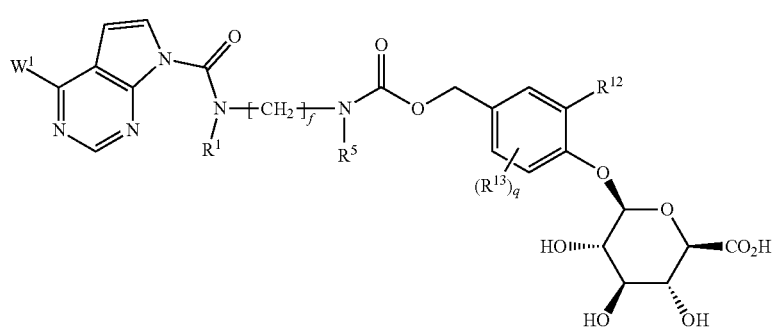

wherein $W^1$ is as defined herein; f is 2 or 3; q is 0, 1 or 2; $R^1$ is hydrogen or $C_{1-3}$ alkyl; $R^5$ is hydrogen or $C_{1-3}$alkyl; $R^{12}$ is hydrogen, $C_{1-4}$alkyl, $C_{1-3}$alkoxy, amino, cyano, halo, hydroxy, nitro or trifluoromethyl; and each $R^{13}$, when present, is independently selected from $C_{1-4}$alkyl, $C_{1-3}$alkoxy, amino, cyano, halo, hydroxyl, nitro and trifluoromethyl; or a pharmaceutically-acceptable salt thereof.

In a particular aspect, the present invention relates to a compound of formula VII:

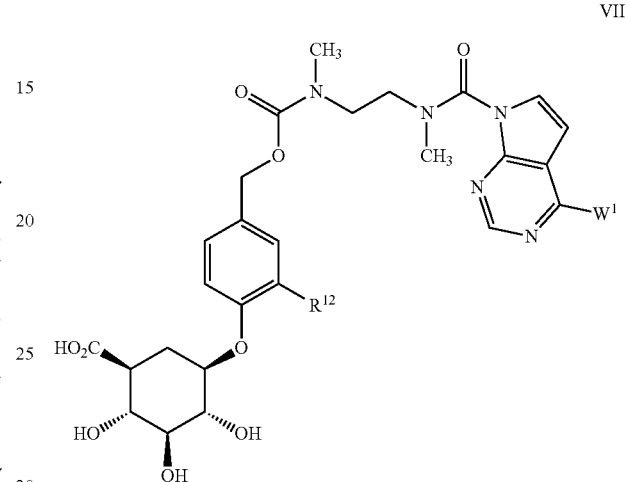

wherein $W^1$ and $R^{12}$ are as defined herein; or a pharmaceutically-acceptable salt thereof.

In separate and distinct aspects, the present invention also relates to:

(2S,3S,4S,5R,6S)-6-(4-(((((2(((2-(4(1-((R)-2-cyano-1-cyclopentylethyl)-1H-pyrazol-4-yl)-N-methyl-7H-pyrrolo[2,3-d]pyrimidine-7-carboxamido)ethyl)(methyl)carbamoyl)-oxy)methyl)-2-nitrophenoxy)-3,4,5-trihydroxytetrahydro-2H-pyran-2-carboxylic acid, or a pharmaceutically-acceptable salt thereof;

(2S,3S,4S,5R,6S)-6-(4-(((((2-(4-(1-(3-(cyanomethyl)-1-(ethylsulfonyl)azetidin-3-yl)-1H-pyrazol-4-yl)-N-methyl-7H-pyrrolo[2,3-d]pyrimidine-7-carboxamido)ethyl)-(methyl)carbamoyl)oxy)methyl)-2-nitrophenoxy)-3,4,5-trihydroxytetrahydro-2H-pyran-2-carboxylic acid, or a pharmaceutically-acceptable salt thereof; and (2S,3S,4S,5R,6S)-3,4,5-trihydroxy-6-(4-(((methyl(2-(N-methyl-4-(methyl((1r,4r)-4-((N-methylsulfamoyl)methyl)cyclohexyl)amino)-7H-pyrrolo[2,3-d]pyrimidine-7-carboxamido)ethyl)carbamoyl)oxy)methyl)-2-nitrophenoxy)

tetrahydro-2H-pyran-2-carboxylic acid, or a pharmaceutically-acceptable salt thereof.

In another aspect, the present invention relates to a pharmaceutical composition comprising a pharmaceutically acceptable-carrier and a compound of formula I, II, III, IV, V, VI or VII (or a specific embodiment thereof), or a pharmaceutically-acceptable salt thereof.

In another aspect, the present invention relates to a method of treating a gastrointestinal inflammatory disease in a mammal. In one embodiment, the method comprises administering to the mammal a compound of formula I, II, III, IV, V, VI or VII (or a specific embodiment thereof), or a pharmaceutically-acceptable salt thereof. In another embodiment, the method comprises administering to the mammal a pharmaceutical composition comprising a pharmaceutically acceptable-carrier and a compound of formula I, II, III, IV, V, VI or VII (or a specific embodiment thereof), or a pharmaceutically-acceptable salt thereof.

In one embodiment, the gastrointestinal inflammatory disease is ulcerative colitis.

In another embodiment, the gastrointestinal inflammatory disease is Crohn's disease. In yet another embodiment, the gastrointestinal inflammatory disease is colitis associated with immune checkpoint inhibitor therapy.

In one embodiment, the mammal being treated is a human.

In separate and distinct aspects, the present invention also relates to synthetic processes and intermediates described herein for preparing a compound of formula I, II, III, IV, V, VI or VII (or a specific embodiment thereof), or a pharmaceutically-acceptable salt thereof.

In separate and distinct aspects, the present invention also relates to a compound of formula I, II, III, IV, V, VI or VII (or a specific embodiment thereof), or a pharmaceutically-acceptable salt thereof; for use in medical therapy; or for use in the manufacture of a medicament or a formulation. In one embodiment, the medicament or formulation is for treating a gastrointestinal inflammatory disease in a mammal.

In another aspect, the present invention relates to a process for preparing a compound of formula I or a pharmaceutically-acceptable salt thereof, the process comprising deprotecting a compound of formula 3:

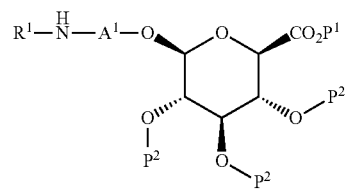

wherein $R^1$, $W^1$ and $A^1$ are as defined herein (including specific embodiments thereof); $P^1$ is a carboxy-protecting group; and each $P^2$ is independently a hydroxyl-protecting group; or a salt thereof; to provide a compound of formula I or a pharmaceutically-acceptable salt thereof.

In another aspect, the present invention relates a process for preparing a compound of formula I or a pharmaceutically-acceptable salt thereof, the process comprising: (a) contacting a compound of formula 1:

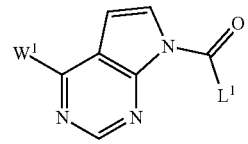

wherein $W^1$ is as defined herein; $L^1$ is an acyl leaving group; or a salt thereof; with a compound of formula 2:

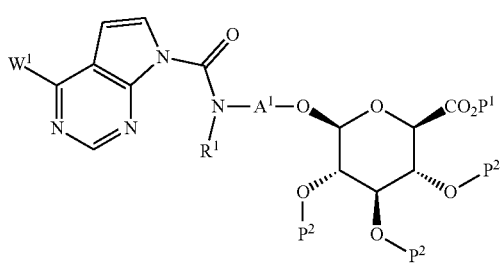

wherein $R^1$ and $A^1$ are as defined herein (including specific embodiments thereof); $P^1$ is a carboxy-protecting group; and each $P^2$ is independently a hydroxyl-protecting group; or a salt thereof; to provide a compound of formula 3, or a salt thereof; and (b) deprotecting the compound of formula 3, or a salt thereof, to provide a compound of formula I or a pharmaceutically-acceptable salt thereof.

In another aspect, the present invention relates to a process for preparing a compound of formula I or a pharmaceutically-acceptable salt thereof, the process comprising: (a) contacting a compound of formula 4:

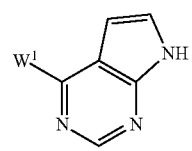

wherein $W^1$ is as defined herein; or a salt thereof; with a compound of formula 5:

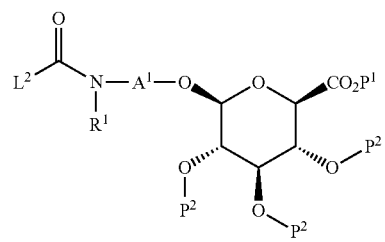

wherein $R^1$ and $A^1$ are as defined herein (including specific embodiments thereof); $L^2$ is an acyl leaving group; $P^1$ is a carboxy-protecting group; and each $P^2$ is independently a hydroxyl-protecting group; or a salt thereof; to provide a compound of formula 3, or a salt thereof; and (b) deprotecting the compound of formula 3, or a salt thereof, to provide a compound of formula I or a pharmaceutically-acceptable salt thereof.

Other aspects and embodiments of this invention are disclosed herein.

DETAILED DESCRIPTION OF THE INVENTION

Among various aspects and embodiments, the present invention relates to glucuronide prodrugs of certain JAK inhibitors or pharmaceutically-acceptable salts thereof; pharmaceutical compositions containing such compounds; methods of using such compounds to treat gastrointestinal inflammatory diseases; and processes and intermediates for preparing such compounds.

The chemical structures herein are typically named according to IUPAC conventions as implemented by ChemDraw Professional software (PerkinElmer, Inc., Cambridge, Mass.). By way of example, ruxolitinib is named (R)-3-(4-(7H-pyrrolo[2,3-d]pyrimidin-4-yl)-1H-pyrazol-1-yl)-3-cyclopentylpropanenitrile; baricitinib is named 2-(3-(4-(7H-pyrrolo[2,3-d]pyrimidin-4-yl)-1H-pyrazol-1-yl)-1-(ethylsulfonyl)azetidin-3-yl)acetonitrile; and oclacitinib is named N-methyl-1-((1r,4r)-4-(methyl(7H-pyrrolo[2,3-d]pyrimidin-4-yl)amino)cyclohexyl)methanesulfonamide.

Compounds described herein may contain one or more chiral centers. In such cases, the depiction or naming of a particular stereoisomer means the indicated stereocenter has the designated stereochemistry with the understanding that minor amounts of other stereoisomers may also be present unless otherwise indicated, provided that the utility of the depicted or named compound is not eliminated by the presence of another stereoisomer.

Additionally, as used herein, "compound of the present invention" and "compound of formula I" (or similar terms) are intended to include pharmaceutically-acceptable salts unless otherwise indicated.

Definitions

When describing this invention including its various aspects and embodiments, the following terms have the following meanings unless otherwise indicated.

The singular terms "a," "an" and "the" include the corresponding plural terms unless the context of use clearly dictates otherwise.

The term "acyl leaving group" means a group or atom that can be displaced by another group or atom (such as an amino group) in a nucleophilic acyl substitution reaction. By way of example, representative acyl leaving groups include, but are not limited to, halides (halo groups), such as chloro, bromo and iodo; acyloxy groups, such as acetoxy, trifluoroacetoxy and the like; phenols, such as p-nitrophenoxy, pentafluorophenoxy and the like.

The term "alkyl" means a monovalent saturated hydrocarbon group which may be linear or branched or combinations thereof. Unless otherwise defined, such alkyl groups typically contain from 1 to about 10 carbon atoms. Representative alkyl groups include, by way of example, methyl, ethyl, n-propyl, isopropyl, n-butyl, sec-butyl, isobutyl, tert-butyl, n-pentyl, n-hexyl, 2,2-dimethylpropyl, 2-methylbutyl, 3-methylbutyl, 2-ethylbutyl, 2,2-dimethylpentyl, 2-propylpentyl, and the like.

When a specific number of carbon atoms are intended for a particular term, the number of carbon atoms is shown preceding the term. For example, the term "$C_{1-3}$ alkyl" means an alkyl group having from 1 to 3 carbon atoms wherein the carbon atoms are in any chemically-acceptable configuration, including linear or branched configurations.

The term "alkoxy" means the monovalent group —O-alkyl, where alkyl is defined as above. Representative alkoxy groups include, by way of example, methoxy, ethoxy, n-propoxy, isopropoxy, n-butoxy, sec-butoxy, isobutoxy, tert-butoxy, and the like.

The term "aryl" means an aromatic hydrocarbon group having a single ring (i.e., phenyl) or fused rings (i.e., naphthalene). Unless otherwise defined, such aryl groups typically contain from 6 to 10 carbon ring atoms. Representative aryl groups include, by way of example, phenyl (i.e., a benzene ring), naphthyl (i.e., a naphthalene ring), and the like. As used herein, the term aryl includes monovalent, divalent or multivalent aryl groups.

The term "carboxyl-protecting group" means a protecting group suitable for preventing undesired reactions at a carboxyl group. Representative carboxyl-protecting groups include, but are not limited to, alkyl groups, such as methyl, ethyl, tert-butyl, and the like; arylmethyl groups, such as benzyl, 4-nitrobenzyl, 4-methoxybenzyl and the like; thiol groups, such as —S-tert-butyl and the like; silyl groups, such as trimethylsilyl, tert-butyldimethylsilyl and the like; oxazolines; and the like.

The term "cycloalkyl" means a saturated carbocyclic hydrocarbon group (i.e., a cycloalkane group) having a single ring or multiple rings (i.e., fused, bridged or spiro rings). Unless otherwise defined, such cycloalkyl groups typically contain from 3 to 10 carbon atoms. Representative cycloalkyl groups include, by way of example, cyclopropyl, cyclobutyl, cyclopentyl, cyclohexyl, cycloheptyl, cyclooctyl, bicyclo[2.2.1]heptane, bicyclo[2.2.2]octane, adamantane, and the like. As used herein, the term cycloalkyl includes monovalent, divalent or multivalent cycloalkyl groups.

The term "halo" means fluoro, chloro, bromo or iodo.

The term "heteroaryl" means an aromatic group having a single ring or two fused rings and containing in a ring at least one heteroatom (typically 1 to 3 heteroatoms) selected from nitrogen, oxygen or sulfur (i.e., a heteroaromatic group). Unless otherwise defined, such heteroaryl groups typically contain from 1 to 9 carbon atoms and from 3 to 10 total ring atoms. Representative heteroaryl groups include, by way of example, mono-, di- or multivalent species of benzimidazole, benzofuran, benzothiazole, benzothiophene, furan, imidazole, indole, isoquinoline, isothiazole, isoxazole, oxazole, pyrazine, pyrazole, pyridazine, pyridine, pyrimidine, pyrrole, quinazoline, quinoline, quinoxaline, tetrazole, thiazole, thiophene, triazole, triazine and the like, where the point or points of attachment are at any available carbon or nitrogen ring atom. As used herein, the term heteroaryl includes monovalent, divalent or multivalent heteroaryl groups.

The term "heterocyclyl" or "heterocyclic" means a saturated or unsaturated (non-aromatic) group having a single ring or multiple rings (i.e., fused, bridged or spiro rings) and containing in a ring at least one heteroatom (typically 1 to 3 heteroatoms) selected from nitrogen, oxygen or sulfur. Unless otherwise defined, such heterocyclic groups typically contain from 2 to 9 carbon atoms and from 3 to 10 total ring atoms.

Representative heterocyclic groups include, by way of example, mono-, di- or multivalent species of include aziridine, azetidine, morpholine, oxetane, oxirane, piperidine, piperazine, pyrrolidine, quinuclidine tetrahydrofuran, tetrahydrothiophene, thiane, thiomorpholine, and the like, where the point or points of attachment are at any available carbon or nitrogen ring atom. As used herein, the term heterocyclyl includes monovalent, divalent or multivalent heterocyclyl groups.

The term "hydroxyl-protecting group" means a protecting group suitable for preventing undesired reactions at a hydroxyl group. Representative hydroxyl-protecting groups include, but are not limited to, alkyl groups, such as methyl, ethyl, and tert-butyl; allyl groups; acyl groups, for example alkanoyl groups, such as acetyl; arylmethyl groups, such as benzyl (Bn), p-methoxybenzyl (PMB), 9-fluorenylmethyl (Fm), and diphenylmethyl (benzhydryl, DPM); silyl groups, such as trimethylsilyl (TMS) and tert-butyldimethylsilyl (TBS); and the like.

The term "pharmaceutically-acceptable" means acceptable for administration to a patient (e.g., having acceptable safety for the specified usage).

The term "pharmaceutically-acceptable salt" means a salt prepared from an acid and a base (including zwitterions) that is acceptable for administration to a patient (e.g., a salt having acceptable safety for a given dosage regime).

The term "salt" means an ionic compound comprising an anion and a cation. For example, the salt may be a hydrogen addition salt formed by reaction of an acid with a base. When a compound contains both an acidic and a basic functional group, such as a carboxylic acid and an amino group, the term "salt" also includes an internal salt or zwitterion.

The term "therapeutically effective amount" means an amount sufficient to effect treatment when administered to a patient in need of treatment, e.g., the amount needed to obtain the desired therapeutic effect.

The term "treating" or "treatment" means ameliorating or suppressing a medical condition, disease or disorder being treated (e.g., a gastrointestinal inflammatory disease); or alleviating the symptoms of the medical condition, disease or disorder.

The term "unit dosage form" or "unit doses" means a physically discrete unit suitable for dosing a patient, i.e., each unit containing a predetermined quantity of a therapeutic agent calculated to produce a therapeutic effect either alone or in combination with one or more additional units. Examples include capsules, tablets and the like.

All other terms used herein are intended to have their ordinary meaning as understood by persons having ordinary skill in the art to which they pertain.

Representative Embodiments and Subgeneric Groupings

The following substituents and values are intended to provide representative examples of various aspects and embodiments of this invention. These representative values are intended to further define and illustrate such aspects and embodiments and are not intended to exclude other embodiments or to limit the scope of this invention.

In one embodiment, the compounds of the present invention are represented by formula I, including pharmaceutically-acceptable salts of such compounds.

In one embodiment, $R^1$ is hydrogen or methyl. In another embodiment, $R^1$ is methyl. In another embodiment, $R^1$ is hydrogen.

In one embodiment, $W^1$ is group of formula (1). In another embodiment, $W^1$ is a group of formula (2). In another embodiment, $W^1$ is a group of formula (3).

In one embodiment, $A^1$ is group of formula (i).

When $A^1$ is a group of formula (i), in one embodiment, a is 2. In another embodiment, a is 3.

In one embodiment, $R^2$ is hydrogen or methyl. In another embodiment, $R^2$ is methyl. In another embodiment, $R^2$ is hydrogen. In another embodiment, both $R^1$ and $R^2$ are methyl.

In another embodiment, $A^1$ is a group of formula (ii).

When $A^1$ is a group of formula (ii), in one embodiment, b is 0. In another embodiment, b is 1.

In one embodiment, c is 0. In another embodiment, c is 1.

In one embodiment, b is 0 and c is 0. In another embodiment, b is 1 and c is 0. In another embodiment, b is 0 and c is 1. In another embodiment, b is 1 and c is 1.

In one embodiment, $R^3$ is hydrogen or methyl. In another embodiment, $R^3$ is hydrogen. In another embodiment, $R^3$ is methyl. In one embodiment, both $R^1$ and $R^3$ are methyl.

In one embodiment, $B^1$ is a $C_{6-10}$aryl group (i.e., an aromatic hydrocarbon group).

Representative aryl groups include phenyl (i.e., a benzene ring) and naphthyl (i.e., a naphthalene ring), where the —[CH$_2$]$_b$— and —[NHC(O)]$_c$— groups are ortho to each other on the aryl ring. In one embodiment, the aryl group is phenyl. The aryl group can be either unsubstituted or substituted with 1 to 3 substituents, where the substituents are located at any available position of the aryl ring. In one embodiment, the aryl group is unsubstituted. In another embodiment, the aryl group is substituted with 1 to 3 substituents independently selected from $C_{1-4}$alkyl, $C_{1-3}$alkoxy, amino, cyano, halo, hydroxy, nitro and trifluoromethyl. In a particular embodiment, the aryl group is substituted with 1 or 2 substituents, including 1 substituent, independently selected from $C_{1-4}$alkyl, halo, nitro and trifluoromethyl. In another particular embodiment, the aryl group is substituted with 1 substituent selected from chloro, methyl, nitro and trifluoromethyl.

In another embodiment, $B^1$ is a $C_{1-9}$ heteroaryl group (i.e., a heteroaromatic group). Representative heteroaryl groups include benzimidazole, benzofuran, benzothiazole, benzothiophene, furan, imidazole, indole, isoquinoline, isothiazole, isoxazole, oxazole, pyrazine, pyrazole, pyridazine, pyridine, pyrimidine, pyrrole, quinazoline, quinoline, quinoxaline, tetrazole, thiazole, thiophene, triazole, triazine and the like, where the —[CH$_2$]$_b$— and —[NHC(O)]$_c$— groups are attached to available adjacent atoms of the heteroaryl ring. The heteroaryl group can be either unsubstituted or substituted with 1 to 3 substituents, where the substituents are located at any available position of the heteroaryl ring. In one embodiment, the heteroaryl group is unsubstituted. In another embodiment, the heteroaryl group is substituted with 1 to 3 substituents independently selected from $C_{1-4}$alkyl, $C_{1-3}$alkoxy, amino, cyano, halo, hydroxy, nitro and trifluoromethyl. In a particular embodiment, the heteroaryl group is substituted with 1 or 2 substituents, including 1 substituent, independently selected from $C_{1-4}$alkyl, halo, nitro and trifluoromethyl. In another particular embodiment, the heteroaryl group is substituted with 1 substituent selected from chloro, methyl, nitro and trifluoromethyl.

In another embodiment, $B^1$ is a $C_{3-10}$cycloalkyl group (i.e., a cycloalkane group). Such cycloalkyl groups can be monocyclic or bicyclic (including fused, bridged and spiro cycloalkanes). Representative cycloalkyl groups include cyclopropyl, cyclobutyl, cyclopentyl, cyclohexyl, cycloheptyl, cycloctyl, bicyclo[2.2.1]heptane, bicyclo[2.2.2]octane, adamantane, and the like, where the —[CH$_2$]$_b$— and —[NHC(O)]$_c$— groups are on adjacent carbon atoms. The cycloalkyl group can be either unsubstituted or substituted with 1 to 4 substituents, where the substituents are located at any available position of the cycloalkyl ring. In one embodiment, the cycloalkyl group is unsubstituted. In another embodiment, the cycloalkyl group is substituted with 1 to 4 substituents independently selected from $C_{1-4}$alkyl, $C_{1-3}$alkoxy, hydroxy, and trifluoromethyl. In a particular embodiment, the aryl group is substituted with 1 or 2 substituents independently selected from $C_{1-4}$alkyl. In another particular embodiment, the cycloalkyl group is substituted 1 or 2 methyl groups.

In another embodiment, $B^1$ is a $C_{2-9}$heterocyclic group (i.e., a heterocycle group). Such heterocyclic groups can be monocyclic or bicyclic (including fused, bridged and spiro heterocycles). Representative heterocyclic groups include aziridine, azetidine, morpholine, oxetane, oxirane, piperidine, piperazine, pyrrolidine, quinuclidine tetrahydrofuran, tetrahydrothiophene, thiane, thiomorpholine, and the like, where the —$[CH_2]_b$— and —$[NHC(O)]_c$— groups are attached to available adjacent atoms of the heterocyclic ring. The heterocyclic group can be either unsubstituted or substituted with 1 to 4 substituents, where the substituents are located at any available position of the heterocyclic ring. In one embodiment, the heterocyclic group is unsubstituted. In another embodiment, the heterocyclic group is substituted with 1 to 4 substituents independently selected from $C_{1-4}$alkyl, $C_{1-3}$alkoxy, hydroxy, and trifluoromethyl. In a particular embodiment, the heterocyclic group is substituted with 1 or 2 substituents independently selected from $C_{1-4}$alkyl. In another particular embodiment, the heterocyclic group is substituted with 1 or 2 methyl groups.

In another embodiment, $A^1$ is a group of formula (iii).

When $A^1$ is a group of formula (iii), in one embodiment, d is 2. In another embodiment, d is 3.

In one embodiment, e is 0. In another embodiment, e is 1.

In one embodiment, d is 2 and e is 0. In another embodiment, d is 2 and e is 1. In another embodiment, d is 3 and e is 0. In another embodiment, d is 3 and e is 1.

In one embodiment, $R^4$ is hydrogen or methyl. In another embodiment, $R^4$ is hydrogen. In another embodiment, $R^4$ is methyl. In one embodiment, both $R^1$ and $R^4$ are methyl.

In one embodiment, $B^2$ is a $C_{6-10}$aryl group (i.e., an aromatic hydrocarbon group). Representative aryl groups include phenyl (i.e., a benzene ring) and naphthyl (i.e., a naphthalene ring), where the —$[CH_2]_e$— and glucuronide groups are ortho to each other on the aryl ring. In one embodiment, the aryl group is phenyl. The aryl group can be either unsubstituted or substituted with 1 to 3 substituents, where the substituents are located at any available position of the aryl ring. In one embodiment, the aryl group is unsubstituted. In another embodiment, the aryl group is substituted with 1 to 3 substituents independently selected from $C_{1-4}$alkyl, $C_{1-3}$alkoxy, amino, cyano, halo, hydroxy, nitro and trifluoromethyl. In a particular embodiment, the aryl group is substituted with 1 or 2 substituents, including 1 substituent, independently selected from $C_{1-4}$alkyl, halo, nitro and trifluoromethyl. In another particular embodiment, the aryl group is substituted with 1 substituent selected from chloro, methyl, nitro and trifluoromethyl.

In another embodiment, $B^2$ is a $C_{1-9}$ heteroaryl group (i.e., a heteroaromatic group). Representative heteroaryl groups include benzimidazole, benzofuran, benzothiazole, benzothiophene, furan, imidazole, indole, isoquinoline, isothiazole, isoxazole, oxazole, pyrazine, pyrazole, pyridazine, pyridine, pyrimidine, pyrrole, quinazoline, quinoline, quinoxaline, tetrazole, thiazole, thiophene, triazole, triazine and the like, where the —$[CH_2]_e$— and glucuronide groups are attached to available adjacent atoms of the heteroaryl ring. The heteroaryl group can be either unsubstituted or substituted with 1 to 3 substituents, where the substituents are located at any available position of the heteroaryl ring. In one embodiment, the heteroaryl group is unsubstituted. In another embodiment, the heteroaryl group is substituted with 1 to 3 substituents independently selected from $C_{1-4}$alkyl, $C_{1-3}$alkoxy, amino, cyano, halo, hydroxy, nitro and trifluoromethyl. In a particular embodiment, the heteroaryl group is substituted with 1 or 2 substituents, including 1 substituent, independently selected from $C_{1-4}$alkyl, halo, nitro and trifluoromethyl. In another particular embodiment, the heteroaryl group is substituted with 1 substituent selected from chloro, methyl, nitro and trifluoromethyl.

In another embodiment, $B^2$ is a $C_{3-10}$cycloalkyl group (i.e., a cycloalkane group). Such cycloalkyl groups can be monocyclic or bicyclic (including fused, bridged and spiro cycloalkanes). Representative cycloalkyl groups include cyclopropyl, cyclobutyl, cyclopentyl, cyclohexyl, cycloheptyl, cyclooctyl, bicyclo[2.2.1]heptane, bicyclo[2.2.2]octane, adamantane, and the like, where the —$[CH_2]_e$— and glucuronide groups are on adjacent carbon atoms. The cycloalkyl group can be either unsubstituted or substituted with 1 to 4 substituents, where the substituents are located at any available position of the cycloalkyl ring. In one embodiment, the cycloalkyl group is unsubstituted. In another embodiment, the cycloalkyl group is substituted with 1 to 4 substituents independently selected from $C_{1-4}$alkyl, $C_{1-3}$alkoxy, hydroxy, and trifluoromethyl. In a particular embodiment, the aryl group is substituted with 1 or 2 substituents independently selected from $C_{1-4}$alkyl. In another particular embodiment, the cycloalkyl group is substituted with 1 or 2 methyl groups.

In another embodiment, $B^2$ is a $C_{2-9}$heterocyclic group (i.e., a heterocycle group). Such heterocyclic groups can be monocyclic or bicyclic (including fused, bridged and spiro heterocycles). Representative heterocyclic groups include aziridine, azetidine, morpholine, oxetane, oxirane, piperidine, piperazine, pyrrolidine, quinuclidine tetrahydrofuran, tetrahydrothiophene, thiane, thiomorpholine, and the like, where the —$[CH_2]_e$— and glucuronide groups are attached to available adjacent atoms of the heterocyclic ring. The heterocyclic group can be either unsubstituted or substituted with 1 to 4 substituents, where the substituents are located at any available position of the heterocyclic ring. In one embodiment, the heterocyclic group is unsubstituted. In another embodiment, the heterocyclic group is substituted with 1 to 4 substituents independently selected from $C_{1-4}$alkyl, $C_{1-3}$alkoxy, hydroxy, and trifluoromethyl. In a particular embodiment, the heterocyclic group is substituted with 1 or 2 substituents independently selected from $C_{1-4}$alkyl. In another particular embodiment, the heterocyclic group is substituted with 1 or 2 methyl groups.

In another embodiment, $A^1$ is a group of formula (iv).

When $A^1$ is a group of formula (iv), in one embodiment, f is 2. In another embodiment, f is 3.

In one embodiment, $R^5$ is hydrogen or methyl. In another embodiment, $R^5$ is hydrogen. In another embodiment, $R^5$ is methyl. In one embodiment, both $R^1$ and $R^5$ are methyl.

In one embodiment, $B^3$ is a $C_{6-10}$aryl group (i.e., an aromatic hydrocarbon group). Representative aryl groups include phenyl (i.e., a benzene ring) and naphthyl (i.e., a naphthalene ring), where the —$CH_2$— and glucuronide groups are para to each other or are in a 1,4-orientation on the aryl ring. In one embodiment, the aryl group is phenyl. The aryl group can be either unsubstituted or substituted with 1 to 3 substituents, where the substituents are located at any available position of the aryl ring. In one embodiment, the aryl group is unsubstituted. In another embodiment, the aryl group is substituted with 1 to 3 substituents independently selected from $C_{1-4}$alkyl, $C_{1-3}$alkoxy, amino, cyano, halo, hydroxy, nitro and trifluoromethyl. In a particular embodiment, the aryl group is substituted with 1 or 2 substituents, including 1 substituent, independently selected from $C_{1-4}$alkyl, halo, nitro and trifluoromethyl. In another particular embodiment, the aryl group is substituted with 1 substituent selected from chloro, methyl, nitro and trifluoromethyl.

In another embodiment, $B^3$ is a $C_{1-9}$heteroaryl group (i.e., a heteroaromatic group). Representative heteroaryl groups include benzimidazole, benzofuran, benzothiazole, benzothiophene, furan, imidazole, indole, isoquinoline, isothiazole, isoxazole, oxazole, pyrazine, pyrazole, pyridazine, pyridine, pyrimidine, pyrrole, quinazoline, quinoline, quinoxaline, tetrazole, thiazole, thiophene, triazole, triazine and the like, where the —$CH_2$— and glucuronide groups are para to each other or are in a 1,4-orientation on the heteroaryl ring. The heteroaryl group can be either unsubstituted or substituted with 1 to 3 substituents, where the substituents are located at any available position of the heteroaryl ring. In one embodiment, the heteroaryl group is unsubstituted. In another embodiment, the heteroaryl group is substituted with 1 to 3 substituents independently selected from $C_{1-4}$alkyl, $C_{1-3}$alkoxy, amino, cyano, halo, hydroxy, nitro and trifluoromethyl. In a particular embodiment, the heteroaryl group is substituted with 1 or 2 substituents, including 1 substituent, independently selected from $C_{1-4}$alkyl, halo, nitro and trifluoromethyl. In another particular embodiment, the heteroaryl group is substituted with 1 substituent selected from chloro, methyl, nitro and trifluoromethyl.

In a particular embodiment, the compounds of the present invention are represented by formula II, including pharmaceutically-acceptable salts of such compounds. In this embodiment, $A^1$ is a group of formula (i) and a, $W^1$, $R^1$ and $R^2$ are as defined for formula I including any specific embodiments thereof.

In a particular embodiment, $R^1$ is methyl; $R^2$ is methyl; and a is 2 or 3.

In another embodiment, the compounds of the present invention are represented by formula III, including pharmaceutically-acceptable salts of such compounds. In this embodiment, $A^1$ is a group of formula (ii) where $B^1$ is an optionally substituted phenyl group as defined in formula III; c is 0; and b, $W^1$ and $R^1$ are as defined for formula I including any specific embodiments thereof.

In one embodiment, $R^6$ is hydrogen, $C_{1-4}$alkyl, $C_{1-3}$alkoxy, amino, cyano, halo, hydroxy, nitro or trifluoromethyl. In another embodiment, $R^6$ is hydrogen, $C_{1-4}$alkyl, halo or trifluoromethyl. In another embodiment, $R^6$ is hydrogen, methyl, chloro or trifluoromethyl. In a particular embodiment, $R^6$ is hydrogen.

In one embodiment, m is 0. In another embodiment, m is 1. In yet another embodiment, m is 2. In one embodiment, m is 0 or 1.

When m is 1, in one embodiment, $R^7$ is $C_{1-4}$alkyl, $C_{1-3}$alkoxy, halo or trifluoromethyl. In another embodiment, $R^7$ is $C_{1-4}$alkyl, $C_{1-3}$alkoxy, fluoro, chloro or trifluoromethyl. In another embodiment, $R^7$ is methyl, fluoro, chloro or trifluoromethyl. In a particular embodiment, $R^7$ is fluoro.

When m is 1, the $R^7$ substituent may be in any available position of the phenyl ring to which $R^7$ is attached. In one embodiment, $R^7$ is ortho to $R^6$. In another embodiment, $R^7$ is meta to $R^6$.

When m is 2, in one embodiment, each $R^7$ is independently $C_{1-4}$alkyl, $C_{1-3}$alkoxy, halo or trifluoromethyl. In another embodiment, each $R^7$ is independently $C_{1-4}$alkyl, $C_{1-3}$alkoxy, fluoro, chloro or trifluoromethyl. In another embodiment, each $R^7$ is independently methyl, fluoro, chloro or trifluoromethyl. In a particular embodiment, each $R^7$ is fluoro.

When m is 2, the $R^7$ substituents may be in any available position of the phenyl ring to which $R^7$ is attached. In one embodiment, the $R^7$ substituents are ortho and meta to $R^6$. In another embodiment, the $R^7$ substituents are both ortho to $R^6$.

In a particular embodiment, b is 0; m is 0; $R^1$ is methyl; and $R^6$ is hydrogen, $C_{1-4}$alkyl, halo or trifluoromethyl; including where $R^6$ is hydrogen, methyl, chloro or trifluoromethyl.

In another embodiment, the compounds of the present invention are represented by formula IV, including pharmaceutically-acceptable salts of such compounds. In this embodiment, $A^1$ is a group of formula (ii) where $B^1$ is an optionally substituted phenyl group as defined in formula IV; c is 1; $R^3$ is hydrogen; and b, $W^1$ and $R^1$ are as defined for formula I including any specific embodiments thereof.

In one embodiment, $R^8$ is hydrogen, $C_{1-4}$alkyl, $C_{1-3}$alkoxy, amino, cyano, halo, hydroxy, nitro or trifluoromethyl. In another embodiment, $R^8$ is hydrogen, $C_{1-4}$alkyl, halo or trifluoromethyl. In another embodiment, $R^8$ is hydrogen, methyl, chloro or trifluoromethyl. In a particular embodiment, $R^8$ is hydrogen.

In one embodiment, n is 0. In another embodiment, n is 1. In yet another embodiment, n is 2. In one embodiment, n is 0 or 1.

When n is 1, in one embodiment, $R^9$ is $C_{1-4}$alkyl, $C_{1-3}$alkoxy, halo or trifluoromethyl. In another embodiment, $R^9$ is $C_{1-4}$alkyl, $C_{1-3}$alkoxy, fluoro, chloro or trifluoromethyl. In another embodiment, $R^9$ is methyl, fluoro, chloro or trifluoromethyl. In a particular embodiment, $R^9$ is fluoro.

When n is 1, the $R^9$ substituent may be in any available position of the phenyl ring to which $R^9$ is attached. In one embodiment, $R^9$ is ortho to $R^8$. In another embodiment, $R^9$ is meta to $R^8$.

When n is 2, in one embodiment, each $R^9$ is independently $C_{1-4}$alkyl, $C_{1-3}$alkoxy, halo or trifluoromethyl. In another embodiment, each $R^9$ is independently $C_{1-4}$alkyl, $C_{1-3}$alkoxy, fluoro, chloro or trifluoromethyl. In another embodiment, each $R^9$ is independently methyl, fluoro, chloro or trifluoromethyl. In a particular embodiment, each $R^9$ is fluoro.

When n is 2, the $R^9$ substituents may be in any available position of the phenyl ring to which $R^9$ is attached. In one embodiment, the $R^9$ substituents are ortho and meta to $R^8$. In another embodiment, the $R^9$ substituents are both ortho to $R^8$.

In one embodiment, b is 1; n is 0; $R^1$ is methyl; and $R^8$ is hydrogen, $C_{1-4}$alkyl, halo or trifluoromethyl; including where $R^8$ is hydrogen, methyl, chloro or trifluoromethyl.

In another embodiment, the compounds of the present invention are represented by formula V, including pharmaceutically-acceptable salts of such compounds. In this embodiment, $A^1$ is a group of formula (iii) where $B^2$ is an optionally substituted phenyl or pyridyl group as defined in formula V; e is 1; and d, $R^1$ and $R^4$ are as defined for formula I including any specific embodiments thereof.

In one embodiment, X is C, a carbon atom (i.e., $A^1$ is a phenyl group). In another embodiment, X is N, a nitrogen atom (i.e., $A^1$ is a pyridyl group).

In one embodiment, $R^{10}$ is hydrogen, $C_{1-4}$alkyl, $C_{1-3}$alkoxy, amino, cyano, halo, hydroxy, nitro or trifluoromethyl. In another embodiment, $R^{10}$ is hydrogen, $C_{1-4}$alkyl, halo or trifluoromethyl. In another embodiment, $R^{10}$ is hydrogen, methyl, chloro or trifluoromethyl. In a particular embodiment, $R^{10}$ is hydrogen.

In one embodiment, p is 0. In another embodiment, p is 1. In yet another embodiment, p is 2. In one embodiment, p is 0 or 1.

When p is 1, in one embodiment, $R^{11}$ is $C_{1-4}$alkyl, $C_{1-3}$alkoxy, halo or trifluoromethyl. In another embodiment, $R^{11}$ is $C_{1-4}$alkyl, $C_{1-3}$alkoxy, fluoro, chloro or trifluoromethyl. In another embodiment, $R^{11}$ is methyl, fluoro, chloro or trifluoromethyl. In a particular embodiment, $R^{11}$ is fluoro.

When p is 1, the $R^{11}$ substituent may be in any available position of the phenyl ring to which $R^{11}$ is attached. In one embodiment, $R^{11}$ is ortho to $R^{10}$. In another embodiment, $R^{11}$ is meta to $R^{10}$.

When p is 2, in one embodiment, each $R^{11}$ is independently $C_{1-4}$alkyl, $C_{1-3}$alkoxy, halo or trifluoromethyl. In another embodiment, each $R^{11}$ is independently $C_{1-4}$alkyl, $C_{1-3}$alkoxy, fluoro, chloro or trifluoromethyl. In another embodiment, each $R^{11}$ is independently methyl, fluoro, chloro or trifluoromethyl. In a particular embodiment, each $R^{11}$ is fluoro.

When p is 2, the $R^{11}$ substituents may be in any available position of the phenyl ring to which $R^{11}$ is attached. In one embodiment, the $R^{11}$ substituents are ortho and meta to $R^{10}$. In another embodiment, the $R^{11}$ substituents are both ortho to $R^{10}$ (when X is C).

In one embodiment, d is 2; p is 0; $R^1$ is methyl; $R^4$ is methyl; and $R^{10}$ is hydrogen, $C_{1-4}$alkyl, halo or trifluoromethyl; including where $R^{10}$ is hydrogen, methyl, chloro or trifluoromethyl.

In another embodiment, the compounds of the present invention are represented by formula VI, including pharmaceutically-acceptable salts of such compounds. In this embodiment, $A^1$ is a group of formula (iv) where $B^3$ is an optionally substituted phenyl group as defined in formula VI; and f $W^1$, $R^1$ and $R^5$ are as defined for formula I including any specific embodiments thereof.

In one embodiment, $R^{12}$ is hydrogen, $C_{1-4}$alkyl, $C_{1-3}$alkoxy, amino, cyano, halo, hydroxy, nitro or trifluoromethyl. In another embodiment, $R^{12}$ is hydrogen, $C_{1-4}$alkyl, halo, nitro or trifluoromethyl. In another embodiment, $R^{12}$ is hydrogen, methyl, nitro, chloro or trifluoromethyl. In a particular embodiment, $R^{12}$ is hydrogen. In another particular embodiment, $R^{12}$ is nitro.

In one embodiment, q is 0. In another embodiment, q is 1. In yet another embodiment, q is 2. In one embodiment, q is 0 or 1.

When q is 1, in one embodiment, $R^{13}$ is $C_{1-4}$alkyl, $C_{1-3}$alkoxy, halo or trifluoromethyl. In another embodiment, $R^{13}$ is $C_{1-4}$alkyl, $C_{1-3}$alkoxy, fluoro, chloro or trifluoromethyl. In another embodiment, $R^{13}$ is methyl, fluoro, chloro or trifluoromethyl. In a particular embodiment, $R^{13}$ is fluoro.

When q is 1, the $R^{13}$ substituent may be in any available position of the phenyl ring to which $R^{13}$ is attached. In one embodiment, $R^{13}$ is ortho to $R^{12}$. In another embodiment, $R^{13}$ is meta to $R^{12}$. In another embodiment, $R^{13}$ is para to $R^{12}$.

When q is 2, in one embodiment, each $R^{13}$ is independently $C_{1-4}$alkyl, $C_{1-3}$alkoxy, halo or trifluoromethyl. In another embodiment, each $R^{13}$ is independently $C_{1-4}$alkyl, $C_{1-3}$alkoxy, fluoro, chloro or trifluoromethyl. In another embodiment, each $R^{13}$ is independently methyl, fluoro, chloro or trifluoromethyl. In a particular embodiment, each $R^{13}$ is fluoro.

When q is 2, the $R^{13}$ substituents may be in any available position of the phenyl ring to which $R^{12}$ is attached. In one embodiment, the $R^{13}$ substituents are ortho and meta to $R^{12}$. In another embodiment, the $R^{13}$ substituents are ortho and para to $R^{12}$. In another embodiment, the $R^{13}$ substituents are meta and para to $R^{12}$.

In one embodiment, f is 2; q is 0; $R^1$ is methyl; $R^5$ is methyl; and $R^{12}$ is hydrogen, $C_{1-4}$alkyl, halo, nitro or trifluoromethyl; including where $R^{12}$ is hydrogen, methyl, nitro, chloro or trifluoromethyl.

In another embodiment, the compounds of the present invention are represented by formula VII, including pharmaceutically-acceptable salts of such compounds. In this embodiment, f is 2; $R^1$ and $R^5$ are methyl; $A^1$ is a group of formula (iv) where $B^3$ is an optionally substituted phenyl group as defined in formula VII; and $W^1$ is as defined for formula I including any specific embodiments thereof.

In one embodiment, $R^{12}$ is hydrogen, $C_{1-4}$alkyl, $C_{1-3}$alkoxy, amino, cyano, halo, hydroxy, nitro or trifluoromethyl. In another embodiment, $R^{12}$ is hydrogen, $C_{1-4}$alkyl, halo, nitro or trifluoromethyl. In another embodiment, $R^{12}$ is hydrogen, methyl, nitro, chloro or trifluoromethyl. In a particular embodiment, $R^{12}$ is hydrogen. In another particular embodiment, $R^{12}$ is nitro.

General Synthetic Procedures

Compounds of this invention, and intermediates thereof, can be prepared according to the following general methods and procedures using commercially-available or routinely-prepared starting materials and reagents. The substituents and variables (e.g., $R^1$, $A^1$, etc.) used in the following schemes have the same meanings as those defined elsewhere herein unless otherwise indicated. Additionally, compounds having an acidic or basic atom or functional group may be used or may be produced as a salt unless otherwise indicated (in some cases, the use of a salt in a particular reaction will require conversion of the salt to a non-salt form, e.g., a free base, using routine procedures before conducting the reaction).

Scheme 1 illustrates typical procedures for preparing compounds of formula I:

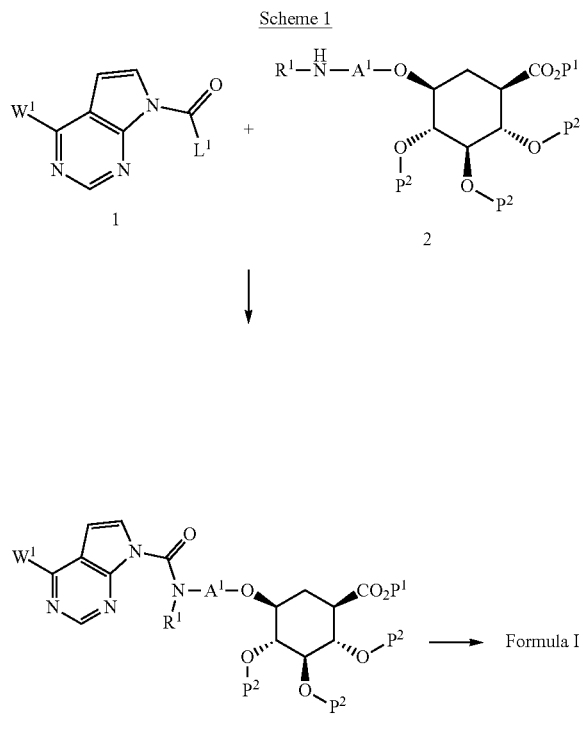

-continued

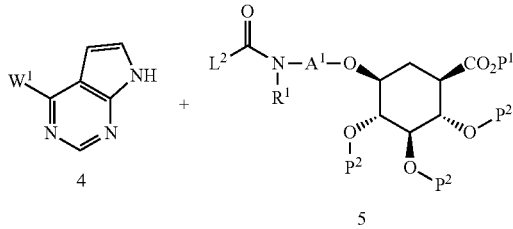

wherein $W^1$ is as defined herein;

$L^1$ and $L^2$ are acyl leaving groups, such as chloro, p-nitrophenoxy or pentafluorophenoxy;

$P^1$ is a carboxyl-protecting group, such as $C_{1-4}$alkyl or benzyl; and each $P^2$ is a hydroxyl-protecting group; such as acetyl or allyl.

As shown in Scheme 1, compound 1 can be reacted with compound 2 to form protected intermediate 3. This reaction is typically conducted by contacting 1 with about 0.9 to about 1.5 molar equivalents of 2 in an inert diluent, such as dichloromethane and the like, at a temperature ranging from about −10° C. to about 30° C. for about 0.5 to about 24 hours, or until the reaction is substantially complete. Optionally, the reaction is conducted in the presence of a base (typically about 2 to about 12 molar equivalents of a base), such as triethylamine, diisopropylethylamine and the like. Upon completion of the reaction, the product is typically isolated using conventional procedures, such as extraction, recrystallization, chromatography and the like. Alternatively, if desired, the reaction mixture containing compound 3 can be used directly in the next step of the synthesis without further isolation or purification.

Compounds of formula 1 are known in the art or can be prepared from commercially available starting materials and reagents using known procedures. In a particular embodiment, $L^1$ in 1 is p-nitrophenoxy or pentafluorophenoxy. By way of illustration, compound 1 wherein $L^1$ is p-nitrophenoxy is prepared by reacting ruxolitinib, baricitinib or oclacitinib with a molar excess, such as about 2 molar equivalents, of 4-nitrophenyl chloroformate in a two-phase mixture of water and an organic diluent, such as dichloromethane and the like, containing an excess amount of a base, such as an alkali hydroxide (e.g., sodium hydroxide) and the like, and a catalytic amount of a phase transfer catalyst, such as tetrabutylamonium bromide and the like. This reaction is typically conducted at a temperature ranging from about 0° C. to about 30° C. for about 0.5 to about 6 hours, or until the reaction is substantially complete. Upon completion of the reaction, the product is typically isolated using conventional procedures, such as extraction, recrystallization, chromatography and the like.

The compounds of formula 2 are prepared by conventional procedures using commercially available starting materials and reagents. Representative examples of various methods for preparing compounds of formula 2 are provided in the Examples herein.

Alternatively, as shown in Scheme 1, compound 4 (e.g., ruxolitinib, baricitinib or oclacitinib) can be reacted with compound 5 to form protected intermediate 3. This reaction is typically conducted by contacting 5 with about 1 to about 1.5 molar equivalents of 4 in an inert diluent, such as dichloromethane and the like, at a temperature ranging from about 0° C. to about 30° C. for about 1 to about 24 hours, or until the reaction is substantially complete. The reaction is typically conducted in the presence of an excess amount, such as about 1.5 to about 3 molar equivalents of an organic base, such as triethylamine, diisopropylethylamine and the like. Optionally, the reaction is conducted in presence of a catalytic amount, such as about 0.1 molar equivalents, of N,N-dimethylaminopyridine. Upon completion of the reaction, the product is typically isolated using conventional procedures, such as extraction, recrystallization, chromatography and the like. Alternatively, if desired, the reaction mixture containing compound 3 can be used directly in the next step of the synthesis without further isolation or purification.

The compounds of formula 5 are typically prepared from a compound of formula 2. In a particular embodiment, $L^2$ in 5 is chloro. By way of illustration, compound 5 wherein $L^1$ is chloro is prepared by reacting 2 with phosgene or a phosgene equivalent. This reaction is typically conducted by contacting 2 with an excess of phosgene, such as about 2 to about 4 molar equivalents of phosgene in an inert diluent, such as dichloromethane, toluene and the like, at a temperature ranging from about 0° C. to about 30° C. for about 1 to about 24 hours, or until the reaction is substantially complete. The reaction is typically conducted in the presence of an excess amount, such as about 1.5 to about 3 molar equivalents of an organic base, such as triethylamine, diisopropylethylamine and the like. Upon completion of the reaction, the product is typically isolated using conventional procedures, such as extraction, recrystallization, chromatography and the like.

As shown in Scheme 1, compound 3 is then deprotected to provide a compound of formula I. The particular conditions used to deprotect compound 3 will depend on the protecting groups employed. For example, when $P^1$ is a $C_{1-4}$alkyl group, such as methyl, ethyl, and the like, and each $P^2$ is acetyl and the like, this deprotection reaction is typically conducted by contacting compound 3 with about 4 to about 4.5 molar equivalents of an alkali hydroxide, such as lithium hydroxide and the like. This reaction is typically conducted in a diluent, such as water, THF, methanol and the like, and combinations thereof, such as water and THF or water, THF and methanol (e.g., a 1:1:1 mixture). Typically, this reaction is conducted at a temperature ranging from about −10° C. to about 30° C. for about 0.5 to about 24 hours, or until the reaction is substantially complete.

Alternatively, when $P^1$ is a $C_{1-4}$alkyl group, such as methyl, ethyl, and the like, and each $P^2$ is acetyl and the like, the deprotection reaction can be conducted by contacting compound 3 with a mixture of diisopropylethylamine in water and methanol. Typically, this reaction is conducted at a temperature ranging from about 0° C. to about 30° C. for about 1 to about 24 hours, or until the reaction is substantially complete.

Upon completion of the deprotection reaction, the product is typically isolated using conventional procedures, such as extraction, recrystallization, chromatography and the like.

In one embodiment, the compounds of this invention are used in the form of a pharmaceutically-acceptable salt. Representative pharmaceutically-acceptable salts include salts of the following acids (with the corresponding anion shown in parentheses): acetic (acetate), ascorbic (ascorbate), benzenesulfonic (benzenesulfononate or besylate), benzoic (benzoate), camphorsulfonic (camphorsulfonate), chlortheophylline (chlortheophyllinate), citric (citrate), ethanesulfonic (ethanesulfonate), ethanedisulfonic or edisylic (ethanedisulfonate or edisylate), fumaric (fumarate), gentisic (gentisate), gluconic (gluconate), glucuronic (glucoronate), gluceptic (gluceptate), glutamic (glutamate), hippuric (hippurate), hydrobromic (bromide), hydrochloric (chloride), hydroiodic (iodide), isethionic (isethionate), lactic (lactate), lactobionic (lactobionate), laurylsulfonic (laurylsulfonate), maleic (maleate), malic (malate), mandelic (mandelate), methanesulfonic (methanesulfonate or mesylate), methyl sulfonic (methyl sulfonate), mucic (mucate), naphthalenesulfonic (naphthalenesulfonate or napsylate), naphthalene-1,5-disulfonic (naphthalene-1,5-disulfonate), naphthalene-2,6-disulfonic (naphthalene-2,6-disulfonate), naphthoic (naphthoate), nicotinic (nicotinate), nitric (nitrate), octadecanonic (octadecanoate), oleic (oleate), orotic (orotate), oxalic (oxalate), pamoic (pamoate), pantothenic (pantothenate), phosphoric (phosphate), polygalacturonic (polygalacturonate), succinic (succinate), sulfosalicylic (sulfosalicylate), sulfuric (sulfate), tartaric (tartarate), p-toluenesulfonic (p-toluenesulfonate or tosylate) and xinafoic (xinafoate) acid, and the like. Such salts are sometimes referred to as acid addition salts.

Representative salts derived from pharmaceutically-acceptable inorganic bases include ammonium, calcium, magnesium, potassium, sodium, and zinc, and the like. Representative salts derived from pharmaceutically-acceptable organic bases include salts of arginine, choline, glucamine, lysine, benethamine, benzathine, betaine, 2-dimethylaminoethanol, 2-diethylaminoethanol, hydrabamine, morpholine, tromethamine, diethanolamine, ethanolamine, ethylenediamine, triethanolamine, 1H-imidazole, piperazine, and the like.

The salts can be prepared by contacting one molar equivalent of a compound of the invention with the appropriate molar equivalents of the acid or base (taking into consideration the number of acidic or basic moieties on the compound of the invention and the acid or base reactant). Such reactions are typically conducted in a diluent, such as dichloromethane, ethanol, ethyl acetate, isopropyl acetate and the like, at a temperature ranging from about −20° C. to about 50° C. for about 0.5 to about 12 hours or until the reaction is substantially complete. Upon completion of the reaction, the product is typically isolated using conventional procedures, such as filtration, chromatography, recrystallization, and the like.

Other methods and conditions for preparing the compounds of the invention are described in the Examples herein.

Cleavage of Glucuronide Prodrug Moiety

When contacted with β-glucuronidase enzymes, e.g., in the gastrointestinal tract, the glucuronide prodrug moiety of the compounds of the present invention is cleaved by the β-glucuronidase enzyme and the intermediate compound produced further reacts to release the JAK inhibitor. The exact mechanism for release of the JAK inhibitor depends on the chemical structure of the prodrug moiety. While not intending to be limited to a particular mechanism or theory, a depiction of such cleavage for a representative prodrug moiety is illustrated in Scheme 2A.

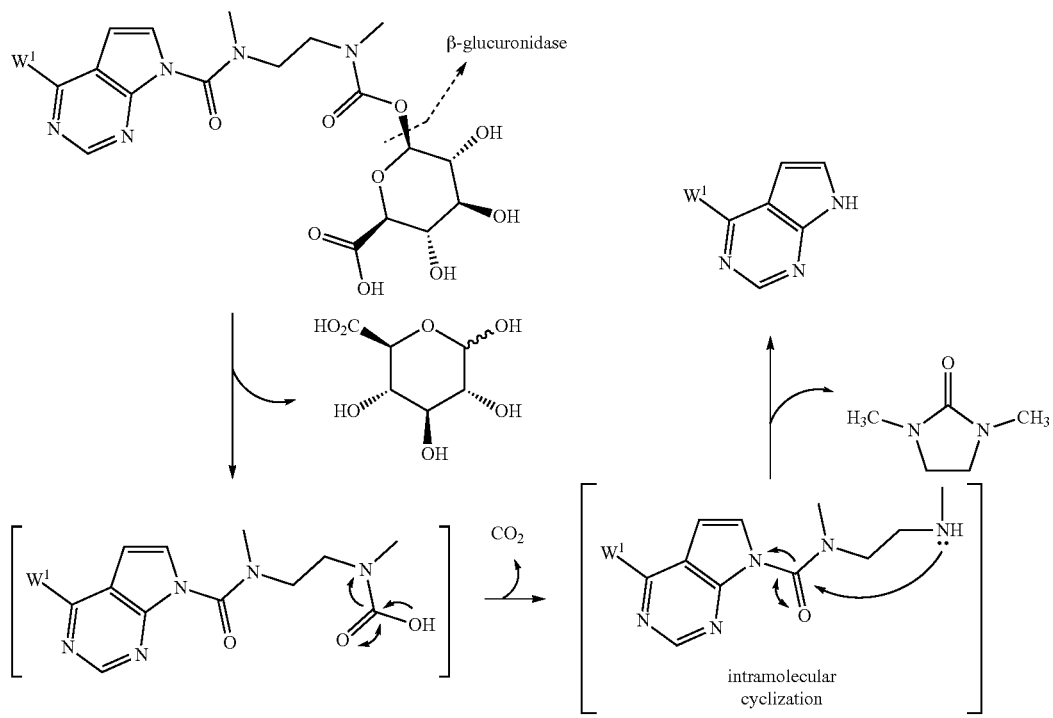

Scheme 2A

As shown in Scheme 2A, the β-glucuronidase enzyme cleaves the glycosidic bond of the glucuronide prodrug compound thereby releasing glucuronic acid. The resulting carbamic acid intermediate then releases carbon dioxide to produce an amine-containing intermediate. Intramolecular cyclization of the amino group then forms an imidazolidinone derivative and releases the JAK inhibitor.

For compounds of Formula VII, the cleavage is believed to generate a quinone methide intermediate. While not intending to be limited to a particular mechanism or theory, a depiction of such cleavage for a representative prodrug moiety is illustrated in Scheme 2B:

depending on the chemical structure of the particular compound of the present invention. However, in each case,

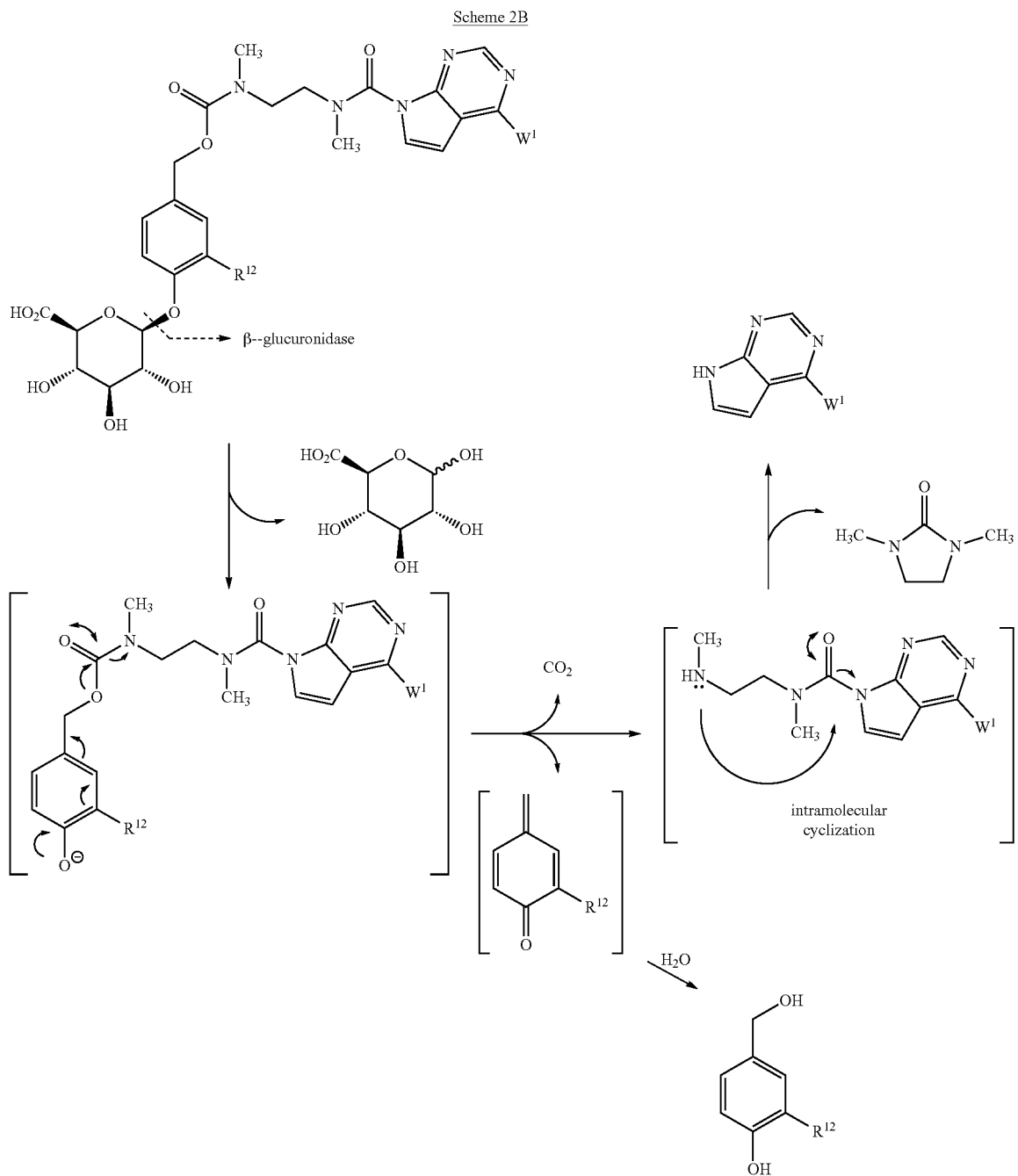

Scheme 2B

As shown in Scheme 2B, the β-glucuronidase enzyme cleaves the glycosidic bond of the glucuronide prodrug compound thereby releasing glucuronic acid. The resulting aglycone intermediate then releases carbon dioxide and a quinone methide intermediate (which can react with water) to produce an amine-containing intermediate.

Intramolecular cyclization of the amino group then forms an imidazolidinone derivative and releases the JAK inhibitor.

Those skilled in the art will appreciate that the exact mechanism for the release of the JAK inhibitor may vary cleavage of the glucuronide prodrug moiety by the β-glucuronidase enzyme causes the compound to release the JAK inhibitor.

Pharmaceutical Compositions

The compounds of the present invention are typically used in the form of a pharmaceutical composition or formulation. When discussing such compositions herein, a compound of the present invention may be referred to as the "active agent" to distinguish it from other components of the composition such as the carrier or excipient. Thus, the term "active agent" includes, e.g., a compound of formula I as well as a pharmaceutically-acceptable salt thereof. Also, the terms "composition" and "formulation" are used interchangeably herein and have the same meaning unless otherwise indicated. Similarly, the terms "carrier" and "excipient" are used interchangeably herein and have the same meaning unless otherwise indicated.

Such pharmaceutical compositions typically contain a therapeutically effective amount of a compound of the present invention. Those skilled in the art will recognize, however, that pharmaceutical compositions may contain more than a therapeutically effective amount, i.e., bulk or concentrated compositions intended for further dilution, or less than a therapeutically effective amount, i.e., individual unit doses intended for multiple administration to achieve a therapeutically effective amount.

Typically, a pharmaceutical composition will contain from about 0.01 to about 95 wt. % of active agent, including, from about 0.01 to about 30 wt. %, such as from about 0.01 to about 10 wt. %, with the actual amount depending upon the formulation, the route of administration, the frequency of dosing, and so forth. For example, a pharmaceutical composition suitable as an oral dosage form may contain about 0.1 to about 10 wt. %, including from about 0.5 to about 5 wt. %, of active agent.

In one embodiment, the pharmaceutical composition contains from about 0.5 to about 50 mg of active agent per unit dose, including from about 1 to about 40 mg of active agent per unit dose, such as about 1 to about 20 mg of active agent per unit dose.

Any conventional or suitable pharmaceutically-acceptable carrier may be used in the pharmaceutical compositions of this invention. The choice of a particular carrier, or combinations of carriers, will depend on various factors, such as the mode of administration, dosage amount, frequency of dosing, timing of release of the active agent and the like. In this regard, the preparation of a suitable pharmaceutical composition for a particular mode of administration is well within the scope of those skilled in the pharmaceutical arts, and carriers used in such compositions are commercially available.

By way of further illustration, conventional formulations and formulation techniques are described in, e.g., *Remington: The Science and Practice of Pharmacy*, 20$^{th}$ Edition, Lippincott Williams & White, Baltimore, Md. (2000); and H. C. Ansel et al., *Pharmaceutical Dosage Forms and Drug Delivery Systems*, 7$^{th}$ Edition, Lippincott Williams & White, Baltimore, Md. (1999).

Representative examples of pharmaceutically-acceptable carriers include, but are not limited to: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; compressed propellant gases, such as chlorofluorocarbons and hydrofluorocarbons; and other non-toxic compatible substances employed in pharmaceutical compositions.

Pharmaceutical compositions are typically prepared by thoroughly and intimately mixing or blending the active agent with a pharmaceutically-acceptable carrier and any optional ingredients. The resulting uniformly blended mixture may then be shaped or loaded into tablets, capsules, pills, canisters, cartridges, vials, bottles, dispensers, and the like, using conventional procedures and equipment.

In one embodiment, the pharmaceutical composition is suitable for oral administration. Pharmaceutical compositions for oral administration may be in the form of, for example, capsules, tablets, pills, lozenges, cachets, dragees, powders, granules, solutions, suspensions, emulsions, elixirs, syrups, and the like; each containing a predetermined amount of the active agent.

When intended for oral administration in a solid dosage form (such as capsules, tablets, and the like), the pharmaceutical composition will typically comprise the active agent and one or more pharmaceutically-acceptable solid carriers, such as sodium citrate or dicalcium phosphate. Solid dosage forms may also comprise: fillers or extenders, such as starches, microcrystalline cellulose, lactose, sucrose, glucose, mannitol, and/or silicic acid; binders, such as carboxymethylcellulose, alginates, gelatin, polyvinyl pyrrolidone, sucrose and/or acacia; humectants, such as glycerol; disintegrating agents, such as croscarmellose sodium, agar-agar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof; coloring agents; buffering agents; release agents; coating agents; sweetening, flavoring and perfuming agents; and preservatives and antioxidants.

Representative coating agents for tablets, capsules, pills and like, include those used for enteric coatings, such as cellulose acetate phthalate, polyvinyl acetate phthalate, hydroxypropyl methylcellulose phthalate, methacrylic acid-methacrylic acid ester copolymers, cellulose acetate trimellitate, carboxymethyl ethyl cellulose, hydroxypropyl methyl cellulose acetate succinate, polyvinyl acohol and the like.

Representative antioxidants include: water-soluble antioxidants, such as ascorbic acid, cysteine hydrochloride, sodium bisulfate, sodium metabisulfate, sodium sulfite, and the like; oil-soluble antioxidants, such as ascorbyl palmitate, butylated hydroxyanisole, butylated hydroxytoluene, lecithin, propyl gallate, alpha-tocopherol, and the like; and metal-chelating agents, such as citric acid, ethylenediamine tetraacetic acid, sorbitol, tartaric acid, phosphoric acid, and the like.

Pharmaceutical compositions may also be formulated to provide slow or controlled-release of the active agent using, by way of example, hydroxypropyl methyl cellulose in varying proportions or other polymer matrices, liposomes and/or microspheres. In addition, the pharmaceutical composition may contain opacifying agents and may be formulated so that they release the active agent only, or preferentially, in a certain portion of the gastrointestinal tract, optionally, in a delayed manner. Examples of embedding compositions which can be used include polymeric substances and waxes. The active agent can also be in microencapsulated form, if appropriate, with one or more of the above-described excipients.

Suitable liquid dosage forms for oral administration include, by way of example, pharmaceutically-acceptable emulsions, microemulsions, solutions, suspensions, syrups and elixirs. Liquid dosage forms typically comprise the active agent and an inert diluent, such as, for example, water, juice or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (e.g., cottonseed, groundnut, corn, germ, olive, castor and sesame oils), glycerol, tetrahydrofuryl alcohol, polyethylene glycols and fatty acid esters of sorbitan, and mixtures thereof. Suspensions may contain suspending agents such as, for example, ethoxylated isostearyl alcohols, polyoxyethylene sorbitol and sorbitan esters, microcrystalline cellulose, aluminium metahydroxide, bentonite, agar-agar and tragacanth, and mixtures thereof.

In one embodiment, the pharmaceutical composition is suitable for rectal administration. Pharmaceutical compositions for rectal administration may be in the form of, for example, suppositories, solutions (for enemas), gels, creams, and the like.

By way of illustration, representative pharmaceutical compositions can be prepared as described in the following examples.

A. Hard Gelatin Capsules

The active agent (10 g), spray-dried lactose (480 g) and magnesium stearate (10 g) are thoroughly blended. The resulting composition is then loaded into hard gelatin capsules (500 mg of composition per capsule). Each capsule provides 10 mg of the active agent per unit dose suitable for oral administration.

B. Hard Gelatin Capsules

The active agent (8 g) is thoroughly blended with starch (95 g), microcrystalline cellulose (95 g) and magnesium stearate (2 g). The mixture is then passed through a No. 45 mesh U.S. sieve and loaded into hard gelatin capsules (200 mg of composition per capsule). Each capsule provides 8 mg of the active agent per unit dose suitable for oral administration.

C. Soft Gelatin Capsules

The active agent (5 g) is thoroughly blended with polyoxyethylene sorbitan monooleate (65 g) and starch powder (335 g). The mixture is then loaded into soft gelatin capsules (400 mg of composition per capsule). Each capsule provides 5 mg of the active agent per unit dose suitable for oral administration.

D. Soft Gelatin Capsules

The active agent (10 g) is thoroughly blended with microcrystalline cellulose (281 g) and magnesium stearate (9 g). The mixture is then loaded into soft gelatin capsules (300 mg of composition per capsule). Each capsule provides 10 mg of the active agent per unit dose suitable for oral administration.

E. Tablets

The active agent (10 g), starch (45 g) and microcrystalline cellulose (35 g) are passed through a No. 20 mesh U.S. sieve and mixed thoroughly. The resulting granules are dried at 50-60° C. and passed through a No. 16 mesh U.S. sieve. Separately, a solution of polyvinylpyrrolidone (4 g as a 10% solution in sterile water) is mixed with sodium carboxymethyl starch (4.5 g), magnesium stearate (0.5 g) and talc (1 g), and this mixture is passed through a No. 16 mesh U.S. sieve. The resulting mixture is then added to the granules. After mixing thoroughly, the mixture is compressed on a tablet press to form tablets weighing 100 mg each. Each tablet provides 10 mg of the active agent per unit dose suitable for oral administration.

F. Tablets

The active agent (40 g) is thoroughly blended with microcrystalline cellulose (445 g), silicon dioxide fumed (10 g), and stearic acid (5 g). The mixture is then compressed on a tablet press to form tablets weighing 100 mg each. Each tablet provides 8 mg of the active agent per unit dose suitable for oral administration.

G. Tablets

The active agent (10 g) is thoroughly blended with cornstarch (50 g), croscarmellose sodium (25 g), lactose (110 mg), and magnesium stearate (5 mg). The mixture is then compressed on a tablet press to form tablets weighting 200 mg each. Each tablet provides 10 mg of the active agent per unit dose suitable for oral administration.

H. Tablets

The active agent (10 g) is thoroughly blended with cornstarch (230 g) and an aqueous solution of gelatin (50 g). The mixture is dried and ground to a fine powder. Microcrystalline cellulose (100 g) and magnesium stearate (10 g) are then admixed with the gelatin formulation, granulated and the resulting mixture compressed on a tablet press to form tablets weighing 200 mg each. Each tablet provides 5 mg of the active agent per unit dose suitable for oral administration.

I. Syrup

The following ingredients are thoroughly mixed until all the solid ingredients are dissolved:

| Ingredients | Amount |
| --- | --- |
| Active Agent | 0.5 g |
| Citric acid | 2.1 g |
| Artificial Raspberry Favor | 2.0 mL |
| Methyl Paraben | 2.0 g |
| Propyl Paraben | 0.5 g |
| Sorbitol Solution USP (64% solution), to make | 1000.0 mL |

The resulting syrup contains 5 mg of active agent per 10 mL of syrup suitable for oral administration.

Co-Administration and Combinations

If desired, the compounds of the present invention may be administered in combination with one or more other therapeutic agents (also referred to herein as "secondary agents"). For example, the compounds of the present invention may be administered with other therapeutic agents that are used to treat gastrointestinal inflammatory diseases or other gastrointestinal conditions. Additionally, the compounds of the present invention may be administered with other therapeutic agents that cause gastrointestinal inflammation, such as cytotoxic T lymphocyte associated antigen 4 (CTLA-4) inhibitors, programmed cell death 1 (PD-1) inhibitors, and programmed death ligand 1 (PD-L1) inhibitors, to treat the inflammation caused by such agents.

Representative classes of therapeutic agents that can be administered in combination with compounds of the present invention include, by way of example, aminosalicylates, steroids, systemic immunosuppressants, anti-TNFα antibodies, anti-alpha4 (anti-VLA-4) antibodies, anti-integrin $\alpha 4\beta_7$ antibodies, anti-bacterial agents, anti-diarrheal medicines, cytotoxic T lymphocyte associated antigen 4 (CTLA-4) inhibitors; programmed cell death 1 (PD-1) inhibitors, and programmed death ligand 1 (PD-L1) inhibitors; or combinations thereof. Those skilled in the art will understand that the terms "aminosalicylate," "steroid," "systemic immunosuppressant," "anti-TNFα antibody," "anti-alpha4 (anti-VLA-4) antibody," "anti-integrin $\alpha_4\beta_7$ antibody," "anti-bacterial agent," "anti-diarrheal medicine," "cytotoxic T lymphocyte associated antigen 4 (CTLA-4) inhibitors," "programmed cell death 1 (PD-1) inhibitors," and "programmed death ligand 1 (PD-L1) inhibitors" (or specific examples of compounds in such classes) include all forms of such compounds including, for example, pharmaceutically-acceptable salts, solvates, crystalline forms, polymorphs, prodrugs and the like. Similarly, the term "secondary agent" as used herein includes all forms of the secondary agent, such as pharmaceutically-acceptable salts, solvates, crystalline forms, polymorphs, prodrugs and the like.

Representative examples of aminosalicylates include, but are not limited to, mesalamine, olsalazine and sulfasalazine, and the like.

Representative examples of steroids include, but are not limited to, prednisone, prednisolone, hydrocortisone, budesonide, beclomethasone, fluticasone, and the like.

Representative examples of systemic immunosuppressants include, but are not limited to, cyclosporine, azathioprine, methotrexate, 6-mercaptopurine, tacrolimus, and the like.

Representative examples of anti-TNFα antibodies include, but are not limited to, infliximab, adalimumab, golimumab, certolizumab, and the like.

Representative examples of cytotoxic T lymphocyte associated antigen 4 (CTLA-4) inhibitors include, but are not limited to, ipilimumab, tremelimumab and the like.

Representative examples of programmed cell death 1 (PD-1) inhibitors include, but are not limited to, pembrolizumab, nivolumab and the like.

Representative examples of programmed death ligand 1 (PD-L1) inhibitors include, but are not limited to, atezolizumab, durvalumab, avelumab and the like.

Other secondary agents include anti-alpha4 antibodies, such as natalizumab; anti-integrin $\alpha_4\beta_7$ antibodies, such as vedolizumab; anti-bacterial agents, such as rifaximin; and anti-diarrheal medicines, such as loperamide. Such secondary agents and their use are well-known in the art. See, for example, Mozaffari et al. *Expert Opin. Biol. Ther.* 2014, 14, 583-600; Danese, Gut, 2012, 61, 918-932; and Lam et al., *Immunotherapy,* 2014, 6, 963-971.

A compound of the present invention and the secondary agent may be either physically mixed to form a composition containing both agents; or each agent may be administered separately to the patient, either simultaneously or sequentially. For example, a compound of the present invention can be combined with a secondary agent using conventional procedures and equipment to form a combination of agents comprising, e.g., a compound of formula I and a secondary agent. Additionally, the agents may be combined with a pharmaceutically-acceptable carrier to form a pharmaceutical composition comprising a compound of formula I, a secondary agent and a pharmaceutically-acceptable carrier. In this embodiment, the components of the composition are typically mixed or blended to create a physical mixture. The physical mixture is then administered to the patient by any suitable route of administration, such as oral administration.

Alternatively, the agents may remain separate and distinct before administration to the patient. In this embodiment, the agents are not physically mixed together before administration but are administered simultaneously or at separate times as separate compositions. Such compositions can be packaged separately or may be packaged together in a kit. When administered at separate times, the secondary agent will typically be administered less than 24 hours after administration of a compound of the present invention, e.g., ranging anywhere from concurrent administration to about 24 hours post-dose. This is also referred to as sequential administration. Thus, for example, a compound of the present invention can be orally administered simultaneously or sequentially with a secondary agent using two tablets (e.g., one tablet for each active agent), where sequential includes being administered immediately before or after administration of the compound of the present invention or at some other time (e.g., one hour before or after; or three hours before or after, etc.). Alternatively, the combination may be administered by different routes of administration, e.g., one orally and the other parenterally.

When employed in the present invention, the secondary agent is used in a therapeutically effective amount, i.e., in an amount that produces a therapeutically beneficial effect when co-administered with a compound of the present invention. For example, such secondary agents are typically employed in their approved dosage amounts.

Accordingly, in one aspect, the present invention relates to a pharmaceutical composition comprising:

(a) a compound of formula I, II, III, IV, V, VI or VII (or a specific embodiment thereof), or a pharmaceutically-acceptable salt thereof;

(b) a secondary agent selected from an aminosalicylate, steroid, systemic immunosuppressant, anti-TNFα antibody, anti-alpha4 (anti-VLA-4) antibody, anti-integrin $\alpha_4\beta_7$ antibody, anti-bacterial agent, anti-diarrheal medicine, cytotoxic T lymphocyte associated antigen 4 (CTLA-4) inhibitor, programmed cell death 1 (PD-1) inhibitor, and programmed death ligand 1 (PD-L1) inhibitor; or a combinations thereof; and (c) a pharmaceutically-acceptable carrier.

In another aspect, the present invention relates to a method of treating a gastrointestinal inflammatory disease in a mammal, the method comprising administering to the mammal:

(a) a pharmaceutical composition comprising a pharmaceutically-acceptable carrier and a compound of formula I, II, III, IV, V, VI or VII (or a specific embodiment thereof), or a pharmaceutically-acceptable salt thereof; and (b) a pharmaceutical composition comprising a pharmaceutically-acceptable carrier and a secondary agent selected from an aminosalicylate, steroid, systemic immunosuppressant, anti-TNFα antibody, anti-alpha4 (anti-VLA-4) antibody, anti-integrin $\alpha_4\beta_7$ antibody, anti-bacterial agent, anti-diarrheal medicine, cytotoxic T lymphocyte associated antigen 4 (CTLA-4) inhibitor, programmed cell death 1 (PD-1) inhibitor, and programmed death ligand 1 (PD-L1) inhibitor;

wherein (a) and (b) are administered either simultaneously or sequentially.

In a particular embodiment, the present invention relates to a method of treating colitis associated with immune checkpoint inhibitor therapy. In this embodiment, a compound of the present invention is administered in combination with the immune checkpoint inhibitor to treat the gastrointestinal inflammation caused by the immune checkpoint inhibitor. In a particular embodiment, the compound of the present invention is administered prophylactically to prevent the onset of colitis.

Accordingly, in one aspect, the present invention relates to a method of treating colitis associated with immune checkpoint inhibitor therapy in a patient, the method comprising administering to the patient:

(a) a pharmaceutical composition comprising a pharmaceutically-acceptable carrier and a compound of formula I, II, III, IV, V, VI or VII (or a specific embodiment thereof), or a pharmaceutically-acceptable salt thereof; and (b) a pharmaceutical composition comprising a pharmaceutically-acceptable carrier and an immune checkpoint inhibitor;

wherein (a) and (b) are administered either simultaneously or sequentially.

In one embodiment, the immune checkpoint inhibitor is a cytotoxic T lymphocyte associated antigen 4 (CTLA-4) inhibitor. In another embodiment, the immune checkpoint inhibitor is a programmed cell death 1 (PD-1) inhibitor. In yet another embodiment, the immune checkpoint inhibitor is a programmed death ligand 1 (PD-L1) inhibitor.

Utility

The compounds of the present invention are expected to be useful for the treatment of gastrointestinal inflammatory diseases, such as ulcerative colitis, Crohn's disease, colitis associated with immune checkpoint inhibitor therapy, microscopic colitis (including collagenous colitis and lymphocytic colitis), pouchitis and the like. The compounds are also expected to be useful for the treatment of autoimmune conditions in the gastrointestinal track, such as graft versus host disease, celiac sprue, autoimmune enteropathy and the like.

The compounds of the present invention have various properties that may make them particularly useful for treating gastrointestinal diseases or conditions. In particular, the glucuronide prodrug moiety of the present compounds is designed to be cleaved by the abundance of bacterial β-glucuronide enzyme in the gastrointestinal tract to release the JAK inhibitor predominately in the gastrointestinal tract (e.g., at the site of gastrointestinal inflammation). Additionally, the glucuronide prodrug compounds of the present invention are expected to be poorly absorbed systemically, thus minimizing the risk of immunosuppression outside of the gastrointestinal tract.

As described in the experimental section below, compounds of the present invention have been profiled in various preclinical assays. For example, representative glucuronide prodrug compounds have been shown to have a half-life of less than about 5 minutes in rat colon fecal homogenate (see Example 41). Moreover, representative glucuronide prodrug compounds have been shown to produce significantly higher JAK inhibitor exposure ($AUC_{0-6 hr}$) in colon tissue compared to plasma following oral administration of the glucuronide prodrug compound to mice (see Example 42).

Accordingly, the compounds of the present invention are expected to be useful for the treatment of gastrointestinal inflammatory diseases.

In one embodiment, a compound of the present invention is used to treat ulcerative colitis in a human patient. In one embodiment, the compound of the present invention is used for inductive therapy for ulcerative colitis (e.g., to treat acute symptoms and to promote mucosal healing). In another embodiment, the compound of the present invention is used for maintenance therapy for ulcerative colitis (e.g., to maintain remission).

In another embodiment, a compound of the present invention is used to treat Crohn's disease in a human patient.

In yet another embodiment, a compound of the present invention is used to treat colitis associated with or induced by immune checkpoint inhibitor therapy (i.e., immune checkpoint inhibitor-induced colitis or ICI-IC).

When used to treat a gastrointestinal inflammatory disease, a compound of the present invention is typically administered to the patient in a therapeutically-effective amount. In one embodiment, a compound of the present invention is administered to a patient in need of treatment in an amount ranging from about 0.5 mg to about 50 mg per day; or as needed. In another embodiment, the amount administered to the patient ranges from about 1 mg to about 40 mg per day, including about 1 to about 20 mg per day. The amount administered to the patient, the route of administration and the frequency of administration will typically be determined by the physician treating the patient.

In one embodiment, the compound of the present invention is used to maintain remission of the gastrointestinal inflammatory disease following treatment of the acute symptoms.

The compound of the present invention may be administered to the patient by any acceptable route of administration including, for example, oral and rectal modes of administration.

In one embodiment, a compound of the present invention is administered to the patient orally in a solid or liquid dosage form. In a particular embodiment, the form administered to the patient is a solid dosage form including a tablet or capsule. In another particular embodiment, the form administered to the patient is a liquid dosage form including a solution, syrup, suspension or emulsion.

A compound of the present invention may be administered to the patient in a single daily dose (e.g., once a day); in multiple doses per day (e.g., twice, three times or four times daily); or in multiple doses per week (e.g., twice, three times, four times, five times or six times per week). In a particular embodiment, the compound of the present invention is administered to the patient once per day.

EXAMPLES

The following examples are provided to illustrate various representative embodiments and aspects of this invention, and as such, they are not intended to limit the scope of this invention unless specifically indicated.

The following abbreviations have the following meanings unless otherwise indicated:

ACN=acetonitrile
d=day(s)
DCM=dichloromethane
DIPEA=N,N-diisopropylethylamine
DMAP=4-dimethylaminopyridine
EtOAc=ethyl acetate
EtOH=ethanol
h=hour(s)
IPA=isopropyl alcohol
MeOH=methanol
min=minute(s)
TFA=trifluoroacetic acid
THF=tetrahydrofuran Reagents and solvents were purchased from commercial suppliers (such as Sigma-Aldrich, St. Louis, Mo. and its affiliates) and were used without further purification unless otherwise indicated.

In these experimental procedures, reaction progress is typically monitored by thin layer chromatography (TLC), analytical high performance liquid chromatography (analytical HPLC), or mass spectrometry. Additionally, reaction mixtures are typically purified by column chromatography, preparative HPLC or UPLC, typically using C18 or base-deactivated silica (BDS) column packing materials and conventional eluents. The internal standard used for LC-MS and other analytical assays is (R)-3-(1-((3'-chloro-[1,1'-biphenyl]-4-yl)methyl)-2-(3-hydroxyisoxazole-5-carbonyl) hydrazinyl)-2-hydroxypropanoic acid.

Representative preparative HPLC conditions are as follows:

A. Preparative HPLC Conditions

| Column | C18, 5 μm. 21.2 × 150 mm; or |
| --- | --- |
|  | C18, 5 μm 21 × 250 mm; or |
|  | C14, 5 μm 21 × 150 mm |
| Column Temperature | Room Temperature |
| Flow Rate | 20.0 mL/min |
| Mobile Phases | A = Water + 0.05% TFA |
|  | B = ACN + 0.05% TFA |
| Injection Volume | 100-1500 μL |
| Detector Wavelength | 214 nm |

The crude material is dissolved in 1:1 water/acetic acid at about 50 mg/mL. A 4 min. analytical scale test run is carried out using a 2.1×50 mm C18 column followed by a 15 or 20 minute preparative scale run using 100 μL injection with the gradient based on the % B retention of the analytical scale test run. Exact gradients are sample dependent. Samples with close running impurities are checked with a 21×250 mm C18 column and/or a 21×150 mm C14 column for best separation. Fractions containing desired product are identified by mass spectrometric analysis.

Reaction products are typically characterized by analytical HPLC or UPLC and mass spectrometry. For example, mass spectral identification of compounds is typically done using an electrospray ionization method (ESMS) on an Applied Biosystems Model API 150 EX instrument (Foster City, Calif.) or a Waters 3100 instrument (Milford, Mass.), coupled to autopurification systems.

Representative analytical HPLC and UPLC-MS conditions are as follows:

B. Analytical HPLC Conditions—Method A

| Instrument | Agilent 1260 HPLC |
| --- | --- |
| Column | LUNA C18 (2); 150 × 4.60 mm; 3 micron |
| Column Temperature | 35° C. |
| Flow Rate | 1.2 mL/min |
| Injection Volume | 5 μL |
| Sample Preparation | Dissolve in 1:1 ACN:water to about |
|  | 0.5 mg/mL solution |
| Mobile Phases | A = Water:ACN:TFA (98:2:0.05) |
|  | B = Water:ACN:TFA (30:70:0.05) |
| Detector Wavelength | 230 nm |
| Gradient | 28 min total |
|  | Time (min)/% |
|  | B: 0/10, 20/100, 22/100, 23/10, 28/10 |

C. Analytical HPLC Conditions—Method B

| Instrument | Agilent 1260 HPLC |
| --- | --- |
| Column | Zorbax-Bonus RP C14; 30 × 2.1 mm; 1.8 micron |
| Column Temperature | 60° C. |
| Flow Rate | 1.2 mL/min |
| Injection Volume | 3 μL |
| Sample Preparation | Dissolve in 1:1 ACN:water to about |
|  | 1.0 mg/mL solution |
| Mobile Phases | A = Water:TFA (99.9%:0.1%) |
|  | B = ACN:TFA (99.9%:0.1%) |
| Detector Wavelength | 214 nm |
| Gradient | 3.0 min total |
|  | Time (min)/% |
|  | B: 0/5, 1.5/65, 1.8/95, 2.1/95, 2.5/5, 3.0/5 |

D. UPLC-MS Analysis Conditions

| Column | Acquity BEH C-18 (2.1 × 100 mm, 1.7 μm) | |
| --- | --- | --- |
| Column Temperature | 30° C. | |
| Flow Rate | 0.3 mL/min | |
| Mobile Phases | A = 5 mM Ammonium Acetate in Water | |
|  | B = ACN | |
| Detector Wavelength | 214 nm | |
| Gradient | Time (min) | A | B |
|  | 0 | 90.0 | 10.0 |
|  | 1.0 | 90.0 | 10.0 |
|  | 2.0 | 85.0 | 15.0 |
|  | 4.5 | 45.0 | 55.0 |
|  | 6.0 | 10.0 | 90.0 |
|  | 8.0 | 10.0 | 90.0 |
|  | 9.0 | 90.0 | 10.0 |
|  | 10.0 | 90.0 | 10.0 |

Example 1

Preparation of (2R,3R,4S,5S,6S)-2-Bromo-6-(methoxycarbonyl)tetrahydro-2H-pyran-3,4,5-triyl Triacetate

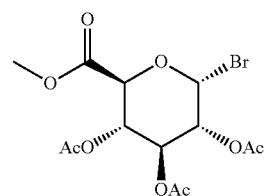 [SMILES: COC(=O)[C@H]1O[C@H](Br)[C@H](OC(C)=O)[C@@H](OC(C)=O)[C@@H]1OC(C)=O]

To an ice-cold solution of 1,2,3,4-tetra-O-acetyl-β-D-gluocuronide methyl ester (50 g, 132.80 mmol) in DCM (600 mL) was added titanium bromide (50.20 g, 136.80 mmol). The resulting mixture was allowed to warm to room temperature and stirring was continued for 8 h (reaction complete by TLC monitoring). The reaction mixture was then diluted with ice-cold water (500 mL) and the organic layer was extracted with DCM (2×500 mL). The combined organic extracts were dried over sodium sulfate, filtered and concentrated under reduced pressure to afford the title compound (50 g, 95%) as a pale-yellow solid that was used without further purification.

Example 2

Preparation of (2S,3R,4S,5S,6S)-2-(4-((((2-(4-(1-((R)-2-Cyano-1-cyclopentylethyl)-1H-pyrazol-4-yl)-N-methyl-7H-pyrrolo[2,3-d]pyrimidine-7-carboxamido)ethyl)(methyl)-carbamoyl)oxy)methyl)-2-nitrophenoxy)-6-(methoxycarbonyl)tetrahydro-2H-pyran-3,4,5-triyl Triacetate (Compound VII-1)

Step 2-1—Preparation of (2S,3R,4S,5S,6S)-2-(4-Formyl-2-nitrophenoxy)-6-(methoxycarbonyl)tetrahydro-2H-pyran-3,4,5-triyl Triacetate

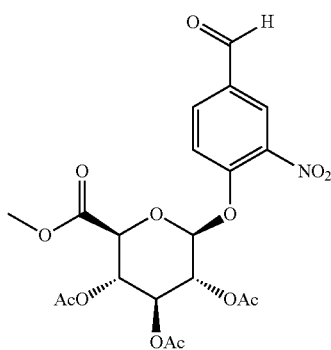 [SMILES: COC(=O)[C@H]1O[C@@H](Oc2ccc(C=O)cc2[N+](=O)[O-])[C@H](OC(C)=O)[C@@H](OC(C)=O)[C@@H]1OC(C)=O]

To an ice cold solution of (2R,3R,4S,5S,6S)-2-bromo-6-(methoxycarbonyl)tetrahydro-2H-pyran-3,4,5-triyl triacetate (50.0 g, 125.9 mmol) in ACN (600 mL) was added silver oxide (32.1 g, 138.5 mmol) followed by addition of 4-hydroxy-3-nitrobenzaldehyde (23.1 g, 138.5 mmol) at 0° C. The resulting mixture was stirred at room temperature for 6 h (reaction complete by TLC monitoring). The reaction mixture was then filtered through diatomaceous earth and the filtrate was concentrated under reduced pressure. The crude residue was purified by column chromatography (100-200 mesh, 30% EtOAc:Hexane) to afford the title compound (54.0 g, 89%) as pale yellow solid.

Step 2-2—Preparation of (2S,3R,4S,5S,6S)-2-(4-(Hydroxymethyl)-2-nitrophenoxy)-6-(methoxycarbonyl)tetrahydro-2H-pyran-3,4,5-triyl Triacetate

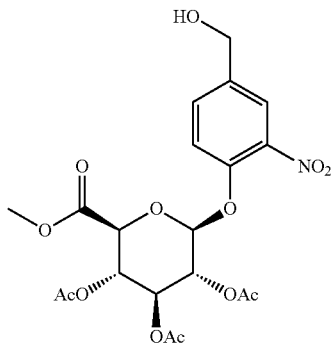 [SMILES: COC(=O)[C@H]1O[C@@H](Oc2ccc(CO)cc2[N+](=O)[O-])[C@H](OC(C)=O)[C@@H](OC(C)=O)[C@@H]1OC(C)=O]

To an ice cold solution of (2S,3R,4S,5S,6S)-2-(4-formyl-2-nitrophenoxy)-6-(methoxycarbonyl)tetrahydro-2H-pyran-3,4,5-triyl triacetate (52.0 g, 107.7 mmol) and silica gel (80 g) in IPA/chloroform (1 L, 3:7) was added sodium borohydride (11.0 g, 290.7 mmol); followed by addition of triethylamine (1.60 mL, 11.77 mmol). The reaction mixture was stirred at 0° C. for 2 h (reaction complete by TLC monitoring). The reaction mixture was then quenched with ice water and the resulting mixture was filtered. The filtrate was concentrated under reduced pressure and the crude residue was crystallized using ethanol. The resulting solid was isolated by filtration and then dried under reduced pressure to afford the title compound (40.0 g, 77%) as off white solid.

Step 2-3—Preparation of (2S,3S,4S,5R,6S)-2-(Methoxycarbonyl)-6-(4-(((methyl(2-(methylamino)ethyl)carbamoyl)oxy)methyl)-2-nitrophenoxy)tetrahydro-2H-pyran-3,4,5-triyl Triacetate

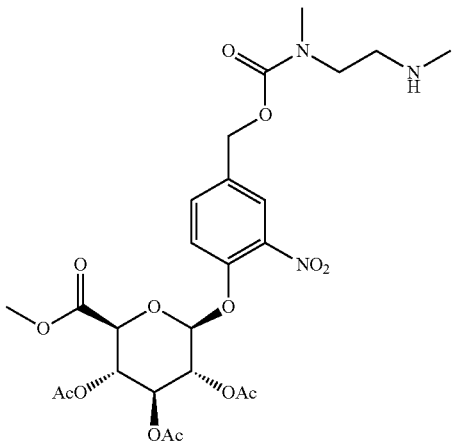

To an ice cold stirred solution of (2S,3R,4S,5S,6S)-2-(4-(hydroxymethyl)-2-nitrophenoxy)-6-(methoxycarbonyl)tetrahydro-2H-pyran-3,4,5-triyl triacetate (10.0 g, 20.60 mmol) in DCM (200 ml) was added triethylamine (8.6 mL, 61.74 mmol) dropwise. After 15 minutes of stirring at 0° C., p-nitrophenyl chloroformate (9.0 g, 41.18 mmol, dissolved in 50 mL of DCM) was added in dropwise manner. The resulting mixture was stirred for 2 h at room temperature (reaction complete by TLC monitoring). The resulting mixture was cooled to 0° C. and $N^1,N^2$-dimethylethane-1,2-diamine (10.2 ml, 102.2 mmol) was added in a dropwise manner. The resulting mixture was stirred for 30 min (reaction complete by TLC monitoring). The reaction mixture was then concentrated under reduced pressure and the crude residue was purified by column chromatography on silica gel (60-120 mesh) using 10% MeOH in DCM as eluent to provide the title compound (3.40 g; 30%).

Step 2-4—Preparation of (2S,3R,4S,5S,6S)-2-(4-((((2-((Chlorocarbonyl)-(methyl)amino)ethyl)-(methyl)carbamoyl)oxy)methyl)-2-nitrophenoxy)-6-(methoxycarbonyl)tetrahydro-2H-pyran-3,4,5-triyl Triacetate

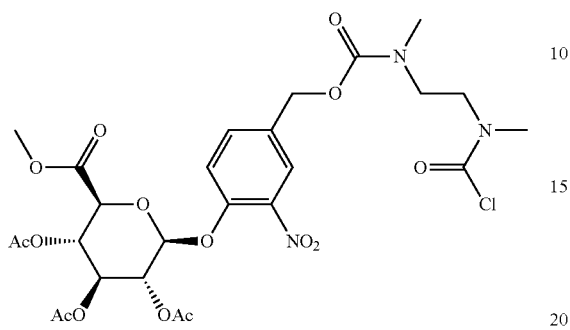

To a stirred solution of (2S,3S,4S,5R,6S)-2-(methoxycarbonyl)-6-(4-(((methyl(2-(methylamino)ethyl)carbamoyl)oxy)methyl)-2-nitrophenoxy)tetrahydro-2H-pyran-3,4,5-triyl triacetate (3.7 g, 6.17 mmol) in DCM (50 mL) was added triethylamine (2.5 mL, 18.52 mmol) at 0° C.; followed by the addition of phosgene (3.10 mL, 6.17 mmol, 20% solution in toluene). The resulting mixture was then stirred at room temperature for 5 h under nitrogen atmosphere (reaction complete by TLC monitoring). The reaction mixture was then evaporated under reduced pressure and the crude residue was purified by column chromatography on silica gel (60-120 mesh) using EtOAc as eluent to provide the title compound (3.00 g; 70%).

Step 2-5—Preparation of (2S,3R,4S,5S,6S)-2-(4-(((((2-(4-(1-((R)-2-Cyano-1-cyclopentylethyl)-1H-pyrazol-4-yl)-N-methyl-7H-pyrrolo[2,3-d]pyrimidine-7-carboxamido)ethyl)(methyl)-carbamoyl)oxy)methyl)-2-nitrophenoxy)-6-(methoxycarbonyl)tetrahydro-2H-pyran-3,4,5-triyl Triacetate

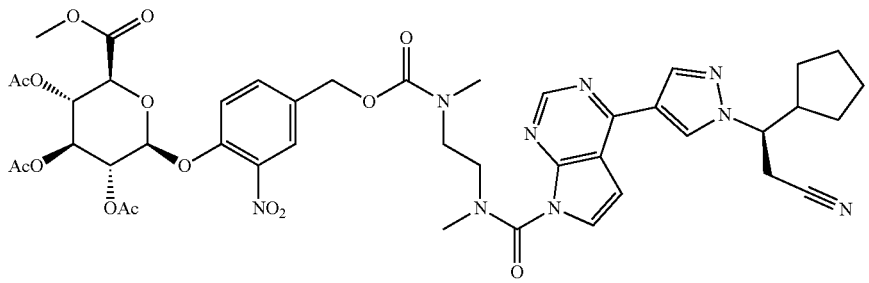 [SMILES: COC(=O)[C@H]1O[C@@H](Oc2ccc(COC(=O)N(C)CCN(C)C(=O)n3ccc4c(-c5cnn([C@H](CC#N)C6CCCC6)c5)ncnc43)cc2[N+](=O)[O-])[C@H](OC(C)=O)[C@@H](OC(C)=O)[C@@H]1OC(C)=O]

To solution of (2S,3R,4S,5S,6S)-2-(4-((((2-((chlorocarbonyl)(methyl)amino)-ethyl)-(methyl)carbamoyl)oxy)methyl)-2-nitrophenoxy)-6-(methoxycarbonyl)tetrahydro-2H-pyran-3,4,5-triyl triacetate (3.0 g, 4.53 mmol) in DCM (50 mL) was added triethylamine (1.90 mL, 13.59 mmol) and DMAP (3.3 g, 27.19) at 0° C.; followed by ruxolitinib (971 mg, 3.17 mmol). The resulting mixture was stirred at room temperature for 16 h (reaction complete by TLC monitoring). The reaction mixture was then evaporated under reduced pressure and the crude residue was purified by column chromatography on silica gel (60-120 mesh) using 2% MeOH in DCM as eluent to provide the title compound (1.50 g, 30%) as an off-white solid.

Step 2-6—Preparation of (2S,3S,4S,5R,6S)-6-(4-((((2-(4-(1-((R)-2-Cyano-1-cyclopentylethyl)-1H-pyrazol-4-yl)-N-methyl-7H-pyrrolo[2,3-d]pyrimidine-7-carboxamido)ethyl)-(methyl)carbamoyl)oxy)methyl)-2-nitrophenoxy)-3,4,5-trihydroxytetrahydro-2H-pyran-2-carboxylic Acid (Compound VII-1)

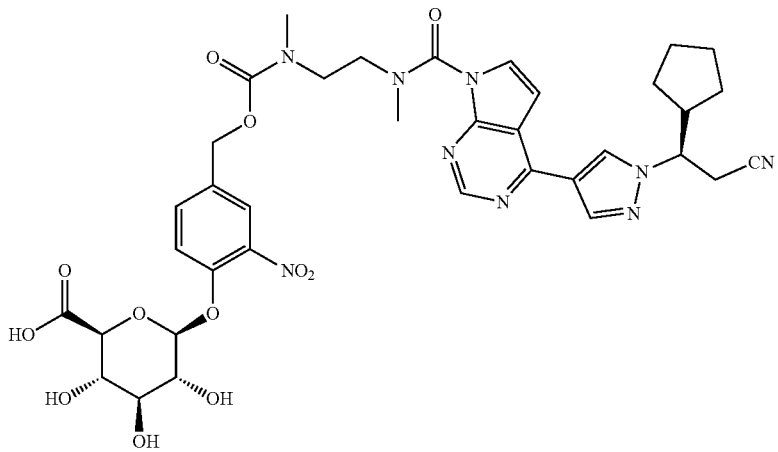 [SMILES: CN(CCN(C)C(=O)n1ccc2c(-c3cnn([C@H](CC#N)C4CCCC4)c3)ncnc21)C(=O)OCc1ccc(O[C@@H]2O[C@H](C(=O)O)[C@@H](O)[C@H](O)[C@H]2O)c([N+](=O)[O-])c1]

To a stirred solution of (2S,3R,4S,5S,6S)-2-(4-((((2-(4-(1-((R)-2-cyano-1-cyclopentylethyl)-1H-pyrazol-4-yl)-N-methyl-7H-pyrrolo[2,3-d]pyrimidine-7-carboxamido)ethyl)(methyl)-carbamoyl)oxy)methyl)-2-nitrophenoxy)-6-(methoxycarbonyl)tetrahydro-2H-pyran-3,4,5-triyl triacetate (1.5 g, 1.60 mmol) in MeOH (80 mL) and water (15 mL) was added DIPEA (8 mL) at 0° C. The resulting mixture was stirred at 0° C. for 16 h (reaction complete by TLC and LCMS monitoring). The reaction mixture was then evaporated under reduced pressure and the crude residue was purified by RP-HPLC to provide the title compound (490 mg, 37%) as an off-white solid. MS (m/z): [M+H]$^+$ calcd for $C_{36}H_{41}N_9O_{12}$, 792.29; found, 792.4.

Example 3

Preparation of (2S,3S,4S,5R,6S)-6-(4-((((2-(4-(1-(3-(Cyanomethyl)-1-(ethylsulfonyl)azetidin-3-yl)-1H-pyrazol-4-yl)-N-methyl-7H-pyrrolo[2,3-d]pyrimidine-7-carboxamido)ethyl)-(methyl)carbamoyl)oxy)methyl)-2-nitrophenoxy)-3,4,5-trihydroxytetrahydro-2H-pyran-2-carboxylic Acid (Compound VII-2)

Step 3-1—Preparation of (2S,3R,4S,5S,6S)-2-(4-((((2-(4-(1-(3-(Cyanomethyl)-1-(ethylsulfonyl)azetidin-3-yl)-1H-pyrazol-4-yl)-N-methyl-7H-pyrrolo[2,3-d]pyrimidine-7-carboxamido)ethyl)-(methyl)carbamoyl)oxy)methyl)-2-nitrophenoxy)-6-(methoxycarbonyl)tetrahydro-2H-pyran-3,4,5-triyl Triacetate

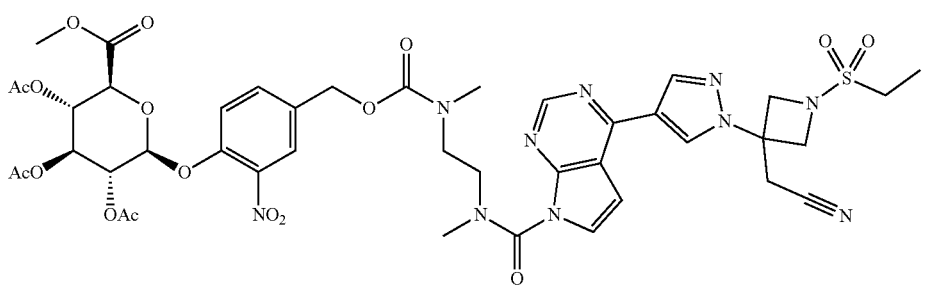 [SMILES: CCS(=O)(=O)N1CC(CC#N)(n2cc(-c3ncnc4c3ccn4C(=O)N(C)CCN(C)C(=O)OCc3ccc(O[C@@H]4O[C@H](C(=O)OC)[C@@H](OC(C)=O)[C@H](OC(C)=O)[C@H]4OC(C)=O)c([N+](=O)[O-])c3)cn2)C1]

To an ice cold solution of (2S,3R,4S,5S,6S)-2-(4-((((2-((chlorocarbonyl)(methyl)-amino)ethyl)(methyl)carbamoyl)oxy)methyl)-2-nitrophenoxy)-6-(methoxycarbonyl)tetrahydro-2H-pyran-3,4,5-triyl triacetate (1.40 g, 2.11 mmol) in DCM (50 mL) was added triethylamine (0.88 mL, 6.33 mmol) and DMAP (1.50 g, 12.66) followed by baricitinib (549 mg, 1.48 mmol). The resulting mixture was stirred for 16 h (reaction complete by TLC monitoring). The solvent was then evaporated under reduced pressure and the crude product was purified by column chromatography on silica gel (100-200 mesh) using 2% MeOH in DCM as eluent to provide the title compound (950 mg, 45%).

Step 3-2—Preparation of (2S,3S,4S,5R,6S)-6-(4-((((2-(4-(1-(3-(Cyanomethyl)-1-(ethylsulfonyl)azetidin-3-yl)-1H-pyrazol-4-yl)-N-methyl-7H-pyrrolo[2,3-d]pyrimidine-7-carboxamido)ethyl)-(methyl)carbamoyl)oxy)methyl)-2-nitrophenoxy)-3,4,5-trihydroxytetrahydro-2H-pyran-2-carboxylic Acid (Compound VII-2)

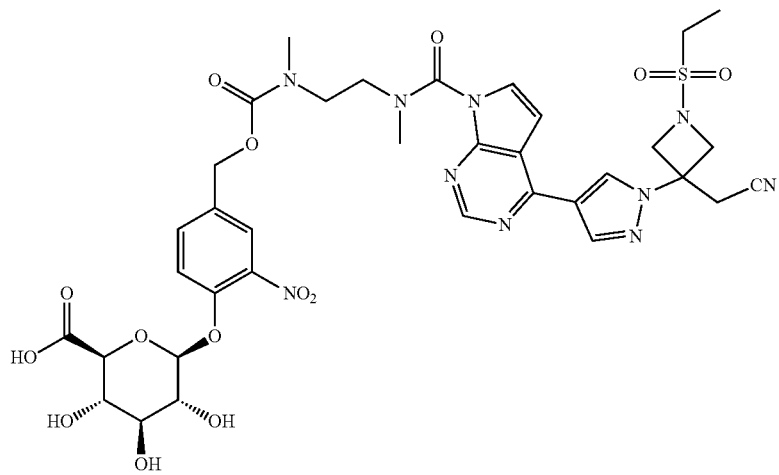 [SMILES: CCS(=O)(=O)N1CC(CC#N)(n2cc(-c3ncnc4c3ccn4C(=O)N(C)CCN(C)C(=O)OCc3ccc(O[C@@H]4O[C@H](C(=O)O)[C@@H](O)[C@H](O)[C@H]4O)c([N+](=O)[O-])c3)cn2)C1]

To an ice-cold solution of (2S,3R,4S,5S,6S)-2-(4-((((2-(4-(1-(3-(cyanomethyl)-1-(ethylsulfonyl)azetidin-3-yl)-1H-pyrazol-4-yl)-N-methyl-7H-pyrrolo[2,3-d]pyrimidine-7-carboxamido)ethyl)-(methyl)carbamoyl)oxy)methyl)-2-nitrophenoxy)-6-(methoxycarbonyl)tetrahydro-2H-pyran-3,4,5-triyl triacetate (950 mg, 0.953 mmol) in MeOH (50 mL) and water (10 mL) was added DIPEA (5 mL). The resulting mixture was stirred at 0° C. for 10 h (reaction complete by TLC and LCMS monitoring). The solvent was evaporated under reduced pressure and the crude product was further purified by RP-HPLC to afford the title compound (288 mg, 35%). MS (m/z): [M+H]$^+$ calcd for $C_{35}H_{40}N_{10}O_{14}S$, 857.24; found, 857.5.

Example 4

Preparation of (2S,3S,4S,5R,6S)-3,4,5-Trihydroxy-6-(4-(((methyl(2-(N-methyl-4-(methyl((1r,4r)-4-((N-methylsulfamoyl)methyl)cyclohexyl)amino)-7H-pyrrolo[2,3-d]pyrimidine-7-carboxamido)ethyl)carbamoyl)oxy)methyl)-2-nitrophenoxy)tetrahydro-2H-pyran-2-carboxylic Acid (Compound VII-3)

Step 4-1—Preparation of (2S,3S,4S,5R,6S)-2-(Methoxycarbonyl)-6-(4-(((methyl(2-(N-methyl-4-(methyl((1r,4r)-4-((N-methylsulfamoyl)methyl)cyclohexyl)amino)-7H-pyrrolo[2,3-d]pyrimidine-7-carboxamido)ethyl)carbamoyl)oxy)methyl)-2-nitrophenoxy)tetrahydro-2H-pyran-3,4,5-triyl Triacetate

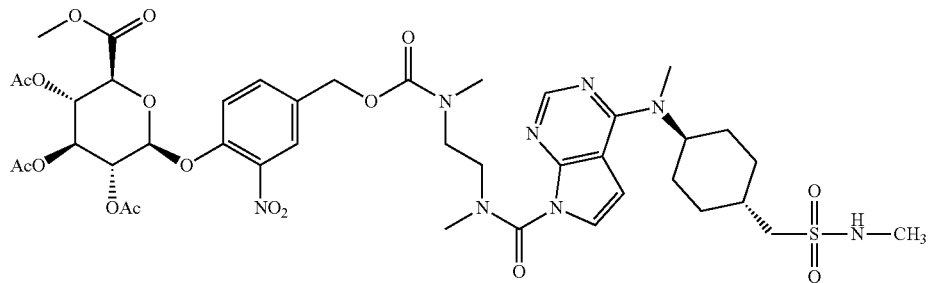 [SMILES: CNS(=O)(=O)C[C@H]1CC[C@H](N(C)c2ncnc3c2ccn3C(=O)N(C)CCN(C)C(=O)OCc2ccc(O[C@@H]3O[C@H](C(=O)OC)[C@@H](OC(C)=O)[C@H](OC(C)=O)[C@H]3OC(C)=O)c([N+](=O)[O-])c2)CC1]

To an ice cold solution of (2S,3R,4S,5S,6S)-2-(4-((((2-((chlorocarbonyl)(methyl)-amino)ethyl)(methyl)carbamoyl)oxy)methyl)-2-nitrophenoxy)-6-(methoxycarbonyl)tetrahydro-2H-pyran-3,4,5-triyl triacetate (1.40 g, 2.11 mmol) in DCM (100 mL) was added triethylamine (0.90 mL, 6.33 mmol) and DMAP (1.50 g, 12.66); followed by oclacitinib (500 mg, 1.47 mmol). The resulting mixture was stirred for 16 h (reaction complete by TLC monitoring). The solvent was evaporated under reduced pressure and the crude product was purified by column chromatography on silica gel (100-200 mesh) using 2% MeOH in DCM as eluent to provide the title compound (700 mg, 28%).

Step 4-2—Preparation of (2S,3S,4S,5R,6S)-3,4,5-Trihydroxy-6-(4-(((methyl(2-(N-methyl-4-(methyl((1r,4r)-4-((N-methylsulfamoyl)methyl)cyclohexyl)amino)-7H-pyrrolo[2,3-d]pyrimidine-7-carboxamido)ethyl)carbamoyl)oxy)methyl)-2-nitrophenoxy)tetrahydro-2H-pyran-2-carboxylic Acid (Compound VII-3)

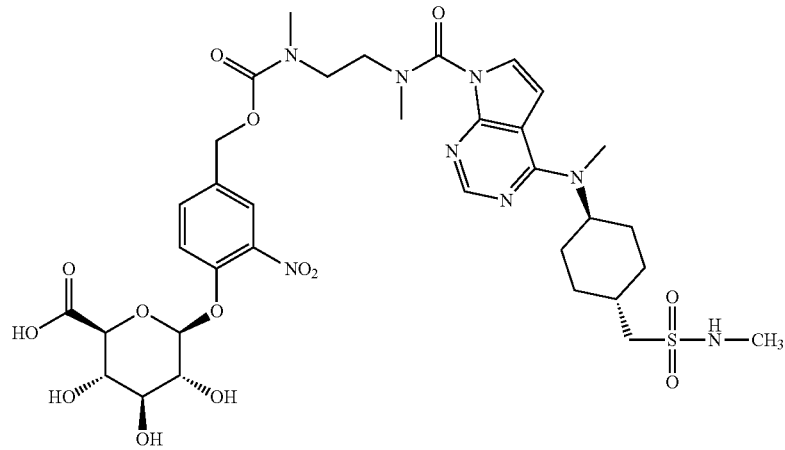 [SMILES: CNS(=O)(=O)C[C@H]1CC[C@H](N(C)c2ncnc3c2ccn3C(=O)N(C)CCN(C)C(=O)OCc2ccc(O[C@@H]3O[C@H](C(=O)O)[C@@H](O)[C@H](O)[C@H]3O)c([N+](=O)[O-])c2)CC1]

To an ice-cold solution of (2S,3S,4S,5R,6S)-2-(methoxycarbonyl)-6-(4-(((methyl(2-(N-methyl-4-(methyl((1r,4r)-4-((N-methylsulfamoyl)methyl)cyclohexyl)-amino)-7H-pyrrolo[2,3-d]pyrimidine-7-carboxamido)ethyl)carbamoyl)oxy)methyl)-2-nitrophenoxy)tetrahydro-2H-pyran-3,4,5-triyl triacetate (700 mg, 0.726 mmol) in MeOH (40 mL) and water (8.0 mL) was added DIPEA (4.0 mL). The resulting mixture was stirred at 0° C. for 10 h (reaction complete by TLC and LCMS monitoring). The solvent was evaporated under reduced pressure and the crude product was further purified by RP-HPLC to afford the title compound (309 mg, 25%). MS (m/z): [M+H]+ calcd for $C_{34}H_{46}N_8O_{14}S$, 823.29; found, 823.5.

Example 5

Preparation of 4-Nitrophenyl (R)-4-(1-(2-Cyano-1-cyclopentylethyl)-1H-pyrazol-4-yl)-7H-pyrrolo[2,3-d]pyrimidine-7-carboxylate

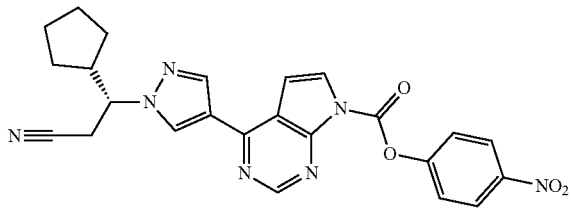 [SMILES: N#CC[C@H](C1CCCC1)n1cc(-c2ncnc3c2ccn3C(=O)Oc2ccc([N+](=O)[O-])cc2)cn1]

To a solution of ruxolitinib (2.40 mmol) in DCM (12 mL) is added a solution of sodium hydroxide (0.29 g, 7.20 mmol) in water (4.00 mL) and tetrabutylamonium bromide (0.08 g, 0.24 mmol). A solution of 4-nitrophenyl chloroformate (0.97 g, 4.80 mmol) in DCM (4 mL) is slowly added. The reaction mixture is stirred at room temperature for 1 h. The reaction mixture is extracted with DCM and the organic layer is washed with saturated aqueous ammonium chloride solution and brine, dried over sodium sulfate, filtered and concentrated under reduced pressure. The crude residue is purified by column chromatography to afford the title compound.

Example 6

Preparation of 4-Nitrophenyl 4-(1-(3-(Cyanomethyl)-1-(ethylsulfonyl)azetidin-3-yl)-1H-pyrazol-4-yl)-7H-pyrrolo[2,3-d]pyrimidine-7-carboxylate

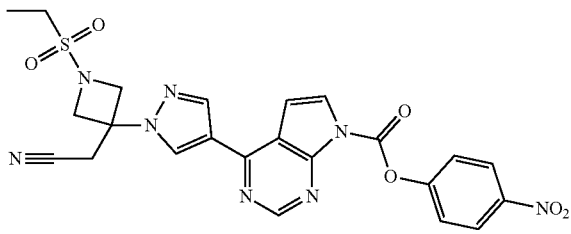 [SMILES: CCS(=O)(=O)N1CC(CC#N)(n2cc(-c3ncnc4c3ccn4C(=O)Oc3ccc([N+](=O)[O-])cc3)cn2)C1]

To a solution of baricitinib (2.40 mmol) in DCM (12 mL) is added a solution of sodium hydroxide (0.29 g, 7.20 mmol) in water (4.00 mL) and tetrabutylamonium bromide (0.08 g, 0.24 mmol). A solution of 4-nitrophenyl chloroformate (0.97 g, 4.80 mmol) in DCM (4 mL) is slowly added. The reaction mixture is stirred at room temperature for 1 h. The reaction mixture is extracted with DCM and the organic layer is washed with saturated aqueous ammonium chloride solution and brine, dried over sodium sulfate, filtered and concentrated under reduced pressure. The crude residue is purified by column chromatography to afford the title compound.

Example 7

Preparation of 4-Nitrophenyl 4-(Methyl((1r,4r)-4-((N-methylsulfamoyl)-methyl)cyclohexyl)amino)-7H-pyrrolo[2,3-d]pyrimidine-7-carboxylate

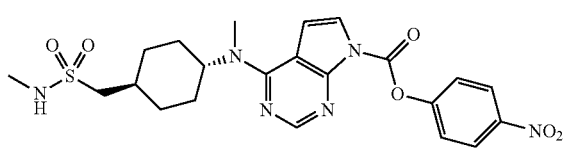 [SMILES: CNS(=O)(=O)C[C@H]1CC[C@H](N(C)c2ncnc3c2ccn3C(=O)Oc2ccc([N+](=O)[O-])cc2)CC1]

To a solution of oclacitinib (2.40 mmol) in DCM (12 mL) is added a solution of sodium hydroxide (0.29 g, 7.20 mmol) in water (4.00 mL) and tetrabutylamonium bromide (0.08 g, 0.24 mmol). A solution of 4-nitrophenyl chloroformate (0.97 g, 4.80 mmol) in DCM (4 mL) is slowly added. The reaction mixture is stirred at room temperature for 1 h. The reaction mixture is extracted with DCM and the organic layer is washed with saturated aqueous ammonium chloride solution and brine, dried over sodium sulfate, filtered and concentrated under reduced pressure. The crude residue is purified by column chromatography to afford the title compound.

Example 8

Preparation of (2S,3S,4S,5R,6S)-6-(((2-(4-(((3R,4R)-1-(2-Cyanoacetyl)-4-methylpiperidin-3-yl)(methyl)amino)-N-methyl-7H-pyrrolo[2,3-d]pyrimidine-7-carboxamido)ethyl)-(methyl)carbamoyl)oxy)-3,4,5-trihydroxytetrahydro-2H-pyran-2-carboxylic Acid (Compound II-1)

Step 8-1—Preparation of (3R,4S,5S,6S)-2-Hydroxy-6-(methoxycarbonyl)tetrahydro-2H-pyran-3,4,5-triyl Triacetate

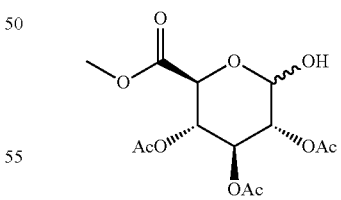

To an ice-cold solution of (2R,3R,4S,5S,6S)-2-bromo-6-(methoxycarbonyl)tetrahydro-2H-pyran-3,4,5-triyl triacetate (15.0 g, 37.76 mmol) in acetone (300 mL) and water (30 mL) was added silver carbonate (5.20 g, 18.88 mmol). The reaction mixture was warmed to room temperature and stirred at this temperature for 6 h. The reaction mixture was then filtered through a pad of diatomaceous earth (Celite®) and washed with DCM (250 mL). The combined organic layers were dried over sodium sulfate, filtered and concentrated under reduced pressure to afford the title compound (11.0 g, 87%) as a pale yellow solid.

Step 8-2—Preparation of (2S,3S,4S,5R,6S)-2-(Methoxycarbonyl)-6-(((4-nitrophenoxy)carbonyl)oxy)tetrahydro-2H-pyran-3,4,5-triyl Triacetate

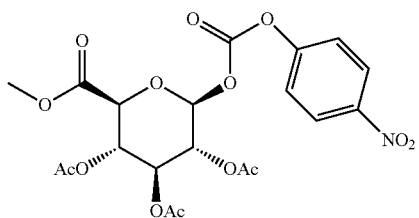 [SMILES: COC(=O)[C@H]1O[C@@H](OC(=O)Oc2ccc([N+](=O)[O-])cc2)[C@H](OC(C)=O)[C@@H](OC(C)=O)[C@@H]1OC(C)=O]

To a solution of (3R,4S,5S,6S)-2-hydroxy-6-(methoxycarbonyl)tetrahydro-2H-pyran-3,4,5-triyl triacetate (5.0 g, 14.94 mmol) in DCM (130 mL) at −10° C. was slowly added triethylamine (4.0 mL, 29.91 mmol) followed by p-nitrophenyl chloroformate (4.8 g, 15.70 mmol) in a minimum amount of DCM. The solution was warmed to room temperature and stirred at this temperature for 1 h. The solution was then diluted with DCM (100 mL) and washed sequentially with 5% aqueous sodium carbonate solution (3×50 mL) and 5% aqueous sulfuric acid solution (3×50 mL). The organic layer was dried over sodium sulfate, filtered and concentrated under reduced pressure. The crude residue was further triturated with diethyl ether to obtain the title compound (4.0 g, 66%).

For further information see, e.g., Thomas et al., *Synlett*, 2007, 12, 1966-1968; and Bunnelle, *J. Org. Chem.*, 2011, 76, 5429-5432.

Step 8-3—Preparation of (2S,3R,4S,5S,6S)-2-(((2-(4-(1-((R)-2-Cyano-1-cyclopentylethyl)-1H-pyrazol-4-yl)-N-methyl-7H-pyrrolo[2,3-d]pyrimidine-7-carboxamido)ethyl)(methyl)carbamoyl)oxy)-6-(methoxycarbonyl)tetrahydro-2H-pyran-3,4,5-triyl Triacetate

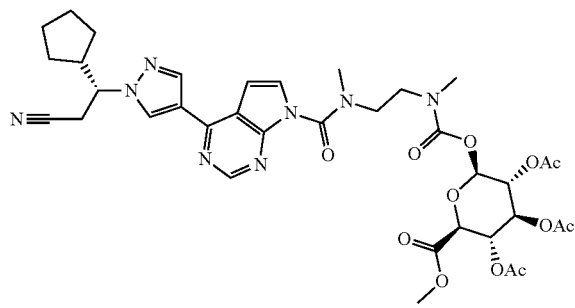 [SMILES: COC(=O)[C@H]1O[C@@H](OC(=O)N(C)CCN(C)C(=O)n2ccc3c(-c4cnn([C@H](CC#N)C5CCCC5)c4)ncnc32)[C@H](OC(C)=O)[C@@H](OC(C)=O)[C@@H]1OC(C)=O]

To an ice-cold solution of (2S,3S,4S,5R,6S)-2-(methoxycarbonyl)-6-(((4-nitrophenoxy)carbonyl)oxy)tetrahydro-2H-pyran-3,4,5-triyl triacetate (6 g, 12.01 mmol) in DCM (70 mL) is added N¹,N²-dimethylethane-1,2-diamine (1.05 g, 12.01 mmol). The resulting reaction mixture is warmed to room temperature and stirred for 30 min. After all the starting material is consumed, a solution of 4-nitrophenyl (R)-4-(1-(2-cyano-1-cyclopentylethyl)-1H-pyrazol-4-yl)-7H-pyrrolo[2,3-d]pyrimidine-7-carboxylate (12.01 mmol) in a minimum amount of DCM is added to the reaction mixture and the reaction mixture is stirred at room temperature for 2 h. The solvent is then evaporated under reduced pressure and the crude residue is purified by column chromatography to afford the title compound.

Step 8-4—Preparation of (2S,3S,4S,5R,6S)-6-(((2-(4-(1-((R)-2-Cyano-1-cyclopentylethyl)-1H-pyrazol-4-yl)-N-methyl-7H-pyrrolo[2,3-d]pyrimidine-7-carboxamido)ethyl)(methyl)carbamoyl)oxy)-3,4,5-trihydroxytetrahydro-2H-pyran-2-carboxylic Acid (Compound II-1)

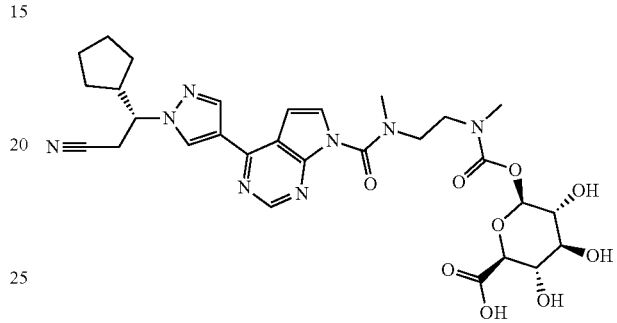

To an ice-cold solution of (2S,3R,4S,5S,6S)-2-(((2-(4-(1-((R)-2-cyano-1-cyclopentylethyl)-1H-pyrazol-4-yl)-N-methyl-7H-pyrrolo[2,3-d]pyrimidine-7-carboxamido)ethyl)(methyl)carbamoyl)oxy)-6-(methoxycarbonyl)tetrahydro-2H-pyran-3,4,5-triyl triacetate (9.5 mmol) in a 3:1 mixture of methanol (150 mL) and water (50 mL) is added DIPEA (25 mL). The reaction mixture is warmed to room temperature and stirred for 16 h. The solution is then concentrated under reduced pressure to give a crude residue that is purified by RP-HPLC to afford the title compound.

Example 9

Preparation of (2S,3S,4S,5R,6S)-6-(((2-(4-(1-(3-(Cyanomethyl)-1-(ethylsulfonyl)azetidin-3-yl)-1H-pyrazol-4-yl)-N-methyl-7H-pyrrolo[2,3-d]pyrimidine-7-carboxamido)ethyl)(methyl)carbamoyl)oxy)-3,4,5-trihydroxytetrahydro-2H-pyran-2-carboxylic Acid (Compound II-2)

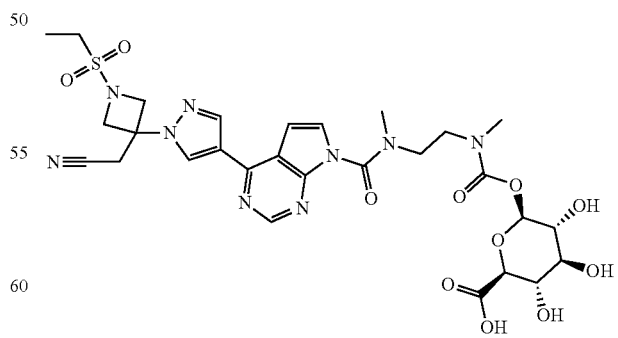

Following the procedures of Example 8 and using 4-nitrophenyl 4-(1-(3-(cyanomethyl)-1-(ethylsulfonyl)azetidin-3-yl)-1H-pyrazol-4-yl)-7H-pyrrolo[2,3-d]pyrimidine-7-carboxylate in Step 8-3, the title compound is prepared.

Example 10

Preparation of (2S,3S,4S,5R,6S)-3,4,5-Trihydroxy-6-((methyl(2-(N-methyl-4-(methyl((1r,4r)-4-((N-methylsulfamoyl)methyl)cyclohexyl)amino)-7H-pyrrolo[2,3-d]pyrimidine-7-carboxamido)ethyl)carbamoyl)oxy)tetrahydro-2H-pyran-2-carboxylic Acid (Compound II-3)

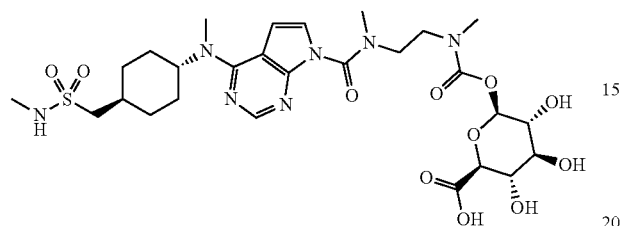

Following the procedures of Example 8 and using 4-nitrophenyl 4-(methyl((1r,4r)-4-((N-methylsulfamoyl)methyl)cyclohexyl)amino)-7H-pyrrolo[2,3-d]pyrimidine-7-carboxylate in Step 8-3, the title compound is prepared.

Example 11

Preparation of (2S,3S,4S,5R,6S)-6-(2-(4-(1-((R)-2-Cyano-1-cyclopentylethyl)-1H-pyrazol-4-yl)-N-methyl-7H-pyrrolo[2,3-d]pyrimidine-7-carboxamido)-4-nitrophenoxy)-3,4,5-trihydroxytetrahydro-2H-pyran-2-carboxylic Acid (Compound III-1)

Step 11-1—Preparation of N-(2-Hydroxy-5-nitrophenyl)formamide

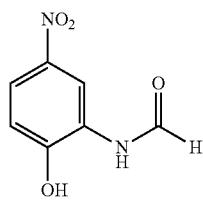 [SMILES: O=CNc1cc([N+](=O)[O-])ccc1O]

A solution of formic acid (125 mL, 3.25 mol) and acetic anhydride (310 mL, 3.25 mol) was heated to 70° C. for 2 h and then cooled to room temperature. A solution of 2-amino-4-nitrophenol (50.0 g, 0.325 mol) in THF (500 mL) was added to the resulting reaction mixture and this solution was stirred at room temperature for 3 h. After completion of the reaction (as determined by TLC), the reaction solution was poured into n-pentane (2.50 L) and the resulting mixture was stirred at room temperature for 30 min. The resultant precipitate was filtered and washed with n-pentane (200 mL). The solid cake was dried under high vacuum to afford the title compound (56.0 g, 97%) as off-white solid.

Step 11-2—Preparation of 2-(Methylamino)-4-nitrophenol

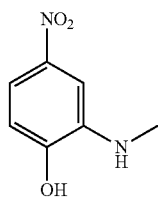

To an ice-cold solution of N-(2-hydroxy-5-nitrophenyl)formamide (56.0 g, 307.0 mmol) in THF (500 mL) was added dropwise a solution of borane dimethyl sulfide complex (95.5 mL, 922.0 mmol, 10.0 M). The resulting reaction mixture was left to warm to room temperature and stirred at this temperature for 4 h. After completion of the reaction (as determined by TLC), the reaction solution was cooled to 0° C. and quenched with methanol (150.0 mL). The solvent was evaporated under reduced pressure and the crude material was diluted with EtOAc (500 mL) and washed subsequently with water and saturated brine solution. The layers were separated and the organic phase was dried over sodium sulfate, filtered and concentrated under reduced pressure. The crude compound was triturated with n-pentane to afford the title compound (50.0 g, 97%) as off-white solid.

Step 11-3—Preparation of tert-Butyl (2-Hydroxy-5-nitrophenyl)(methyl)carbamate

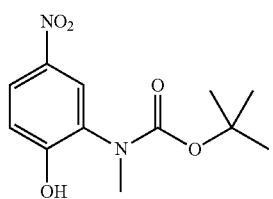 [SMILES: CN(C(=O)OC(C)(C)C)c1cc([N+](=O)[O-])ccc1O]

To an ice-cold solution of 2-(methylamino)-4-nitrophenol (50.0 g, 0.30 mol) in 1:1 THF and water (1.5 L) was added potassium carbonate (165.0 g, 1.2 mol) and di-tert-butyl dicarbonate (191.0 mL, 0.86 mol) and the solution was stirred at room temperature for 16 h. After protection of the aniline was complete (as determined by TLC), the solution was cooled to 0° C. and a solution of 4M sodium hydroxide (500 mL) was added. The reaction solution was stirred at room temperature for 4 days before the reaction mixture was extracted with EtOAc (3×500 mL). The combined organic phases were washed with water and brine, dried over sodium sulfate, filtered and concentrated under reduced pressure. The crude compound was triturated with diethyl ether to afford the title compound (79.0 g, 98%) as a yellow solid.

Step 11-4—Preparation of (2S,3R,4S,5S,6S)-2-(2-((tert-Butoxycarbonyl)(methyl)amino)-4-nitrophenoxy)-6-(methoxycarbonyl)tetrahydro-2H-pyran-3,4,5-triyl Triacetate

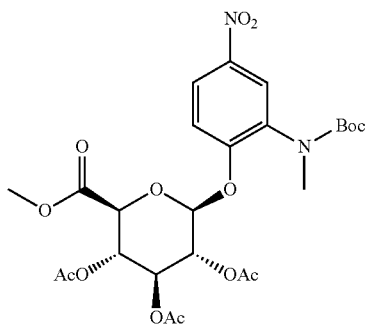 [SMILES: COC(=O)[C@H]1O[C@@H](Oc2ccc([N+](=O)[O-])cc2N(C)C(=O)OC(C)(C)C)[C@H](OC(C)=O)[C@@H](OC(C)=O)[C@@H]1OC(C)=O]

To an ice-cold solution of tert-butyl (2-hydroxy-5-nitrophenyl)(methyl)carbamate (24.0 g, 88.2 mmol) and silver(I) oxide (54.0 g, 220.5 mmol) in ACN (500 mL) was added a solution of (2R,3R,4S,5S,6S)-2-bromo-6-(methoxycarbonyl)tetrahydro-2H-pyran-3,4,5-triyl triacetate (35.0 g, 88.2 mmol) in ACN (250 mL). The reaction solution was stirred at room temperature for 12 h. After completion of the reaction (as determined by TLC), the solution was filtered through a bed of diatomaceous earth and washed with EtOAc. The solvent was evaporated under reduced pressure and the crude residue was purified by column chromatography (50% EtOAc in hexanes) to afford the title compound (25.0 g, 48%) as an off-white solid.

Step 11-5—Preparation of (2S,3S,4S,5R,6S)-2-(Methoxycarbonyl)-6-(2-(methylamino)-4-nitrophenoxy)tetrahydro-2H-pyran-3,4,5-triyl Triacetate

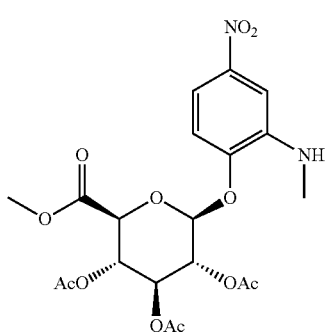

To an ice-cold solution of compound (2S,3R,4S,5S,6S)-2-(2-((tert-butoxycarbonyl)(methyl)amino)-4-nitrophenoxy)-6-(methoxycarbonyl)tetrahydro-2H-pyran-3,4,5-triyl triacetate (25.0 g, 42.75 mmol) in 1,4-dioxane (200 mL) was added dropwise a solution of hydrogen chloride in 1,4-dioxane (200.0 mL, 4.0 M). The reaction solution was stirred at room temperature for 6 h. After completion of the reaction (as determined by TLC), the solvent was evaporated under reduced pressure and the crude residue was triturated with diethyl ether (250 mL). The solid material was dissolved in aqueous sodium bicarbonate solution and extracted with EtOAc (3×250 mL). The combined organics were washed with water and brine, dried over sodium sulfate, filtered and concentrated under reduced pressure. The crude residue was purified by column chromatography (80% EtOAc in hexanes) to afford the title compound (9.82 g, 47%) as an off-white solid.

Step 11-6—Preparation of (2S,3R,4S,5S,6S)-2-(2-((Chlorocarbonyl)(methyl)amino)-4-nitrophenoxy)-6-(methoxycarbonyl)tetrahydro-2H-pyran-3,4,5-triyl Triacetate

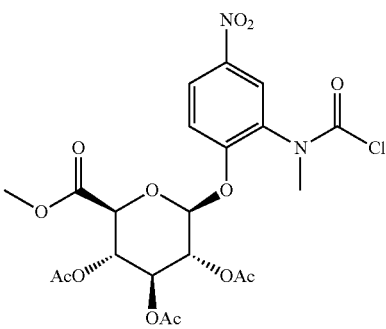

A solution of (2S,3S,4S,5R,6S)-2-(methoxycarbonyl)-6-(2-(methylamino)-4-nitrophenoxy)tetrahydro-2H-pyran-3,4,5-triyl triacetate (1.0 g, 2.06 mmol) in DCM (30 mL) was cooled to 0° C. and 15% phosgene in toluene (4.42 mL, 6.19 mmol) was added, followed by triethylamine (5.18 mL, 37.2 mmol). The solution was stirred at 0° C. for 2 h and then quenched with water (13 mL). The layers were separated and the aqueous layer was extracted with DCM (3×13 mL). The combined organic layers were dried over sodium sulfate, filtered and concentrated under reduced pressure. The crude residue was purified by column chromatography (0-50% EtOAc in hexanes) to afford the title compound (1.11 g, 98%) as a yellow foam.

Step 11-7—Preparation of (2S,3R,4S,5S,6S)-2-(2-(4-(1-((R)-2-Cyano-1-cyclopentylethyl)-1H-pyrazol-4-yl)-N-methyl-7H-pyrrolo[2,3-d]pyrimidine-7-carboxamido)-4-nitrophenoxy)-6-(methoxycarbonyl)tetrahydro-2H-pyran-3,4,5-triyl Triacetate

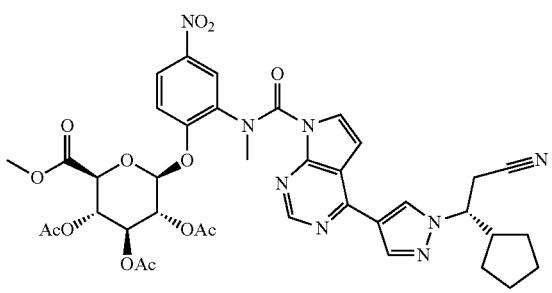 [SMILES: COC(=O)[C@H]1O[C@@H](Oc2ccc([N+](=O)[O-])cc2N(C)C(=O)n2ccc3c(-c4cnn([C@H](CC#N)C5CCCC5)c4)ncnc32)[C@H](OC(C)=O)[C@@H](OC(C)=O)[C@@H]1OC(C)=O]

To a solution of ruxolitinib (0.69 mmol) in DCM (5.7 mL) at 0° C. is added triethylamine (0.12 mL, 0.86 mmol), DMAP (6.99 mg, 0.06 mmol) and (2S,3R,4S,5S,6S)-2-(2-((chlorocarbonyl)(methyl)amino)-4-nitrophenoxy)-6-(methoxycarbonyl)tetrahydro-2H-pyran-3,4,5-triyl triacetate (0.31 g, 0.57 mmol) as a solution in DCM (5.7 mL). The reaction mixture is stirred at 0° C. for 2 h and warmed to room temperature overnight. Water (1 mL) is added to the solution, the layers are separated and the aqueous layer is extracted with DCM (3×2 mL). The combined organic extracts are dried over sodium sulfate, filtered and concentrated under reduced pressure. The crude residue is purified by column chromatography to afford the title compound.

Step 11-8—Preparation of (2S,3S,4S,5R,6S)-6-(2-(4-(1-((R)-2-Cyano-1-cyclopentylethyl)-1H-pyrazol-4-yl)-N-methyl-7H-pyrrolo[2,3-d]pyrimidine-7-carboxamido)-4-nitrophenoxy)-3,4,5-trihydroxytetrahydro-2H-pyran-2-carboxylic Acid (Compound III-1)

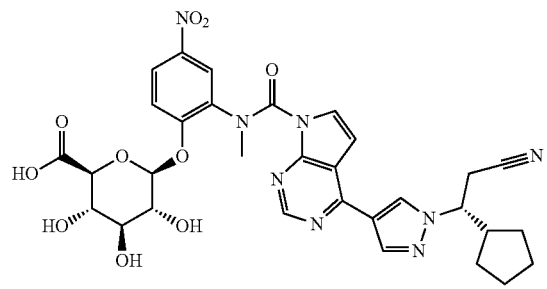 [SMILES: CN(C(=O)n1ccc2c(-c3cnn([C@H](CC#N)C4CCCC4)c3)ncnc21)c1cc([N+](=O)[O-])ccc1O[C@@H]1O[C@H](C(=O)O)[C@@H](O)[C@H](O)[C@H]1O]

To a solution of (2S,3R,4S,5S,6S)-2-(2-(4-(1-((R)-2-cyano-1-cyclopentylethyl)-1H-pyrazol-4-yl)-N-methyl-7H-pyrrolo[2,3-d]pyrimidine-7-carboxamido)-4-nitrophenoxy)-6-(methoxycarbonyl)tetrahydro-2H-pyran-3,4,5-triyl triacetate (1.49 mmol) in methanol (3.50 mL), water (3.50 mL) and THF (3.50 mL) is added lithium hydroxide (36 mg, 1.49 mmol) and the solution is stirred at room temperature for 6 h and then concentrated under reduced pressure. The crude material is purified by reverse phase column chromatography to afford the title compound.

Example 12

Preparation of (2S,3S,4S,5R,6S)-6-(2-(4-(1-(3-(Cyanomethyl)-1-(ethylsulfonyl)azetidin-3-yl)-1H-pyrazol-4-yl)-N-methyl-7H-pyrrolo[2,3-d]pyrimidine-7-carboxamido)-4-nitrophenoxy)-3,4,5-trihydroxytetrahydro-2H-pyran-2-carboxylic Acid (Compound III-2)

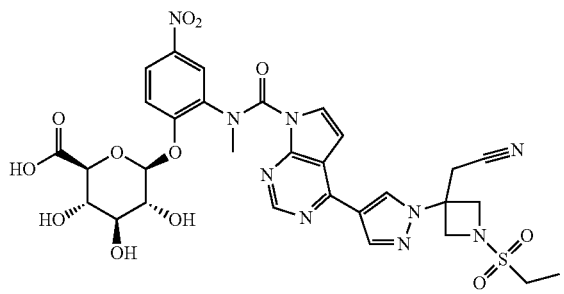 [SMILES: CCS(=O)(=O)N1CC(CC#N)(n2cc(-c3ncnc4c3ccn4C(=O)N(C)c3cc([N+](=O)[O-])ccc3O[C@@H]3O[C@H](C(=O)O)[C@@H](O)[C@H](O)[C@H]3O)cn2)C1]

Following the procedures of Example 11 and using baricitinib in Step 11-7, the title compound is prepared.

Example 13

Preparation of (2S,3S,4S,5R,6S)-3,4,5-Trihydroxy-6-(2-(N-methyl-4-(methyl((1r,4S)-4-((N-methylsulfamoyl)methyl)cyclohexyl)amino)-7H-pyrrolo[2,3-d]pyrimidine-7-carboxamido)-4-nitrophenoxy)tetrahydro-2H-pyran-2-carboxylic Acid (Compound III-3)

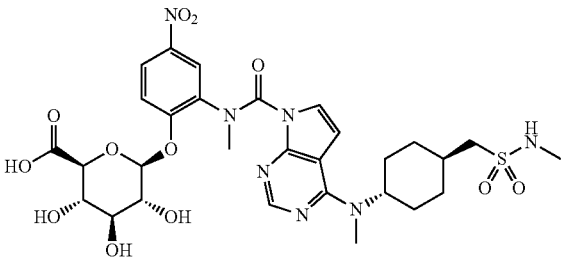

Following the procedures of Example 11 and using oclacitinib in Step 11-7, the title compound is prepared.

Example 14

Preparation of (2S,3S,4S,5R,6S)-6-(2-(4-(1-((R)-2-Cyano-1-cyclopentylethyl)-1H-pyrazol-4-yl)-N-methyl-7H-pyrrolo[2,3-d]pyrimidine-7-carboxamido)phenoxy)-3,4,5-trihydroxytetrahydro-2H-pyran-2-carboxylic Acid (Compound III-4)

Step 14-1—Preparation of (2S,3S,4S,5R,6S)-2-(Methoxycarbonyl)-6-(2-nitrophenoxy)tetrahydro-2H-pyran-3,4,5-triyl Triacetate

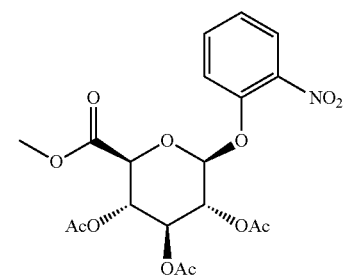

To an ice-cold solution of 2-nitrophenol (28.2 g, 201.43 mmol) and silver(I) oxide (117.0 g, 201.43 mmol) in ACN (1.40 L) was added a solution of (2R,3R,4S,5S,6S)-2-bromo-6-(methoxycarbonyl)tetrahydro-2H-pyran-3,4,5-triyl triacetate (80.0 g, 25.18 mmol) in ACN (200 mL). The reaction solution was stirred at room temperature for 12 h. After completion of the reaction (as determined by TLC), the solution was filtered through a bed of diatomaceous earth and washed with EtOAc. The solvent was evaporated under reduced pressure and the crude residue was purified by column chromatography (10% EtOAc in hexanes) to afford the title compound (70.0 g, 77%) as an off-white solid.

Step 14-2—Preparation of (2S,3R,4S,5S,6S)-2-(2-Aminophenoxy)-6-(methoxycarbonyl)tetrahydro-2H-pyran-3,4,5-triyl Triacetate

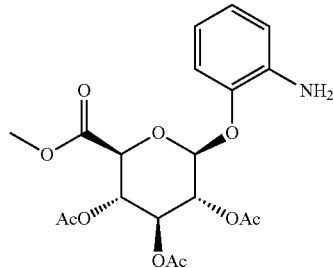 [SMILES: COC(=O)[C@H]1O[C@@H](Oc2ccccc2[N+](=O)[O-])[C@H](OC(C)=O)[C@@H](OC(C)=O)[C@@H]1OC(C)=O]

To a solution of compound (2S,3S,4S,5R,6S)-2-(methoxycarbonyl)-6-(2-nitrophenoxy)tetrahydro-2H-pyran-3,4,5-triyl triacetate (35.0 g, 76.86 mmol) in THF (750 mL) was added palladium on carbon (3.5 g). The resulting reaction mixture was stirred under an atmosphere of hydrogen (50 psi) in an autoclave for 6 h at room temperature. After completion of the reaction (as determined by LCMS), the solution was filtered through a bed of diatomaceous earth and washed with 5% methanol in DCM. The solvent was evaporated under reduced pressure and the crude residue was triturated with diethyl ether to afford the title compound (32.0 g, 98%) as an off-white solid.

Step 14-3—Preparation of (2S,3R,4S,5S,6S)-2-(2-Formamidophenoxy)-6-(methoxycarbonyl)tetrahydro-2H-pyran-3,4,5-triyl Triacetate

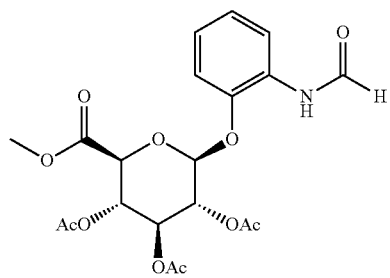 [SMILES: COC(=O)[C@H]1O[C@@H](Oc2ccccc2NC=O)[C@H](OC(C)=O)[C@@H](OC(C)=O)[C@@H]1OC(C)=O]

A solution of formic acid (36 mL, 942.0 mmol) and acetic anhydride (90.0 mL, 942.0 mmol) was heated to 70° C. for 2 h and then cooled to room temperature. A solution of (2S,3R,4S,5S,6S)-2-(2-aminophenoxy)-6-(methoxycarbonyl)tetrahydro-2H-pyran-3,4,5-triyl triacetate (40.0 gm, 94.2 mmol) in THF (500 mL) was added to the resulting reaction mixture and this solution was stirred at room temperature for 3 h. After completion of the reaction (as determined by TLC), the reaction solution was poured into n-pentane (2.50 L) and the resulting mixture was stirred at room temperature for 30 min. The resultant precipitate was filtered and washed with n-pentane (200 mL). The solid cake was dried under high vacuum to afford the title compound (35.0 g, 82%) as an off-white solid.

Step 14-4—Preparation of (2S,3S,4S,5R,6S)-2-(Methoxycarbonyl)-6-(2-(methylamino)phenoxy)tetrahydro-2H-pyran-3,4,5-triyl Triacetate

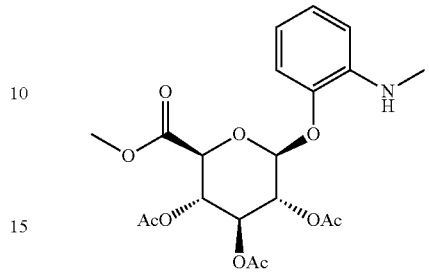

To an ice-cold solution of (2S,3R,4S,5S,6S)-2-(2-formamidophenoxy)-6-(methoxycarbonyl)tetrahydro-2H-pyran-3,4,5-triyl triacetate (35.0 g, 77.2 mmol) in THF (500 mL) was added dropwise a solution of borane dimethyl sulfide complex (23.2 mL, 231.6 mmol, 10.0 M). The resulting reaction mixture was left to warm to room temperature and stirred at this temperature for 4 h. After completion of the reaction (as determined by TLC), the reaction solution was cooled to 0° C. and quenched with methanol (50.0 mL). The solvent was evaporated under reduced pressure and the crude material was diluted with EtOAc (200 mL) and washed subsequently with water and saturated brine solution. The layers were separated and the organic phase was dried over sodium sulfate, filtered and concentrated under reduced pressure. The crude residue was purified by column chromatography (20% EtOAc in hexanes) to afford the title compound (32.5 g, 96%) as an off-white solid.

Step 14-5—Preparation of (2S,3R,4S,5S,6S)-2-(2-((Chlorocarbonyl)(methyl)amino)phenoxy)-6-(methoxycarbonyl)tetrahydro-2H-pyran-3,4,5-triyl Triacetate

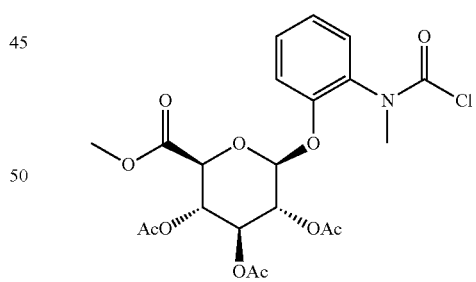

A solution of (2S,3S,4S,5R,6S)-2-(methoxycarbonyl)-6-(2-(methylamino)phenoxy)tetrahydro-2H-pyran-3,4,5-triyl triacetate (0.92 g, 2.00 mmol) in DCM (30 mL) was cooled to 0° C. and 15% phosgene in toluene (4.29 mL, 6.01 mmol) was added, followed by triethylamine (5.02 mL, 36.0 mmol) and the solution was stirred at 0° C. for 2 h and then warmed to room temperature and stirred at this temperature overnight. The solution was quenched with water (13 mL), the layers were separated and the aqueous layer was extracted with DCM (3×13 mL). The combined organic layers were dried over sodium sulfate, filtered and concentrated under reduced pressure. The crude residue was purified by column chromatography (0-50% EtOAc in hexanes) to afford the title compound (0.91 g, 90%) as a yellow foam.

Step 14-6—Preparation of (2S,3R,4S,5S,6S)-2-(2-(4-(1-((R)-2-Cyano-1-cyclopentylethyl)-1H-pyrazol-4-yl)-N-methyl-7H-pyrrolo[2,3-d]pyrimidine-7-carboxamido)phenoxy)-6-(methoxycarbonyl)tetrahydro-2H-pyran-3,4,5-triyl Triacetate

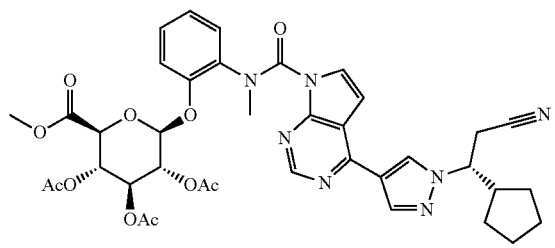 [SMILES: COC(=O)[C@H]1O[C@@H](Oc2ccccc2N(C)C(=O)n2ccc3c(-c4cnn([C@H](CC#N)C5CCCC5)c4)ncnc32)[C@H](OC(C)=O)[C@@H](OC(C)=O)[C@@H]1OC(C)=O]

To a solution of ruxolitinib (1.80 mmol) in DCM (16.4 mL) at 0° C. is added triethylamine (0.38 mL, 2.70 mmol), DMAP (22 mg, 0.18 mmol) and (2S,3R,4S,5S,6S)-2-(2-((chlorocarbonyl)(methyl)amino)phenoxy)-6-(methoxycarbonyl)tetrahydro-2H-pyran-3,4,5-triyl triacetate (0.91 g, 1.80 mmol) as a solution in DCM (16.4 mL) and the reaction mixture is stirred at 0° C. for 2 h. Water is added to the solution (1 mL), the layers are separated and the aqueous layer is extracted with DCM (3×2 mL). The combined organic extracts are dried over sodium sulfate, filtered and concentrated under reduced pressure. The crude residue is purified by column chromatography to afford the title compound.

Step 14-7—Preparation of (2S,3S,4S,5R,6S)-6-(2-(4-(1-((R)-2-Cyano-1-cyclopentylethyl)-1H-pyrazol-4-yl)-N-methyl-7H-pyrrolo[2,3-d]pyrimidine-7-carboxamido)phenoxy)-3,4,5-trihydroxytetrahydro-2H-pyran-2-carboxylic Acid (Compound III-4)

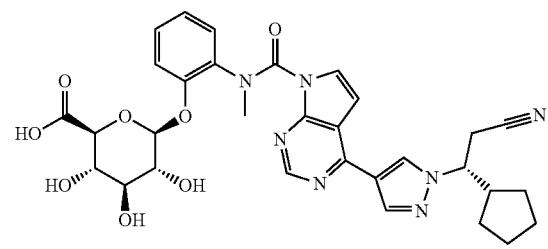 [SMILES: CN(C(=O)n1ccc2c(-c3cnn([C@H](CC#N)C4CCCC4)c3)ncnc21)c1ccccc1O[C@@H]1O[C@H](C(=O)O)[C@@H](O)[C@H](O)[C@H]1O]

To a solution of (2S,3R,4S,5S,6S)-2-(2-(4-(1-((R)-2-cyano-1-cyclopentylethyl)-1H-pyrazol-4-yl)-N-methyl-7H-pyrrolo[2,3-d]pyrimidine-7-carboxamido)phenoxy)-6-(methoxycarbonyl)tetrahydro-2H-pyran-3,4,5-triyl triacetate (0.75 mmol) in methanol (1.75 mL), water (1.75 mL) and THF (1.75 mL) is added lithium hydroxide (58 mg, 2.43 mmol) and the solution is stirred at room temperature for 1.5 h. The crude material is purified by reverse phase column chromatography to afford the title compound.

Example 15

Preparation of (2S,3S,4S,5R,6S)-6-(2-(4-(1-(3-(Cyanomethyl)-1-(ethylsulfonyl)azetidin-3-yl)-1H-pyrazol-4-yl)-N-methyl-7H-pyrrolo[2,3-d]pyrimidine-7-carboxamido)phenoxy)-3,4,5-trihydroxytetrahydro-2H-pyran-2-carboxylic Acid (Compound III-5)

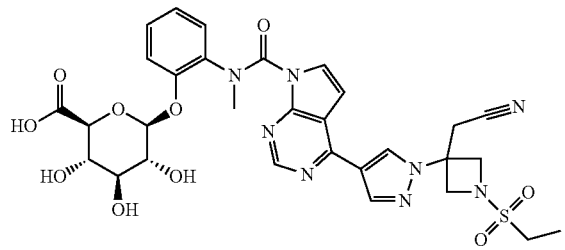 [SMILES: CCS(=O)(=O)N1CC(CC#N)(n2cc(-c3ncnc4c3ccn4C(=O)N(C)c3ccccc3O[C@@H]3O[C@H](C(=O)O)[C@@H](O)[C@H](O)[C@H]3O)cn2)C1]

Following the procedures of Example 14 and using baricitinib in Step 14-6, the title compound is prepared.

Example 16

Preparation of (2S,3S,4S,5R,6S)-3,4,5-Trihydroxy-6-(2-(N-methyl-4-(methyl((1r,4S)-4-((N-methylsulfamoyl)methyl)cyclohexyl)amino)-7H-pyrrolo[2,3-d]pyrimidine-7-carboxamido)phenoxy)tetrahydro-2H-pyran-2-carboxylic Acid (Compound III-6)

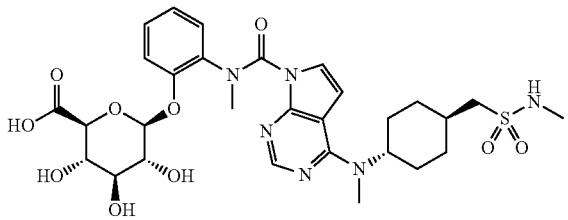 [SMILES: CNS(=O)(=O)C[C@H]1CC[C@H](N(C)c2ncnc3c2ccn3C(=O)N(C)c2ccccc2O[C@@H]2O[C@H](C(=O)O)[C@@H](O)[C@H](O)[C@H]2O)CC1]

Following the procedures of Example 14 and using oclacitinib in Step 14-6, the title compound is prepared.

Example 17

Preparation of (2S,3S,4S,5R,6S)-6-(2-(4-(1-((R)-2-Cyano-1-cyclopentylethyl)-1H-pyrazol-4-yl)-N-methyl-7H-pyrrolo[2,3-d]pyrimidine-7-carboxamido)-4-methylphenoxy)-3,4,5-trihydroxytetrahydro-2H-pyran-2-carboxylic Acid (Compound III-7)

Step 17-1—Preparation of (2S,3S,4S,5R,6S)-2-(Methoxycarbonyl)-6-(4-methyl-2-nitrophenoxy)tetrahydro-2H-pyran-3,4,5-triyl Triacetate

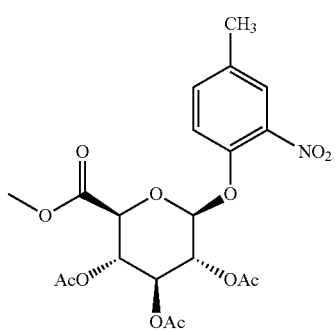 [SMILES: COC(=O)[C@H]1O[C@@H](Oc2ccc(C)cc2[N+](=O)[O-])[C@H](OC(C)=O)[C@@H](OC(C)=O)[C@@H]1OC(C)=O]

To an ice-cold solution of 4-methyl-2-nitrophenol (5.8 g, 37.7 mmol) in ACN (500 mL) was added silver(I) oxide (22.0 gm, 94.4 mmol) followed by the slow addition of a solution of (2R,3R,4S,5S,6S)-2-bromo-6-(methoxycarbonyl)tetrahydro-2H-pyran-3,4,5-triyl triacetate (15.0 g, 37.7 mmol) in a minimum amount of ACN. The resulting solution was stirred at room temperature for 16 h and then it was filtered through a pad of diatomaceous earth and washed with EtOAc. The filtrate was concentrated under reduced pressure and the crude residue was purified by column chromatography (10% EtOAc in hexanes) to afford the title compound (15.0 g, 85%) as an off-white solid.

Step 17-2—Preparation of (2S,3R,4S,5S,6S)-2-(2-Amino-4-methylphenoxy)-6-(methoxycarbonyl)tetrahydro-2H-pyran-3,4,5-triyl Triacetate

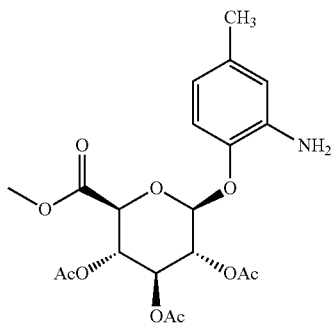

To a stirred solution of (2S,3S,4S,5R,6S)-2-(methoxycarbonyl)-6-(4-methyl-2-nitrophenoxy)tetrahydro-2H-pyran-3,4,5-triyl triacetate (15.0 g, 31.95 mmol) in THF (300 mL) was added palladium on carbon (1.50 g, 10% w/w). The resulting black solution was stirred under an atmosphere of hydrogen for 16 h and then filtered through a pad of diatomaceous earth and washed with EtOAc. The solvent was evaporated under reduced pressure to afford the title compound (12.0 g, 86%) as an off-white solid.

Step 17-3—Preparation of (2S,3R,4S,5S,6S)-2-(2-Formamido-4-methylphenoxy)-6-(methoxycarbonyl)tetrahydro-2H-pyran-3,4,5-triyl Triacetate

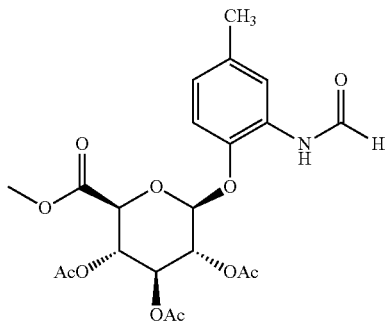 [SMILES: COC(=O)[C@H]1O[C@@H](Oc2ccc(C)cc2NC=O)[C@H](OC(C)=O)[C@@H](OC(C)=O)[C@@H]1OC(C)=O]

A stirred solution of formic acid (11.15 mL, 295.8 mmol) and acetic anhydride (28.0 mL, 295.8 mmol) was heated at 70° C. for 2 h and then cooled to room temperature. A solution of (2S,3R,4S,5S,6S)-2-(2-amino-4-methylphenoxy)-6-(methoxycarbonyl)tetrahydro-2H-pyran-3,4,5-triyl triacetate (13.0 g, 29.58 mmol) in a minimum amount of THF was then slowly added and the combined mixture was stirred at room temperature for 3 h. The solution was then poured into n-pentane (1.0 L) and stirred for 30 min during which time a precipitate formed. The solid was filtered, washed with n-pentane and dried under high vacuum to afford the title compound (13.0 g, 84%) as an off-white solid.

Step 17-4—Preparation of (2S,3S,4S,5R,6S)-2-(Methoxycarbonyl)-6-(4-methyl-2-(methylamino)phenoxy)tetrahydro-2H-pyran-3,4,5-triyl Triacetate

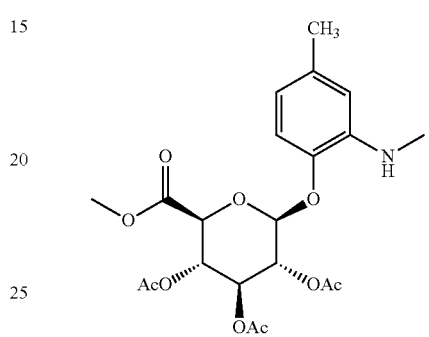

To an ice-cold solution of (2S,3R,4S,5S,6S)-2-(2-formamido-4-methylphenoxy)-6-(methoxycarbonyl)tetrahydro-2H-pyran-3,4,5-triyl triacetate (13.0 g, 27.81 mmol) in THF (150 mL) was slowly added borane dimethyl sulfide complex (8.3 mL, 83.43 mmol, 10.0 M solution). The reaction mixture was stirred at room temperature for 3 h and then it was quenched with methanol (100 mL) and the solvent was removed under reduced pressure. The residue was diluted with water (500 mL) and extracted with EtOAc (3×500 mL). The combined organic layers were washed with brine, dried over sodium sulfate, filtered and concentrated under reduced pressure. The crude residue was purified by column chromatography (20% EtOAc in hexanes) to afford the title compound (10.6 g, 58%) as an off-white solid.

Step 17-5—Preparation of (2S,3R,4S,5S,6S)-2-(2-((Chlorocarbonyl)(methyl)amino)-4-methylphenoxy)-6-(methoxycarbonyl)tetrahydro-2H-pyran-3,4,5-triyl Triacetate

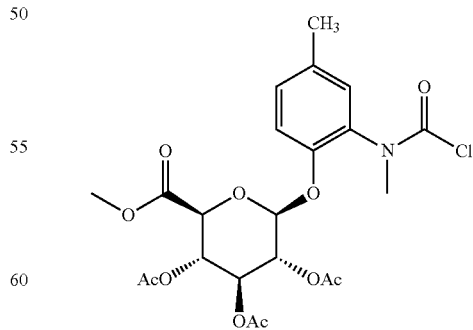

A solution of (2S,3S,4S,5R,6S)-2-(methoxycarbonyl)-6-(4-methyl-2-(methylamino)phenoxy)tetrahydro-2H-pyran-3,4,5-triyl triacetate (1.00 g, 2.16 mmol) in DCM (30.0 mL) was cooled to 0° C. and 15% phosgene in toluene (4.63 mL, 6.48 mmol) was added, followed by triethylamine (5.42 mL, 38.9 mmol) and the solution was stirred at 0° C. for 2 h and then warmed to room temperature and stirred at this temperature overnight. The solution was quenched with water (13 mL), the layers were separated and the aqueous layer was extracted with DCM (3×13 mL). The combined organic layers were dried over sodium sulfate, filtered and concentrated under reduced pressure. The crude residue was purified by column chromatography (0-60% EtOAc in hexanes) to afford the title compound (1.12 g, 100%) as a white foam.

Step 17-6—Preparation of (2S,3R,4S,5S,6S)-2-(2-(4-(1-((R)-2-Cyano-1-cyclopentylethyl)-1H-pyrazol-4-yl)-N-methyl-7H-pyrrolo[2,3-d]pyrimidine-7-carboxamido)-4-methylphenoxy)-6-(methoxycarbonyl)tetrahydro-2H-pyran-3,4,5-triyl Triacetate

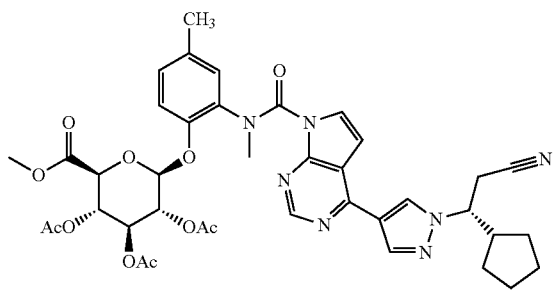 [SMILES: COC(=O)[C@H]1O[C@@H](Oc2ccc(C)cc2N(C)C(=O)n2ccc3c(-c4cnn([C@H](CC#N)C5CCCC5)c4)ncnc32)[C@H](OC(C)=O)[C@@H](OC(C)=O)[C@@H]1OC(C)=O]

To a solution of ruxolitinib (2.16 mmol) in DCM (21.6 mL) at 0° C. is added triethylamine (0.45 mL, 3.24 mmol), DMAP (26 mg, 0.22 mmol) and (2S,3R,4S,5S,6S)-2-(2-((chlorocarbonyl)(methyl)amino)-4-methylphenoxy)-6-(methoxycarbonyl)tetrahydro-2H-pyran-3,4,5-triyl triacetate (1.12 g, 2.16 mmol) as a solution in DCM (21.6 mL). The reaction mixture is stirred at 0° C. for 2 h and then warmed to room overnight. Water is added to the solution (10 mL) and the layers are separated. The aqueous layer is extracted with DCM (3×20 mL). The combined organic extracts are dried over sodium sulfate, filtered and concentrated under reduced pressure. The crude residue is purified by column chromatography to afford the title compound.

Step 17-7—Preparation of (2S,3S,4S,5R,6S)-6-(2-(4-(1-((R)-2-Cyano-1-cyclopentylethyl)-1H-pyrazol-4-yl)-N-methyl-7H-pyrrolo[2,3-d]pyrimidine-7-carboxamido)-4-methylphenoxy)-3,4,5-trihydroxytetrahydro-2H-pyran-2-carboxylic Acid (Compound III-7)

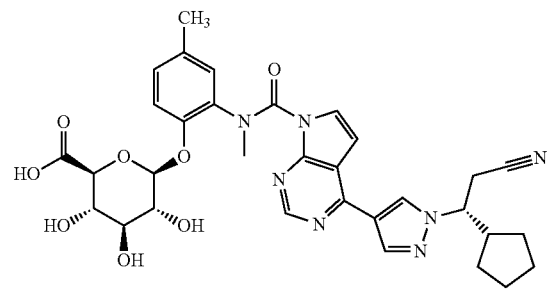 [SMILES: Cc1ccc(O[C@@H]2O[C@H](C(=O)O)[C@@H](O)[C@H](O)[C@H]2O)c(N(C)C(=O)n2ccc3c(-c4cnn([C@H](CC#N)C5CCCC5)c4)ncnc32)c1]

To a solution of (2S,3R,4S,5S,6S)-2-(2-(4-(1-((R)-2-cyano-1-cyclopentylethyl)-1H-pyrazol-4-yl)-N-methyl-7H-pyrrolo[2,3-d]pyrimidine-7-carboxamido)-4-methylphenoxy)-6-(methoxycarbonyl)tetrahydro-2H-pyran-3,4,5-triyl triacetate (0.30 mmol) in 1:1:1 methanol (1 mL):THF (1 mL):water (1 mL) is added lithium hydroxide (14 mg, 0.60 mmol). The solution is stirred at room temperature for 30 min and the reaction mixture is concentrated under reduced pressure. The crude material is purified by reverse phase column chromatography to afford the title compound.

Example 18

Preparation of (2S,3S,4S,5R,6S)-6-(2-(4-(1-(3-(Cyanomethyl)-1-(ethylsulfonyl)azetidin-3-yl)-1H-pyrazol-4-yl)-N-methyl-7H-pyrrolo[2,3-d]pyrimidine-7-carboxamido)-4-methylphenoxy)-3,4,5-trihydroxytetrahydro-2H-pyran-2-carboxylic Acid (Compound III-8)

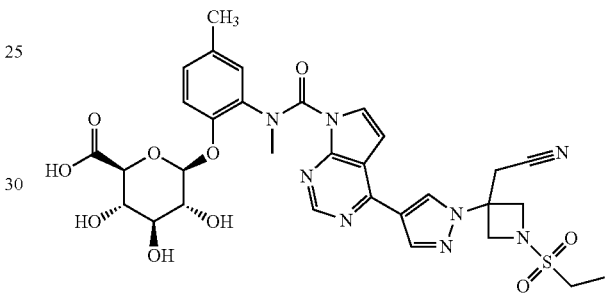

Following the procedures of Example 17 and using baricitinib in Step 17-6, the title compound is prepared.

Example 19

Preparation of (2S,3S,4S,5R,6S)-3,4,5-Trihydroxy-6-(4-methyl-2-(N-methyl-4-(methyl((1r,4S)-4-((N-methylsulfamoyl)methyl)cyclohexyl)amino)-7H-pyrrolo[2,3-d]pyrimidine-7-carboxamido)phenoxy)tetrahydro-2H-pyran-2-carboxylic Acid (Compound III-9)

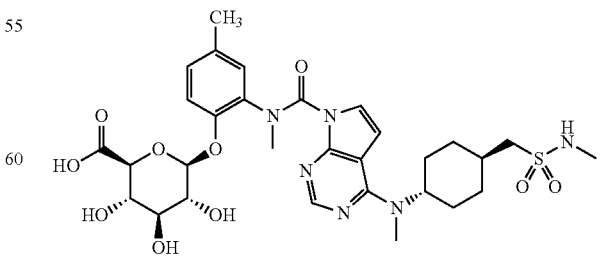

Following the procedures of Example 17 and using oclacitinib in Step 17-6, the title compound is prepared.

Example 20

Preparation of (2S,3S,4S,5R,6S)-6-(2-(4-(1-((R)-2-Cyano-1-cyclopentylethyl)-1H-pyrazol-4-yl)-N-methyl-7H-pyrrolo[2,3-d]pyrimidine-7-carboxamido)-4-(trifluoromethyl)phenoxy)-3,4,5-trihydroxytetrahydro-2H-pyran-2-carboxylic Acid (Compound III-10)

Step 20-1—Preparation of (2S,3S,4S,5R,6S)-2-(Methoxycarbonyl)-6-(2-nitro-4-(trifluoromethyl)phenoxy)tetrahydro-2H-pyran-3,4,5-triyl Triacetate

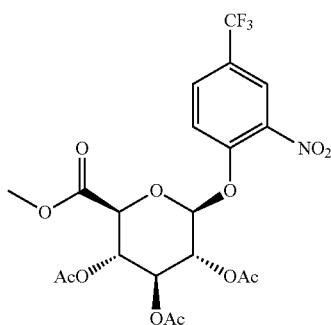

To an ice-cold solution of 2-nitro-4-(trifluoromethyl)phenol (7.0 mL, 50.36 mmol) in ACN (500 mL) was added silver(I) oxide (37.1 g, 157.4 mmol), followed by the slow addition of a solution of (2R,3R,4S,5S,6S)-2-bromo-6-(methoxycarbonyl)tetrahydro-2H-pyran-3,4,5-triyl triacetate (25.0 g, 62.95 mmol) in a minimum amount of ACN. The resulting solution was stirred at room temperature for 16 h and then it was filtered through a pad of diatomaceous earth and washed with EtOAc. The filtrate was concentrated under reduced pressure and the crude residue was purified by column chromatography (30% EtOAc in hexanes) to afford the title compound (25.0 g, 76%) as an off-white solid.

Step 20-2—Preparation of (2S,3R,4S,5S,6S)-2-(2-Amino-4-(trifluoromethyl)phenoxy)-6-(methoxycarbonyl)tetrahydro-2H-pyran-3,4,5-triyl Triacetate

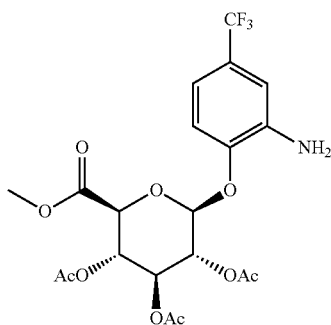

To a stirred solution of (2S,3S,4S,5R,6S)-2-(methoxycarbonyl)-6-(2-nitro-4-(trifluoromethyl)phenoxy)tetrahydro-2H-pyran-3,4,5-triyl triacetate (20.0 g, 38.21 mmol) in THF (300 mL) was added palladium on carbon (2.50 g, 10% w/w). The black solution was stirred under an atmosphere of hydrogen for 16 h and then it was filtered through a pad of diatomaceous earth and washed with EtOAc wash. The filtrate was concentrated under reduced pressure to afford the title compound (18.0 g, 96%) as an off-white solid.

Step 20-3—Preparation of (2S,3R,4S,5S,6S)-2-(2-Formamido-4-(trifluoromethyl)phenoxy)-6-(methoxycarbonyl)tetrahydro-2H-pyran-3,4,5-triyl Triacetate

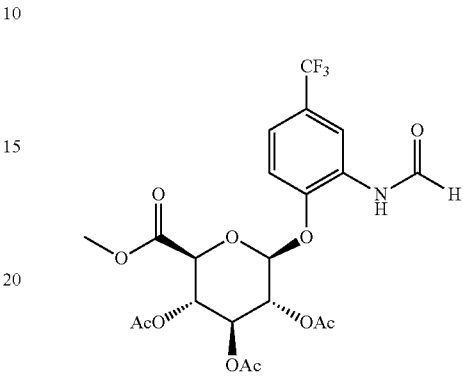

A stirred solution of formic acid (13.0 mL, 345.0 mmol) and acetic anhydride (32.0 mL, 345.0 mmol) was heated at 70° C. for 2 h and then cooled to room temperature.

A solution of (2S,3R,4S,5S,6S)-2-(2-amino-4-(trifluoromethyl)phenoxy)-6-(methoxycarbonyl) tetrahydro-2H-pyran-3,4,5-triyl triacetate (17.0 g, 34.45 mmol) in a minimum amount of THF was then slowly added and the combined mixture was stirred at room temperature for 3 h. The solution was then poured into n-pentane (1.0 L) and stirred for 30 min during which time a precipitate formed. The solid was filtered, washed with n-pentane and dried under high vacuum to afford the title compound (16.5 g, 92%) as an off-white solid.

Step 20-4—Preparation of (2S,3S,4S,5R,6S)-2-(Methoxycarbonyl)-6-(2-(methylamino)-4-(trifluoromethyl)phenoxy)tetrahydro-2H-pyran-3,4,5-triyl Triacetate

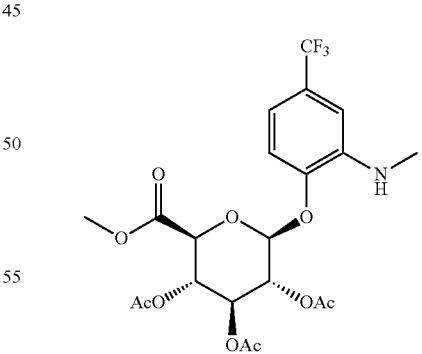

To an ice-cold solution of (2S,3R,4S,5S,6S)-2-(2-formamido-4-(trifluoromethyl)phenoxy)-6-(methoxycarbonyl)tetrahydro-2H-pyran-3,4,5-triyl triacetate (16.4 g, 39.2 mmol) in THF (250 mL) was slowly added borane dimethyl sulfide complex (11.8 mL, 117.6 mmol, 10.0 M solution). The reaction mixture was stirred at room temperature for 3 h and then it was quenched with methanol (100 mL) and the solvent was removed under reduced pressure. The residue was diluted with water (500 mL) and extracted with EtOAc (3×500 mL). The combined organic layers were washed with brine, dried over sodium sulfate, filtered and concentrated under reduced pressure. The crude residue was purified by column chromatography (20% EtOAc in hexanes) to afford the title compound (11.20 g, 70%) as an off-white solid.

Step 20-5—Preparation of (2S,3R,4S,5S,6S)-2-(2-((Chlorocarbonyl)(methyl)amino)-4-(trifluoromethyl)phenoxy)-6-(methoxycarbonyl)tetrahydro-2H-pyran-3,4,5-triyl Triacetate

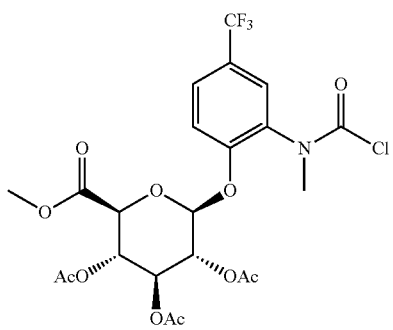 [SMILES: COC(=O)[C@H]1O[C@@H](Oc2ccc(C(F)(F)F)cc2N(C)C(=O)Cl)[C@H](OC(C)=O)[C@@H](OC(C)=O)[C@@H]1OC(C)=O]

A solution of (2S,3S,4S,5R,6S)-2-(methoxycarbonyl)-6-(2-(methylamino)-4-(trifluoromethyl)phenoxy)tetrahydro-2H-pyran-3,4,5-triyl triacetate (1.12 g, 2.16 mmol) in DCM (30.0 mL) was cooled to 0° C. and 15% phosgene in toluene (4.63 mL, 6.48 mmol) was added, followed by triethylamine (5.42 mL, 38.9 mmol). The solution was stirred at 0° C. for 2 h and then warmed to room temperature and stirred at this temperature overnight. The solution was quenched with water (13 mL), the layers were separated and the aqueous layer was extracted with DCM (3×13 mL). The combined organic layers were dried over sodium sulfate, filtered and concentrated under reduced pressure. The crude residue was purified by column chromatography (0-60% EtOAc in hexanes) to afford the title compound (1.08 g, 88%) as a white foam.

Step 20-6—Preparation of (2S,3R,4S,5S,6S)-2-(2-(4-(1-((R)-2-Cyano-1-cyclopentylethyl)-1H-pyrazol-4-yl)-N-methyl-7H-pyrrolo[2,3-d]pyrimidine-7-carboxamido)-4-(trifluoromethyl)phenoxy)-6-(methoxycarbonyl)tetrahydro-2H-pyran-3,4,5-triyl Triacetate

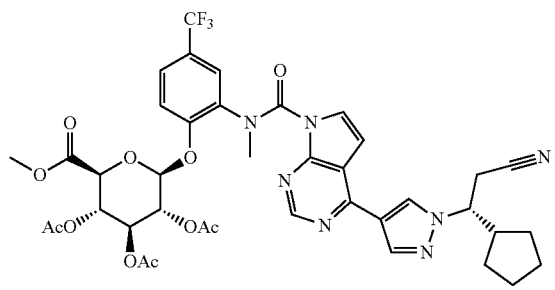 [SMILES: COC(=O)[C@H]1O[C@@H](Oc2ccc(C(F)(F)F)cc2N(C)C(=O)n2ccc3c(-c4cnn([C@H](CC#N)C5CCCC5)c4)ncnc32)[C@H](OC(C)=O)[C@@H](OC(C)=O)[C@@H]1OC(C)=O]

To a solution of ruxolitinib (1.89 mmol) in DCM (18.9 mL) at 0° C. is added triethylamine (0.40 mL, 2.84 mmol), DMAP (23 mg, 0.19 mmol) and (2S,3R,4S,5S,6S)-2-(2-((chlorocarbonyl)(methyl)amino)-4-(trifluoromethyl)phenoxy)-6-(methoxycarbonyl)tetrahydro-2H-pyran-3,4,5-triyl triacetate (1.08 g, 1.89 mmol) as a solution in DCM (18.9 mL). The reaction mixture is stirred at 0° C. for 2 h and then warmed to room temperature and stirred at this temperature overnight. Water is added to the solution (10 mL), the layers are separated and the aqueous layer is extracted with DCM (3×20 mL). The combined organic extracts are dried over sodium sulfate, filtered and concentrated under reduced pressure. The crude residue is purified by column chromatography to afford the title compound.

Step 20-7—Preparation of (2S,3S,4S,5R,6S)-6-(2-(4-(1-((R)-2-Cyano-1-cyclopentylethyl)-1H-pyrazol-4-yl)-N-methyl-7H-pyrrolo[2,3-d]pyrimidine-7-carboxamido)-4-(trifluoromethyl)phenoxy)-3,4,5-trihydroxytetrahydro-2H-pyran-2-carboxylic Acid (Compound III-10)

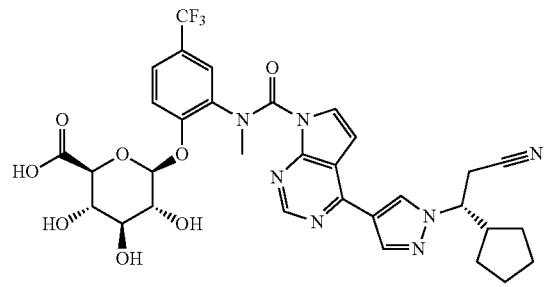

To a solution of (2S,3R,4S,5S,6S)-2-(2-(4-(1-((R)-2-cyano-1-cyclopentylethyl)-1H-pyrazol-4-yl)-N-methyl-7H-pyrrolo[2,3-d]pyrimidine-7-carboxamido)-4-(trifluoromethyl)phenoxy)-6-(methoxycarbonyl)tetrahydro-2H-pyran-3,4,5-triyl triacetate (0.70 mmol) in 1:1:1 methanol (2.3 mL):THF (2.3 mL):water (2.3 mL) is added lithium hydroxide (34 mg, 1.40 mmol). The solution is stirred at room temperature for 30 min and then concentrated under reduced pressure. The crude material is purified by reverse phase column chromatography to afford the title compound.

Example 21

Preparation of (2S,3S,4S,5R,6S)-6-(2-(4-(1-(3-(Cyanomethyl)-1-(ethylsulfonyl)azetidin-3-yl)-1H-pyrazol-4-yl)-N-methyl-7H-pyrrolo[2,3-d]pyrimidine-7-carboxamido)-4-(trifluoromethyl)phenoxy)-3,4,5-trihydroxytetrahydro-2H-pyran-2-carboxylic Acid (Compound III-11)

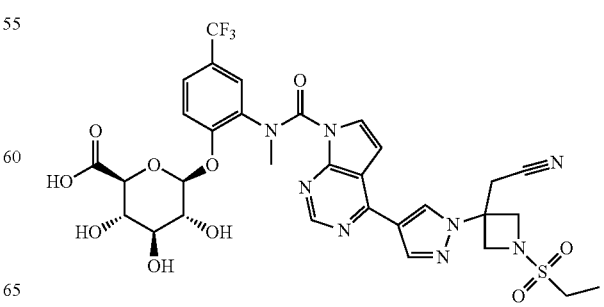

Following the procedures of Example 20 and using baricitinib in Step 20-6, the title compound is prepared.

Example 22

Preparation of (2S,3S,4S,5R,6S)-3,4,5-Trihydroxy-6-(4-methyl-2-(N-methyl-4-(methyl((1r,4S)-4-((N-methylsulfamoyl)methyl)cyclohexyl)amino)-7H-pyrrolo[2,3-d]pyrimidine-7-carboxamido)phenoxy)tetrahydro-2H-pyran-2-carboxylic Acid (Compound III-12)

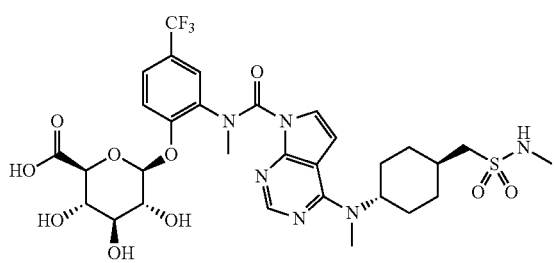

Following the procedures of Example 20 and using oclacitinib in Step 20-6, the title compound is prepared.

Example 23

Preparation of (2S,3S,4S,5R,6S)-6-(4-Chloro-2-(4-(1-((R)-2-cyano-1-cyclopentylethyl)-1H-pyrazol-4-yl)-N-methyl-7H-pyrrolo[2,3-d]pyrimidine-7-carboxamido)phenoxy)-3,4,5-trihydroxytetrahydro-2H-pyran-2-carboxylic Acid (Compound III-13)

Step 23-1—Preparation of (2S,3R,4S,5S,6S)-2-(4-Chloro-2-nitrophenoxy)-6-(methoxycarbonyl)tetrahydro-2H-pyran-3,4,5-triyl Triacetate

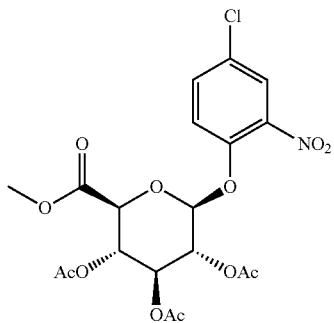 [SMILES: COC(=O)[C@H]1O[C@@H](Oc2ccc(Cl)cc2[N+](=O)[O-])[C@H](OC(C)=O)[C@@H](OC(C)=O)[C@@H]1OC(C)=O]

To an ice-cold solution of 4-chloro-2-nitrophenol (3.5 g, 20.2 mmol) in ACN (250 mL) was added silver(I) oxide (15.0 g, 63.0 mmol), followed by the slow addition of a solution of (2R,3R,4S,5S,6S)-2-bromo-6-(methoxycarbonyl)tetrahydro-2H-pyran-3,4,5-triyl triacetate (10.0 g, 25.2 mmol) in a minimum amount of ACN. The resulting solution was stirred at room temperature for 16 h and then it was filtered through a pad of diatomaceous earth and washed with EtOAc. The filtrate was concentrated under reduced pressure and the crude residue was purified by column chromatography (30% EtOAc in hexanes) to afford the title compound (9.0 g, 73%) as an off-white solid.

Step 23-2—Preparation of (2S,3R,4S,5S,6S)-2-(2-Amino-4-chlorophenoxy)-6-(methoxycarbonyl)tetrahydro-2H-pyran-3,4,5-triyl Triacetate

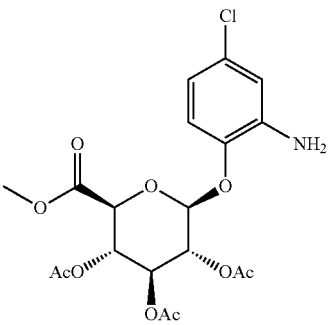 [SMILES: COC(=O)[C@H]1O[C@@H](Oc2ccc(Cl)cc2N)[C@H](OC(C)=O)[C@@H](OC(C)=O)[C@@H]1OC(C)=O]

To a stirred solution of (2S,3R,4S,5S,6S)-2-(4-chloro-2-nitrophenoxy)-6-(methoxycarbonyl)tetrahydro-2H-pyran-3,4,5-triyl triacetate (9.0 g, 18.4 mmol) in THF (250 mL) and acetic acid (25 mL) was added palladium on carbon (0.90 g, 10% w/w). The black solution was stirred under an atmosphere of hydrogen for 16 h and then it was filtered through a pad of diatomaceous earth and washed with EtOAc. The filtrate was concentrated under reduced pressure to afford the title compound (8.6 g, 96%).

Step 23-3—Preparation of (2S,3R,4S,5S,6S)-2-(4-Chloro-2-formamidophenoxy)-6-(methoxycarbonyl)tetrahydro-2H-pyran-3,4,5-triyl Triacetate

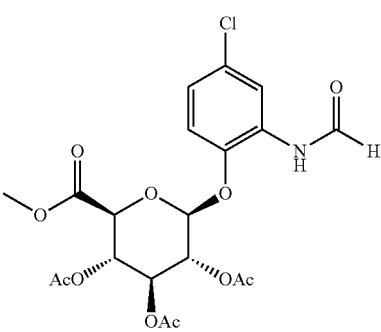 [SMILES: COC(=O)[C@H]1O[C@@H](Oc2ccc(Cl)cc2NC=O)[C@H](OC(C)=O)[C@@H](OC(C)=O)[C@@H]1OC(C)=O]

A stirred solution of formic acid (7.0 mL, 174 mmol) and acetic anhydride (17.0 mL, 174.0 mmol) was heated at 70° C. for 2 h and then cooled to room temperature. A solution of (2S,3R,4S,5S,6S)-2-(2-amino-4-chlorophenoxy)-6-(methoxycarbonyl)tetrahydro-2H-pyran-3,4,5-triyl triacetate (8.0 g, 17.4 mmol) in a minimum amount of THF was then slowly added and the combined mixture was stirred at room temperature for 3 h. The solution was then poured into n-pentane (1.0 L) and stirred for 30 min during which time a precipitate formed. The solid was filtered, washed with n-pentane and dried under high vacuum to afford the title compound (8.1 g, 95%) as an off-white solid.

Step 23-4—Preparation of (2S,3R,4S,5S,6S)-2-(4-Chloro-2-(methylamino)phenoxy)-6-(methoxycarbonyl) tetrahydro-2H-pyran-3,4,5-triyl Triacetate

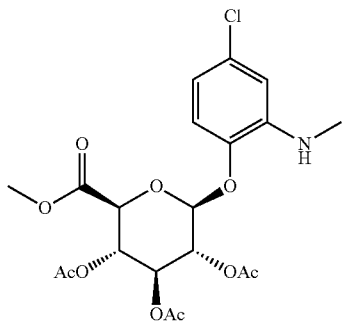

To an ice-cold solution of (2S,3R,4S,5S,6S)-2-(4-chloro-2-formamidophenoxy)-6-(methoxycarbonyl)tetrahydro-2H-pyran-3,4,5-triyl triacetate (8.0 g, 16.4 mmol) in THF (250 mL) was slowly added borane dimethyl sulfide complex (5.0 mL, 49.2 mmol, 10.0 M solution). The reaction mixture was stirred at room temperature for 3 h and then it was quenched with methanol (100 mL) and the solvent was removed under reduced pressure. The residue was diluted with water (500 mL) and extracted with EtOAc (3×500 mL). The combined organic layers were washed with brine, dried over sodium sulfate, filtered and concentrated under reduced pressure. The crude residue was purified by column chromatography (20% EtOAc in hexanes) to afford the title compound (6.4 g, 82%) as an off-white solid.

Step 23-5—Preparation of (2S,3R,4S,5S,6S)-2-(4-Chloro-2-((chlorocarbonyl)(methyl)-amino)phenoxy)-6-(methoxycarbonyl)tetrahydro-2H-pyran-3,4,5-triyl Triacetate

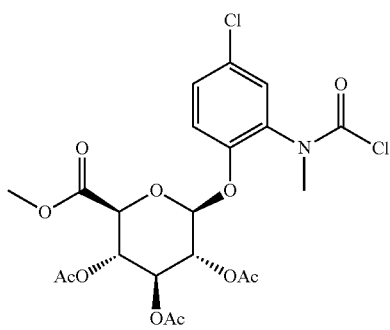 [SMILES: COC(=O)[C@H]1O[C@@H](Oc2ccc(Cl)cc2N(C)C(=O)Cl)[C@H](OC(C)=O)[C@@H](OC(C)=O)[C@@H]1OC(C)=O]

A solution of (2S,3R,4S,5S,6S)-2-(4-chloro-2-(methylamino)phenoxy)-6-(methoxycarbonyl)tetrahydro-2H-pyran-3,4,5-triyl triacetate (1.00 g, 2.05 mmol) in DCM (30 mL) was cooled to 0° C. and 15% phosgene in toluene (4.38 mL, 6.14 mmol) was added, followed by triethylamine (5.14 mL, 36.8 mmol). The reaction mixture was stirred at 0° C. for 2 h and then warmed to room temperature and stirred at this temperature overnight. The solution was quenched with water (13 mL), the layers were separated and the aqueous layer was extracted with DCM (3×13 mL). The combined organic layers were dried over sodium sulfate, filtered and concentrated under reduced pressure. The crude residue was purified by column chromatography (0-60% EtOAc in hexanes) to afford the title compound (1.10 g, 100%) as a white foam.

Step 23-6—Preparation of (2S,3R,4S,5S,6S)-2-(4-Chloro-2-(4-(1-((R)-2-cyano-1-cyclopentylethyl)-1H-pyrazol-4-yl)-N-methyl-7H-pyrrolo[2,3-d]pyrimidine-7-carboxamido)phenoxy)-6-(methoxycarbonyl)tetrahydro-2H-pyran-3,4,5-triyl Triacetate

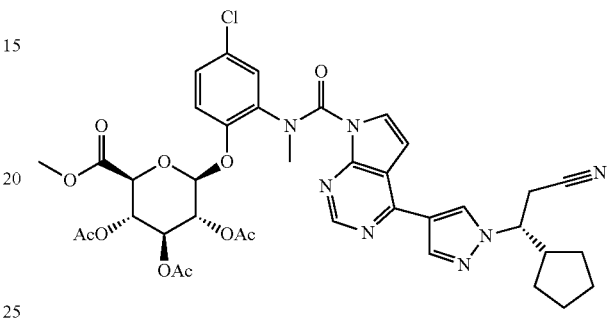

To a solution of ruxolitinib (2.05 mmol) in DCM (20.5 mL) at 0° C. is added triethylamine (0.43 mL, 3.07 mmol), DMAP (25 mg, 0.21 mmol) and (2S,3R,4S,5S,6S)-2-(4-chloro-2-((chlorocarbonyl)(methyl)amino)phenoxy)-6-(methoxycarbonyl)tetrahydro-2H-pyran-3,4,5-triyl triacetate (1.10 g, 2.05 mmol) as a solution in DCM (20.5 mL). The reaction mixture is stirred at 0° C. for 2 h and then warmed to room temperature overnight. Water is added to the solution (10 mL) and the layers are separated. The aqueous layer is extracted with DCM (3×20 mL). The combined organic extracts are dried over sodium sulfate, filtered and concentrated under reduced pressure. The crude residue was purified by column chromatography to afford the title compound.

Step 23-7—Preparation of (2S,3S,4S,5R,6S)-6-(4-Chloro-2-(4-(1-((R)-2-cyano-1-cyclopentylethyl)-1H-pyrazol-4-yl)-N-methyl-7H-pyrrolo[2,3-d]pyrimidine-7-carboxamido)phenoxy)-3,4,5-trihydroxytetrahydro-2H-pyran-2-carboxylic Acid (Compound III-13)

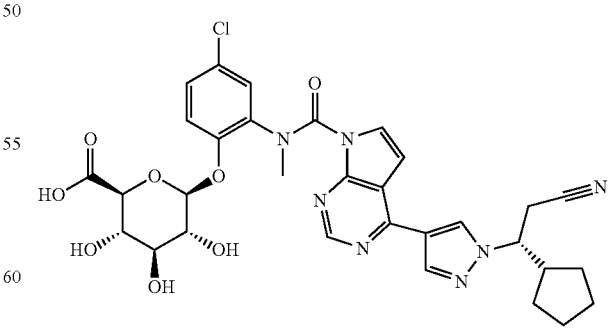

To a solution of (2S,3R,4S,5S,6S)-2-(4-chloro-2-(4-(1-((R)-2-cyano-1-cyclopentylethyl)-1H-pyrazol-4-yl)-N-methyl-7H-pyrrolo[2,3-d]pyrimidine-7-carboxamido)phenoxy)-6-(methoxycarbonyl)tetrahydro-2H-pyran-3,4,5-triyl triacetate (0.55 mmol) in 1:1:1 methanol (1.8 mL):THF (1.8 mL):water (1.8 mL) is added lithium hydroxide (14 mg, 0.60 mmol). The solution is stirred at room temperature for 30 min and the reaction mixture is concentrated under reduced pressure. The crude material is purified by reverse phase column chromatography to afford the title compound.

Example 24

Preparation of (2S,3S,4S,5R,6S)-6-(4-Chloro-2-(4-(1-(3-(cyanomethyl)-1-(ethylsulfonyl)azetidin-3-yl)-1H-pyrazol-4-yl)-N-methyl-7H-pyrrolo[2,3-d]pyrimidine-7-carboxamido)phenoxy)-3,4,5-trihydroxytetrahydro-2H-pyran-2-carboxylic Acid (Compound III-14)

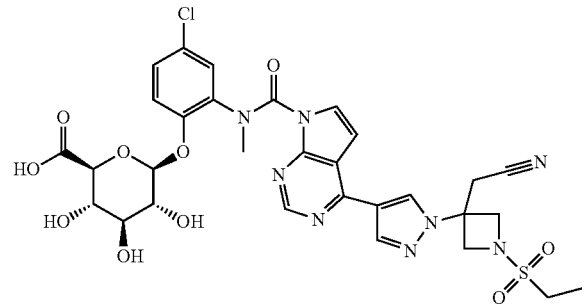 [SMILES: CCS(=O)(=O)N1CC(CC#N)(n2cc(-c3ncnc4c3ccn4C(=O)N(C)c3cc(Cl)ccc3O[C@@H]3O[C@H](C(=O)O)[C@@H](O)[C@H](O)[C@H]3O)cn2)C1]

Following the procedures of Example 23 and using baricitinib in Step 23-6, the title compound is prepared.

Example 25

Preparation of (2S,3S,4S,5R,6S)-6-(4-Chloro-2-(N-methyl-4-(methyl((1r,4S)-4-((N-methylsulfamoyl)methyl)cyclohexyl)amino)-7H-pyrrolo[2,3-d]pyrimidine-7-carboxamido)phenoxy)-3,4,5-trihydroxytetrahydro-2H-pyran-2-carboxylic Acid (Compound III-15)

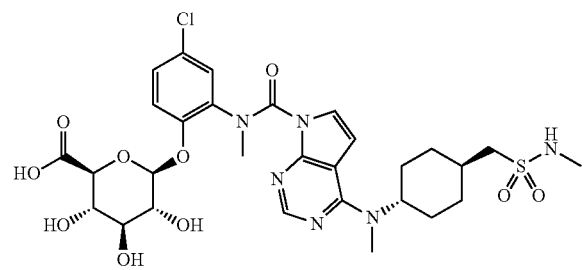 [SMILES: CNS(=O)(=O)C[C@H]1CC[C@H](N(C)c2ncnc3c2ccn3C(=O)N(C)c2cc(Cl)ccc2O[C@@H]2O[C@H](C(=O)O)[C@@H](O)[C@H](O)[C@H]2O)CC1]

Following the procedures of Example 23 and using oclacitinib in Step 23-6, the title compound is prepared.

Example 26

Preparation of (2S,3S,4S,5R,6S)-6-(2-((4-(1-((R)-2-Cyano-1-cyclopentylethyl)-1H-pyrazol-4-yl)-N-methyl-7H-pyrrolo[2,3-d]pyrimidine-7-carboxamido)methyl)phenoxy)-3,4,5-trihydroxytetrahydro-2H-pyran-2-carboxylic Acid (Compound III-16)

Step 26-1—Preparation of (2S,3R,4S,5S,6S)-2-(2-Formylphenoxy)-6-(methoxycarbonyl)tetrahydro-2H-pyran-3,4,5-triyl Triacetate

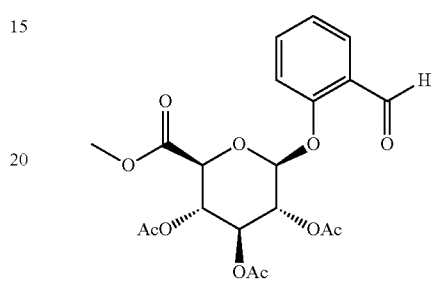

To an ice-cold solution of 2-hydroxybenzaldehyde (1.65 g, 13.51 mmol) in ACN (100 mL) and silver(I) oxide (3.10 g) was added (2R,3R,4S,5S,6S)-2-bromo-6-(methoxycarbonyl)tetrahydro-2H-pyran-3,4,5-triyl triacetate (5.0 g, 12.25 mmol). The resulting reaction was stirred at room temperature for 16 h. After completion of reaction (as determined by TLC monitoring), the reaction mixture was filtered through a sintered-glass funnel and the material collected in the funnel was washed with EtOAc (100 mL). The filtrate was evaporated under reduced pressure and crude residue was purified over silica gel (100-200 mesh) to afford the title compound as an off-white solid (54% LCMS purity).

Step 26-2—Preparation of (2S,3S,4S,5R,6S)-2-(Methoxycarbonyl)-6-(2-((methylamino)methyl)phenoxy)tetrahydro-2H-pyran-3,4,5-triyl Triacetate

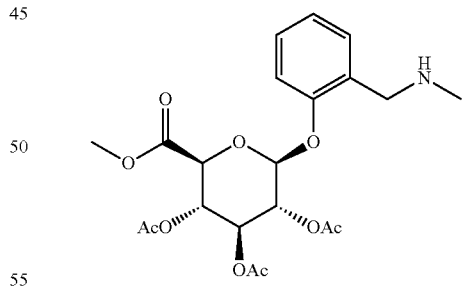

To an ice-cold solution of (2S,3R,4S,5S,6S)-2-(2-formylphenoxy)-6-(methoxycarbonyl)tetrahydro-2H-pyran-3,4,5-triyl triacetate (1.0 g, 2.28 mmol) in IPA:chloroform (30:70 mL) was added methylamine (2.28 mL, 4.56 mmol, 2M in THF), followed by the addition of acetic acid (1.0 mL). The resulting reaction mixture was stirred for 30 minutes at 0° C. and then silica gel (1.0 g) and sodium borohydride (216 mg, 5.7 mmol) were added and the reaction mixture was stirred at room temperature for 2 h. After completion of reaction (as determined by TLC monitoring, reaction mixture was fil- tered through a sintered-glass funnel and the material collected in the funnel was washed with DCM. The filtrate was washed with water and brine solution, dried over sodium sulfate, filtered and concentrated under reduced pressure to afford the title compound as beige solid, which was used in the next step without further purification.

Step 26-3—Preparation of (2S,3R,4S,5S,6S)-2-(2-((4-(1-((R)-2-Cyano-1-cyclopentylethyl)-1H-pyrazol-4-yl)-N-methyl-7H-pyrrolo[2,3-d]pyrimidine-7-carboxamido)methyl)phenoxy)-6-(methoxycarbonyl)tetrahydro-2H-pyran-3,4,5-triyl Triacetate N

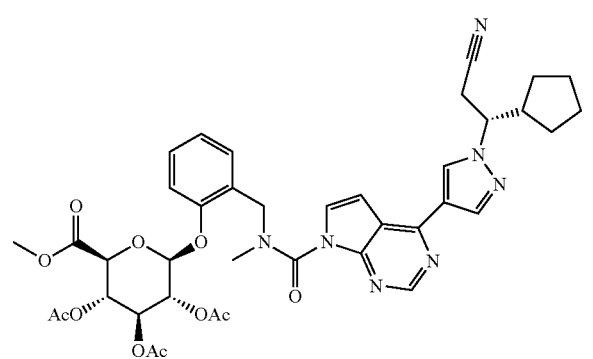 [SMILES: COC(=O)[C@H]1O[C@@H](Oc2ccccc2CN(C)C(=O)n2ccc3c(-c4cnn([C@H](CC#N)C5CCCC5)c4)ncnc32)[C@H](OC(C)=O)[C@@H](OC(C)=O)[C@@H]1OC(C)=O]

To an ice-cold solution of (2S,3S,4S,5R,6S)-2-(methoxycarbonyl)-6-(2-((methylamino)methyl)phenoxy)tetrahydro-2H-pyran-3,4,5-triyl triacetate (570 mg, 1.25 mmol) in DCM (25.0 mL) is added triethylamine (0.50 mL, 3.75 mmol), followed by the dropwise addition of 4-nitrophenyl (R)-4-(1-(2-cyano-1-cyclopentylethyl)-1H-pyrazol-4-yl)-7H-pyrrolo[2,3-d]pyrimidine-7-carboxylate (600 mg, 1.25 mmol) dissolved in minimum amount of DCM. The resulting reaction mixture is stirred at 0° C. for 1 h. After completion of reaction (as determined by TLC monitoring), the solvent is evaporated under reduced pressure and crude residue is purified by column chromatography on silica gel to afford the title compound.

Step 26-4—Preparation of (2S,3S,4S,5R,6S)-6-(2-((4-(1-((R)-2-Cyano-1-cyclopentylethyl)-1H-pyrazol-4-yl)-N-methyl-7H-pyrrolo[2,3-d]pyrimidine-7-carboxamido)methyl)phenoxy)-3,4,5-trihydroxytetrahydro-2H-pyran-2-carboxylic Acid (Compound III-16)

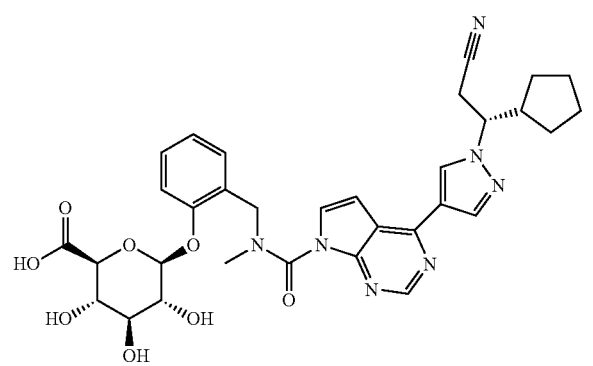 [SMILES: CN(Cc1ccccc1O[C@@H]1O[C@H](C(=O)O)[C@@H](O)[C@H](O)[C@H]1O)C(=O)n1ccc2c(-c3cnn([C@H](CC#N)C4CCCC4)c3)ncnc21]

To an ice-cold solution of (2S,3R,4S,5S,6S)-2-(2-((4-(1-((R)-2-cyano-1-cyclopentylethyl)-1H-pyrazol-4-yl)-N-methyl-7H-pyrrolo[2,3-d]pyrimidine-7-carboxamido)methyl)-phenoxy)-6-(methoxy carbonyl)tetrahydro-2H-pyran-3,4,5-triyl triacetate (0.72 mmol) in methanol (30.0 mL) and water (6.0 mL) is added DIPEA (3.0 mL) in a dropwise manner. The resulting reaction mixture is stirred at 0° C. for 8 h. After completion of reaction (as determined by TLC and LCMS monitoring), the solvent is evaporated under reduced pressure and the crude residue is purified by RP-HPLC to afford the title compound.

Example 27

Preparation of (2S,3S,4S,5R,6S)-6-(2-((4-(1-(3-(Cyanomethyl)-1-(ethylsulfonyl)azetidin-3-yl)-1H-pyrazol-4-yl)-N-methyl-7H-pyrrolo[2,3-d]pyrimidine-7-carboxamido)methyl)phenoxy)-3,4,5-trihydroxytetrahydro-2H-pyran-2-carboxylic Acid (Compound III-17)

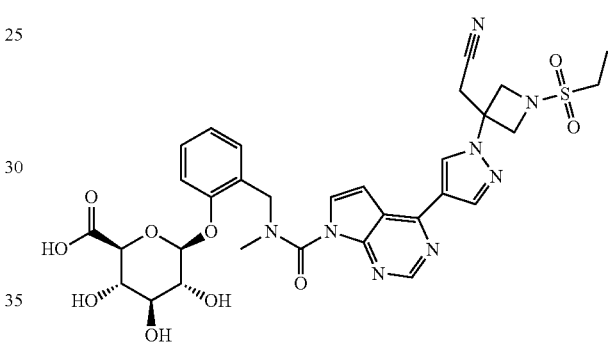

Following the procedures of Example 26 and using 4-nitrophenyl 4-(1-(3-(cyanomethyl)-1-(ethylsulfonyl)azetidin-3-yl)-1H-pyrazol-4-yl)-7H-pyrrolo[2,3-d]pyrimidine-7-carboxylate in Step 26-3, the title compound is prepared.

Example 28

Preparation of (2S,3S,4S,5R,6S)-3,4,5-Trihydroxy-6-(2-((N-methyl-4-(methyl((1r,4S)-4-((N-methylsulfamoyl)methyl)cyclohexyl)amino)-7H-pyrrolo[2,3-d]pyrimidine-7-carboxamido)methyl)phenoxy)tetrahydro-2H-pyran-2-carboxylic Acid (Compound III-18)

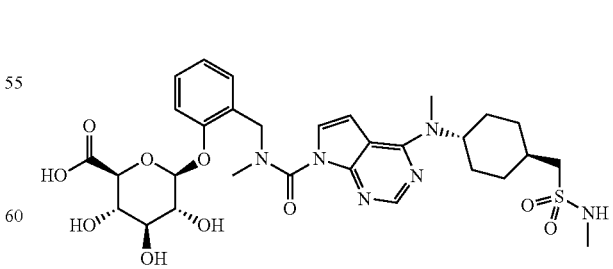

Following the procedures of Example 26 and using 4-nitrophenyl 4-(methyl((1r,4r)-4-((N-methylsulfamoyl)methyl)cyclohexyl)amino)-7H-pyrrolo[2,3-d]pyrimidine-7-carboxylate in Step 26-3, the title compound is prepared.

Example 29

Preparation of (2S,3S,4S,5R,6S)-6-(2-((4-(1-((R)-2-Cyano-1-cyclopentylethyl)-1H-pyrazol-4-yl)-N-methyl-7H-pyrrolo[2,3-d]pyrimidine-7-carboxamido)methyl)-4-nitrophenoxy)-3,4,5-trihydroxytetrahydro-2H-pyran-2-carboxylic Acid (Compound III-19)

Step 29-1—Preparation of (2S,3R,4S,5S,6S)-2-(2-Formyl-4-nitrophenoxy)-6-(methoxycarbonyl)tetrahydro-2H-pyran-3,4,5-triyl Triacetate

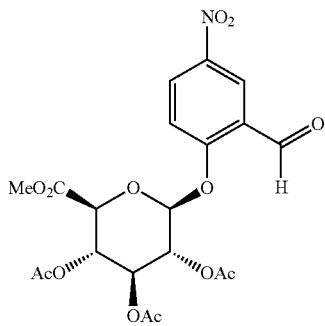 [SMILES: COC(=O)[C@H]1O[C@@H](Oc2ccc([N+](=O)[O-])cc2C=O)[C@H](OC(C)=O)[C@@H](OC(C)=O)[C@@H]1OC(C)=O]

To an ice-cold solution of 2-hydroxy-5-nitrobenzaldehyde (4.40 g, 26.44 mmol) in 100 mL of ACN was added silver(I) oxide (8.80 g, 37.77 mmol), followed by addition of (2R,3R,4S,5S,6S)-2-bromo-6-(methoxycarbonyl)tetrahydro-2H-pyran-3,4,5-triyl triacetate (15.0 g, 37.77 mmol) at 0° C. The reaction mixture was stirred at room temperature for 16 h. After completion of reaction (as determined by TLC), the mixture was filtered through diatomaceous earth and the solvent was evaporated under reduced pressure to afford the crude product as dark brown solid. The crude residue was purified by column chromatography (100-200 mesh, 30% EtOAc:Hexane) to afford title compound (11.0 g, 60%) as off-white solid.

Step 29-2—Preparation (2S,3S,4S,5R,6S)-2-(Methoxycarbonyl)-6-(2-((methylamino)methyl)-4-nitrophenoxy)tetrahydro-2H-pyran-3,4,5-triyl Triacetate

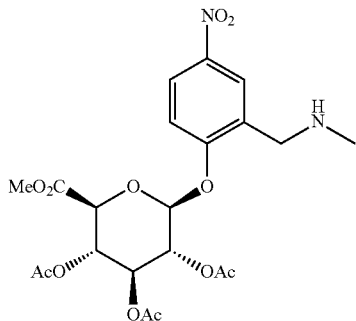 [SMILES: CNCc1cc([N+](=O)[O-])ccc1O[C@@H]1O[C@H](C(=O)OC)[C@@H](OC(C)=O)[C@H](OC(C)=O)[C@H]1OC(C)=O]

To an ice-cold solution of (2S,3R,4S,5S,6S)-2-(2-formyl-4-nitrophenoxy)-6-(methoxycarbonyl)tetrahydro-2H-pyran-3,4,5-triyl triacetate (1.50 g, 3.10 mmol) and silica gel (2.0 g) in 20 mL of IPA:chloroform (3:17) was added methylamine (3.10 mL, 6.20 mmol, 2.0 M solution in THF) and acetic acid (1.50 mL). The resulting reaction mixture was stirred at 0° C. for 30 min followed by the portion-wise addition of triacetoxy borohydride (0.98 g, 4.65 mmol). The resulting reaction mixture was stirred at room temperature for 16 h. After the completion of reaction (as determined by TLC monitoring), the reaction mixture was quenched with ice-cold water and filtered through a sintered-glass funnel. The filtrate was concentrated under reduced pressure to afford the crude title compound (1.30 g, 84%), which was used in the next step without further purification.

Step 29-3—Preparation of (2S,3R,4S,5S,6S)-2-(2-((4-(1-((R)-2-Cyano-1-cyclopentylethyl)-1H-pyrazol-4-yl)-N-methyl-7H-pyrrolo[2,3-d]pyrimidine-7-carboxamido)methyl)-4-nitrophenoxy)-6-(methoxycarbonyl)tetrahydro-2H-pyran-3,4,5-triyl Triacetate

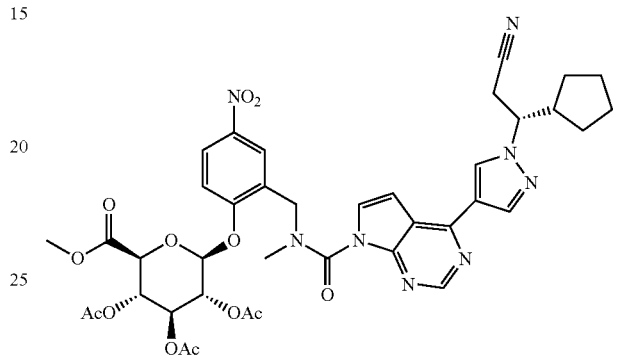

To an ice-cold solution of (2S,3S,4S,5R,6S)-2-(methoxycarbonyl)-6-(2-((methylamino)methyl)-4-nitrophenoxy)tetrahydro-2H-pyran-3,4,5-triyl triacetate (0.94 g, 1.89 mmol) in DCM (50 mL) is added 4-nitrophenyl (R)-4-(1-(2-cyano-1-cyclopentylethyl)-1H-pyrazol-4-yl)-7H-pyrrolo[2,3-d]pyrimidine-7-carboxylate and triethylamine (5.67 mmol). The resulting reaction mixture is then stirred at room temperature for 8 h. After the completion of reaction (as determined by TLC monitoring), reaction mixture is diluted with DCM and washed subsequently with a saturated aqueous solution of ammonium chloride and brine. The organic layer is dried over anhydrous sodium sulfate, filtered and evaporated under reduced pressure to give a crude residue which is further purified by column chromatography to afford title compound.

Step 29-4—Preparation of (2S,3S,4S,5R,6S)-6-(2-((4-(1-((R)-2-Cyano-1-cyclopentylethyl)-1H-pyrazol-4-yl)-N-methyl-7H-pyrrolo[2,3-d]pyrimidine-7-carboxamido)methyl)-4-nitrophenoxy)-3,4,5-trihydroxytetrahydro-2H-pyran-2-carboxylic Acid (Compound III-19)

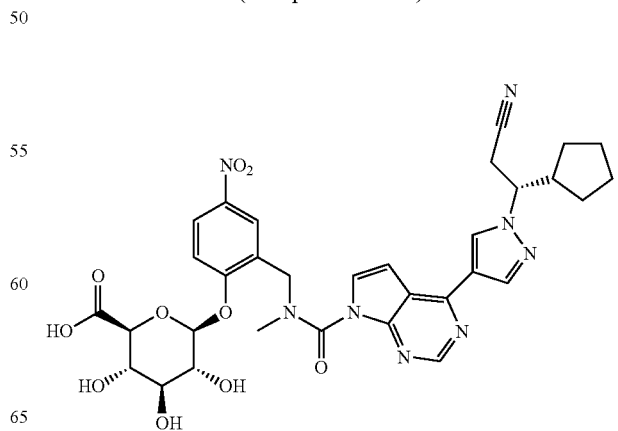

To an ice-cold solution of (2S,3R,4S,5S,6S)-2-(2-((4-(1-((R)-2-cyano-1-cyclopentylethyl)-1H-pyrazol-4-yl)-N-methyl-7H-pyrrolo[2,3-d]pyrimidine-7-carboxamido)methyl)-4-nitrophenoxy)-6-(methoxycarbonyl)tetrahydro-2H-pyran-3,4,5-triyl triacetate (400 mg, 0.48 mmol) in methanol (25 mL) and water (5 mL) is added DIPEA (2.50 mL). The resulting reaction mixture is stirred at room temperature for 16 h. After the completion of the reaction (as determined by LCMS monitoring), the reaction mixture is evaporated under reduced pressure to give a residue that is lyophilized to remove excess DIPEA. The crude residue is purified by RP-HPLC to afford the title compound.

Example 30

Preparation of (2S,3S,4S,5R,6S)-6-(2-((4-(1-(3-(Cyanomethyl)-1-(ethylsulfonyl)azetidin-3-yl)-1H-pyrazol-4-yl)-N-methyl-7H-pyrrolo[2,3-d]pyrimidine-7-carboxamido)methyl)-4-nitrophenoxy)-3,4,5-trihydroxytetrahydro-2H-pyran-2-carboxylic Acid (Compound III-20)

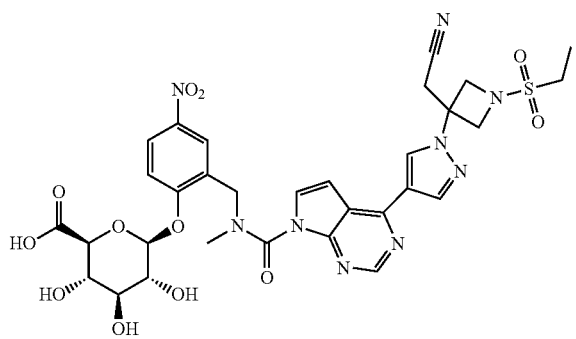 [SMILES: CCS(=O)(=O)N1CC(CC#N)(n2cc(-c3ncnc4c3ccn4C(=O)N(C)Cc3cc([N+](=O)[O-])ccc3O[C@@H]3O[C@H](C(=O)O)[C@@H](O)[C@H](O)[C@H]3O)cn2)C1]

Following the procedures of Example 29 and using 4-nitrophenyl 4-(1-(3-(cyanomethyl)-1-(ethylsulfonyl)azetidin-3-yl)-1H-pyrazol-4-yl)-7H-pyrrolo[2,3-d]pyrimidine-7-carboxylate in Step 29-3, the title compound is prepared.

Example 31

Preparation of (2S,3S,4S,5R,6S)-3,4,5-Trihydroxy-6-(2-((N-methyl-4-(methyl((1r,4S)-4-((N-methylsulfamoyl)methyl)cyclohexyl)amino)-7H-pyrrolo[2,3-d]pyrimidine-7-carboxamido)methyl)-4-nitrophenoxy)tetrahydro-2H-pyran-2-carboxylic Acid (Compound III-21)

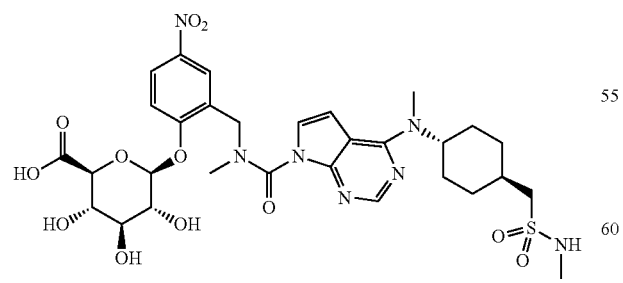

Following the procedures of Example 29 and using 4-nitrophenyl 4-(methyl((1r,4r)-4-((N-methylsulfamoyl)methyl)cyclohexyl)amino)-7H-pyrrolo[2,3-d]pyrimidine-7-carboxylate in Step 29-3, the title compound is prepared.

Example 32

Preparation of (2S,3S,4S,5R,6S)-6-(((2-((4-(1-((R)-2-Cyano-1-cyclopentylethyl)-1H-pyrazol-4-yl)-N-methyl-7H-pyrrolo[2,3-d]pyrimidine-7-carboxamido)methyl)phenyl)carbamoyl)oxy)-3,4,5-trihydroxytetrahydro-2H-pyran-2-carboxylic Acid (Formula IV-1)

Step 32-1—Preparation of N-Methyl-1-(2-nitrophenyl)methanamine

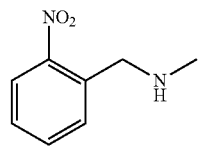

To a stirred solution of 2-nitrobenzaldehyde (10 g, 66.23 mmol) in methanol (200 mL) was added methylamine (8.0 mL, 33% solution in methanol). The reaction mixture was stirred at room temperature for 30 min and then cooled to 0° C. Sodium borohydride (1.26 g, 33.11 mmol) was added portion-wise and the reaction mixture was left to warm to room temperature and stirred at room temperature for 1 h. The reaction was then quenched with ice water (300 mL) and methanol. The resulting mixture was extracted with DCM (2×500 mL) and the combined organic layers were dried over sodium sulfate, filtered and concentrated under reduced pressure to afford the title compound (8.90 g, 81%).

Step 32-2—Preparation of tert-Butyl Methyl(2-nitrobenzyl)carbamate

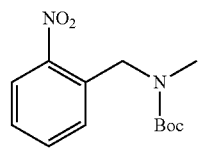 [SMILES: CN(Cc1ccccc1[N+](=O)[O-])C(=O)OC(C)(C)C]

To an ice-cold solution of N-methyl-1-(2-nitrophenyl)methanamine (8.90 g, 53.6 mmol) in DCM (150 mL) was added triethylamine (16.2 mL, 160.8 mmol) and di-tert-butyl dicarbonate (29.34 g, 134.0 mmol). The reaction mixture was warmed to room temperature and stirred at room temperature for 16 h. The reaction was then quenched with water (300 mL) and extracted with DCM (2×500 mL). The combined organic layers were dried over sodium sulfate, filtered and concentrated under reduced pressure. The crude residue was purified by column chromatography (5% EtOAc in hexanes) to afford the title compound (12.9 g, 92%).

Step 32-3—Preparation of tert-Butyl (2-Aminobenzyl)(methyl)carbamate

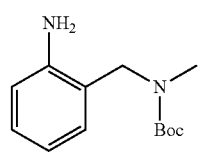 [SMILES: CN(Cc1ccccc1N)C(=O)OC(C)(C)C]

To a stirred solution of tert-butyl methyl(2-nitrobenzyl)carbamate (12.90 g, 48.49 mmol) in methanol (200 mL) was added palladium on carbon (5.0 g). The reaction mixture was stirred at room temperature for 16 h under an atmosphere of hydrogen. The reaction mixture was then filtered through a pad of diatomaceous earth, washed with methanol and concentrated under reduced pressure to afford the title compound (10.60 g, 93%) as a pale-yellow oil.

Step 32-4—Preparation of tert-Butyl (2-Isocyanatobenzyl)(methyl)carbamate

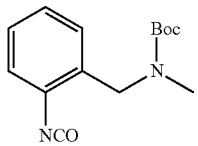

To an ice-cold solution of tert-butyl (2-aminobenzyl)(methyl)carbamate (5.0 g, 11.01 mmol) in toluene (100 mL) was slowly added triethylamine (8.90 mL, 63.56 mmol) and triphosgene (2.5 g, 8.47 mmol) under inert atmosphere. The resulting reaction mixture was heated to 80° C. and stirred at this temperature for 3 h. The reaction mixture was then cooled to room temperature, filtered and washed with toluene. The filtrate was concentrated under reduced pressure to afford the title compound (6.0 g), which was used without further purification.

Step 32-5—Preparation of (2S,3R,4S,5S,6S)-2-(((2-(((tert-Butoxycarbonyl)(methyl)amino)methyl)phenyl)carbamoyl)oxy)-6-(methoxycarbonyl) tetrahydro-2H-pyran-3,4,5-triyl Triacetate

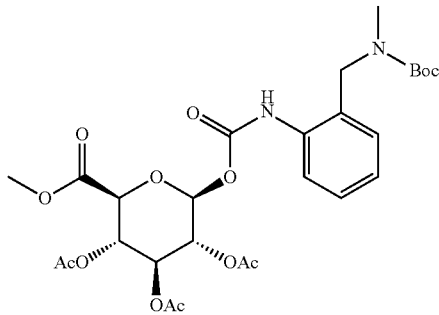 [SMILES: COC(=O)[C@H]1O[C@@H](OC(=O)Nc2ccccc2CN(C)C(=O)OC(C)(C)C)[C@H](OC(C)=O)[C@@H](OC(C)=O)[C@@H]1OC(C)=O]

To a stirred solution of tert-butyl (2-isocyanatobenzyl)(methyl)carbamate (5.0 g, 19.08 mmol) and (3R,4S,5S,6S)-2-hydroxy-6-(methoxycarbonyl)tetrahydro-2H-pyran-3,4,5-triyl triacetate (4.80 g, 14.5 mmol) in toluene (150 mL) was slowly added triethylamine (2.04 mL, 14.5 mmol). The reaction mixture was stirred at room temperature for 16 h and then concentrated under reduced pressure. The crude residue was purified by column chromatography (45% EtOAc in hexanes) to afford the title compound (6.20 g, 54%) as a white solid.

Step 32-6—Preparation of (2S,3S,4S,5R,6S)-2-(Methoxycarbonyl)-6-(((2-((methylamino)methyl)phenyl)carbamoyl)oxy)tetrahydro-2H-pyran-3,4,5-triyl Triacetate

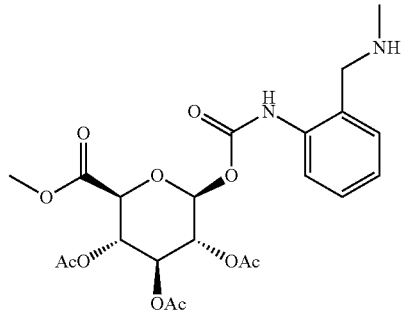

To an ice-cold solution of (2S,3R,4S,5S,6S)-2-(((2-(((tert-butoxycarbonyl)(methyl)amino)methyl)phenyl)carbamoyl)oxy)-6-(methoxycarbonyl)tetrahydro-2H-pyran-3,4,5-triyl triacetate (2.0 g, 3.36 mmol) in DCM (50 mL) was slowly added TFA (29.6 mL). The reaction mixture was stirred at 0° C. for 1 h and then concentrated under reduced pressure to afford the title compound (1.20 g, 58%) as a TFA salt.

Step 32-7—Preparation of (2S,3R,4S,5S,6S)-2-(((2-((4-(1-((R)-2-Cyano-1-cyclopentylethyl)-1H-pyrazol-4-yl)-N-methyl-7H-pyrrolo[2,3-d]pyrimidine-7-carboxamido)methyl)phenyl)carbamoyl)oxy)-6-(methoxycarbonyl)tetrahydro-2H-pyran-3,4,5-triyl Triacetate

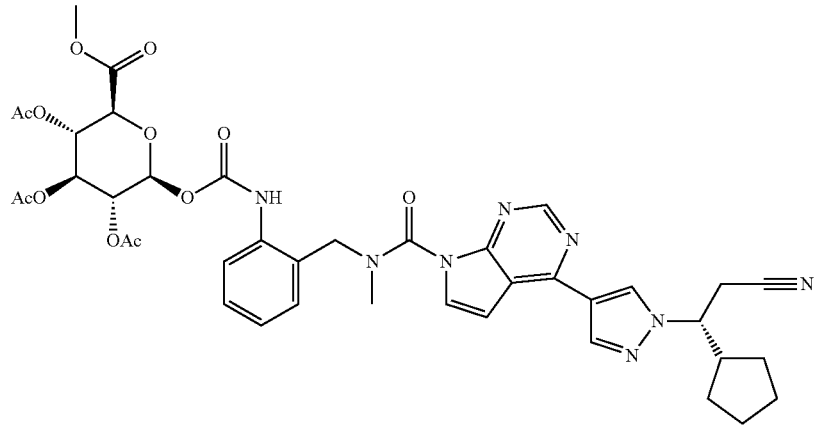 [SMILES: COC(=O)[C@H]1O[C@@H](OC(=O)Nc2ccccc2CN(C)C(=O)n2ccc3c(-c4cnn([C@H](CC#N)C5CCCC5)c4)ncnc32)[C@H](OC(C)=O)[C@@H](OC(C)=O)[C@@H]1OC(C)=O]

To a stirred solution of (2S,3S,4S,5R,6S)-2-(methoxycarbonyl)-6-(((2-((methylamino)methyl)phenyl)carbamoyl)oxy)tetrahydro-2H-pyran-3,4,5-triyl triacetate (1.0 g, 2.0 mmol) in DCM (25 mL) is slowly added a solution of 4-nitrophenyl (R)-4-(1-(2-cyano-1-cyclopentylethyl)-1H-pyrazol-4-yl)-7H-pyrrolo[2,3-d]pyrimidine-7-carboxylate (2.00 mmol) in DCM (25 mL). The reaction mixture is subsequently cooled to 0° C. and DIPEA (3.2 g, 24.0 mmol) is added dropwise. The solution is stirred at 0° C. for 1 h and then concentrated under reduced pressure. The crude residue is purified by column chromatography to afford the title compound.

Step 32-8—Preparation of (2S,3S,4S,5R,6S)-6-(((2-((4-(1-((R)-2-Cyano-1-cyclopentylethyl)-1H-pyrazol-4-yl)-N-methyl-7H-pyrrolo[2,3-d]pyrimidine-7-carboxamido)methyl)phenyl)carbamoyl)oxy)-3,4,5-trihydroxytetrahydro-2H-pyran-2-carboxylic Acid (Compound IV-1)

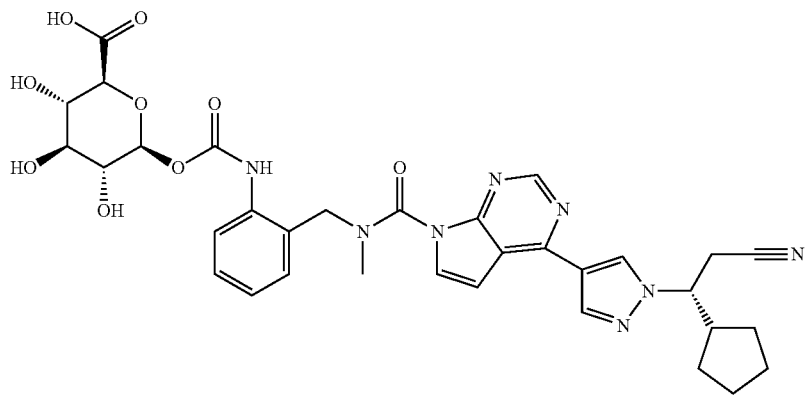 [SMILES: CN(Cc1ccccc1NC(=O)O[C@@H]1O[C@H](C(=O)O)[C@@H](O)[C@H](O)[C@H]1O)C(=O)n1ccc2c(-c3cnn([C@H](CC#N)C4CCCC4)c3)ncnc21]

To an ice-cold solution of (2S,3R,4S,5S,6S)-2-(((2-((4-(1-((R)-2-cyano-1-cyclopentylethyl)-1H-pyrazol-4-yl)-N-methyl-7H-pyrrolo[2,3-d]pyrimidine-7-carboxamido)methyl)phenyl)carbamoyl)oxy)-6-(methoxycarbonyl)tetrahydro-2H-pyran-3,4,5-triyl triacetate (0.5 mmol) in methanol (12.73 mL) and water (4.1 mL) is added DIPEA (2.1 mL). The reaction mixture is warmed to room temperature and stirred at room temperature for 16 h. The reaction mixture is then concentrated under reduced pressure and the crude residue was purified by RP-HPLC to afford the title compound.

Example 33

Preparation of (2S,3S,4S,5R,6S)-6-(((2-((4-(1-(3-(Cyanomethyl)-1-(ethylsulfonyl)azetidin-3-yl)-1H-pyrazol-4-yl)-N-methyl-7H-pyrrolo[2,3-d]pyrimidine-7-carboxamido)methyl)phenyl)carbamoyl)oxy)-3,4,5-trihydroxytetrahydro-2H-pyran-2-carboxylic Acid (Compound IV-2)

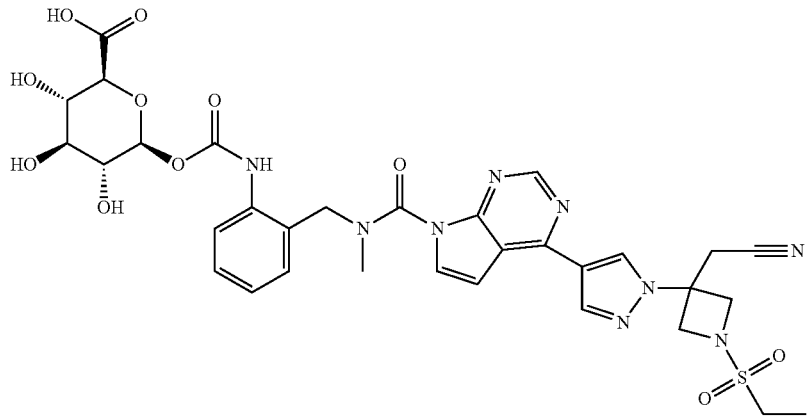 [SMILES: CCS(=O)(=O)N1CC(CC#N)(n2cc(-c3ncnc4c3ccn4C(=O)N(C)Cc3ccccc3NC(=O)O[C@@H]3O[C@H](C(=O)O)[C@@H](O)[C@H](O)[C@H]3O)cn2)C1]

Following the procedures of Example 32 and using 4-nitrophenyl 4-(1-(3-(cyanomethyl)-1-(ethylsulfonyl)azetidin-3-yl)-1H-pyrazol-4-yl)-7H-pyrrolo[2,3-d]pyrimidine-7-carboxylate in Step 32-7, the title compound is prepared.

Example 34

Preparation of (2S,3S,4S,5R,6S)-3,4,5-Trihydroxy-6-(((2-((N-methyl-4-(methyl((1r,4r)-4-((N-methylsulfamoyl)methyl)cyclohexyl)amino)-7H-pyrrolo[2,3-d]pyrimidine-7-carboxamido)methyl)phenyl)carbamoyl)oxy)tetrahydro-2H-pyran-2-carboxylic Acid (Compound IV-3)

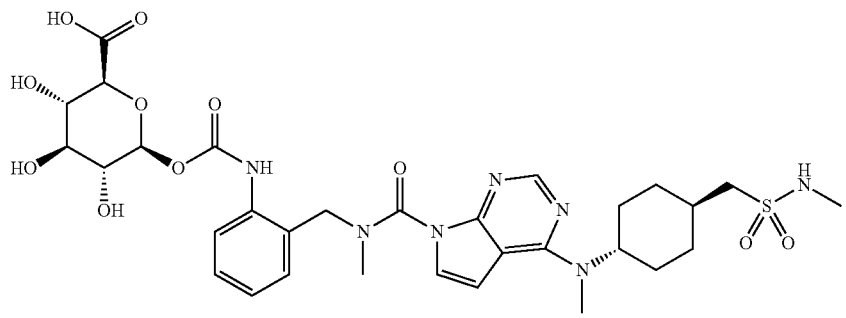 [SMILES: CNS(=O)(=O)C[C@H]1CC[C@H](N(C)c2ncnc3c2ccn3C(=O)N(C)Cc2ccccc2NC(=O)O[C@@H]2O[C@H](C(=O)O)[C@@H](O)[C@H](O)[C@H]2O)CC1]

Following the procedures of Example 32 and using 4-nitrophenyl 4-(methyl((1r,4r)-4-((N-methylsulfamoyl)methyl)cyclohexyl)amino)-7H-pyrrolo[2,3-d]pyrimidine-7-carboxylate in Step 32-7, the title compound is prepared.

Example 35

Preparation of (2S,3S,4S,5R,6S)-6-(2-((((2-(4-(1-((R)-2-Cyano-1-cyclopentylethyl)-1H-pyrazol-4-yl)-N-methyl-7H-pyrrolo[2,3-d]pyrimidine-7-carboxamido)ethyl)(methyl)carbamoyl)oxy)methyl)phenoxy)-3,4,5-trihydroxytetrahydro-2H-pyran-2-carboxylic Acid (Compound V-1)

Step 35-1—Preparation of (2S,3R,4S,5S,6S)-2-(2-Formylphenoxy)-6-(methoxycarbonyl)tetrahydro-2H-pyran-3,4,5-triyl Triacetate To an ice-cold solution of 2-hydroxybenzaldehyde (1.65 g, 13.51 mmol) in ACN (100 mL) was added silver(I) oxide (3.10 g, 13.37 mmol) followed by the slow addition of a solution of (2R,3R,4S,5S,6S)-2-bromo-6-(methoxycarbonyl)tetrahydro-2H-pyran-3,4,5-triyl triacetate (5.0 g, 12.25 mmol) in a minimum amount of ACN. The resulting solution was stirred at room temperature for 16 h and then it was filtered through a pad of diatomaceous earth and washed with EtOAc. The filtrate was concentrated under reduced pressure and the crude residue was purified by column chromatography (20% EtOAc in hexanes) to afford the title compound (3.4 g, 62%) as an off-white solid.

Step 35-2—Preparation of (2S,3R,4S,5S,6S)-2-(2-(Hydroxymethyl)phenoxy)-6-(methoxycarbonyl)tetrahydro-2H-pyran-3,4,5-triyl Triacetate

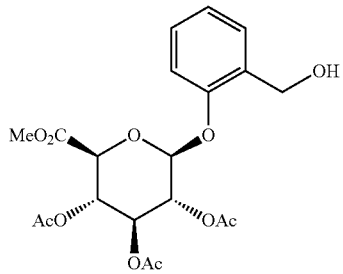

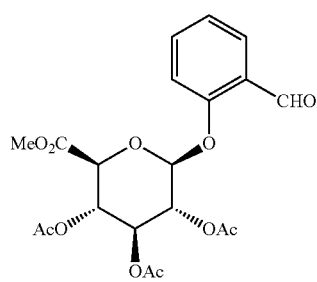 [SMILES: COC(=O)[C@H]1O[C@@H](Oc2ccccc2C=O)[C@H](OC(C)=O)[C@@H](OC(C)=O)[C@@H]1OC(C)=O]

To an ice-cold solution of (2S,3R,4S,5S,6S)-2-(2-formylphenoxy)-6-(methoxycarbonyl)tetrahydro-2H-pyran-3,4,5-triyl triacetate (1.0 g, 2.2 mmol) and silica gel (100-200 mesh, 6.6 g) in a 3:7 mixture of IPA and chloroform (150 mL) was slowly added sodium borohydride (249 mg, 6.6 mmol). The reaction mixture was stirred at 0° C. for 2 h and then quenched with ice-cold water (250 mL) and filtered through a sintered-glass funnel. The layers of the biphasic solution were separated and the aqueous layer was extracted with DCM (3×200 mL). The combined organic layers were dried over sodium sulfate, filtered and evaporated under reduced pressure to afford the title compound (1.0 g, 99%), which was used without further purification.

Step 35-3—Preparation of (2S,3S,4S,5R,6S)-2-(Methoxycarbonyl)-6-(2-((((4-nitrophenoxy)carbonyl)oxy)methyl)phenoxy)tetrahydro-2H-pyran-3,4,5-triyl Triacetate

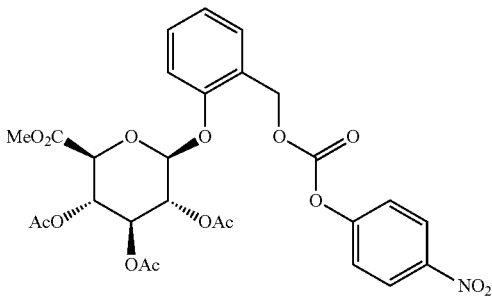 [SMILES: COC(=O)[C@H]1O[C@@H](Oc2ccccc2COC(=O)Oc2ccc([N+](=O)[O-])cc2)[C@H](OC(C)=O)[C@@H](OC(C)=O)[C@@H]1OC(C)=O]

To a stirred solution of (2S,3R,4S,5S,6S)-2-(2-(hydroxymethyl)phenoxy)-6-(methoxycarbonyl)tetrahydro-2H-pyran-3,4,5-triyl Triacetate (1.0 g, 2.2 mmol) and triethylamine (1.26 mL, 9.0 mmol) in DCM (50 mL) was slowly added a solution of p-nitrophenyl chloroformate (549 mg, 2.7 mmol) in a minimum amount of DCM and the resulting reaction mixture was stirred at room temperature for 2 h. The solution was concentrated under reduced pressure and the crude residue was purified by column chromatography (40% EtOAc in hexanes) to afford the title compound (850 mg, 57%).

Step 35-4—Preparation of (2S,3S,4S,5R,6S)-2-(Methoxycarbonyl)-6-(2-(((methyl(2-(methylamino)ethyl)carbamoyl)oxy)methyl)phenoxy)tetrahydro-2H-pyran-3,4,5-triyl Triacetate

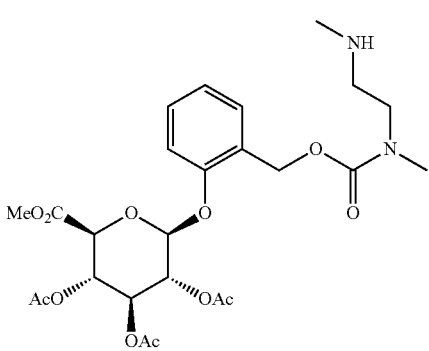 [SMILES: CNCCN(C)C(=O)OCc1ccccc1O[C@@H]1O[C@H](C(=O)OC)[C@@H](OC(C)=O)[C@H](OC(C)=O)[C@H]1OC(C)=O]

To a solution of (2S,3S,4S,5R,6S)-2-(methoxycarbonyl)-6-(2-((((4-nitrophenoxy)carbonyl)oxy)methyl)phenoxy)tetrahydro-2H-pyran-3,4,5-triyl triacetate (700 mg, 1.15 mmol) in DCM (50 mL) was added triethylamine (0.48 mL, 3.4 mmol) and N,N-dimethylethane-1,2-diamine (0.618 mL, 5.75 mmol) at room temperature. The resulting reaction mixture was stirred at room temperature for 2 h and then concentrated under reduced pressure. The crude residue was purified by column chromatography (4% methanol-DCM) to afford the title compound (450 mg, 69%).

Step 35-5—Preparation of (2S,3R,4S,5S,6S)-2-(2-(((((2-(4-(1-((R)-2-Cyano-1-cyclopentylethyl)-1H-pyrazol-4-yl)-N-methyl-7H-pyrrolo[2,3-d]pyrimidine-7-carboxamido)ethyl)(methyl)carbamoyl)oxy)methyl)phenoxy)-6-(methoxycarbonyl)tetrahydro-2H-pyran-3,4,5-triyl Triacetate

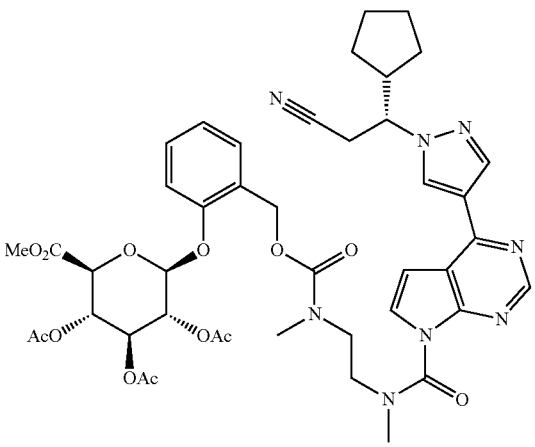 [SMILES: COC(=O)[C@H]1O[C@@H](Oc2ccccc2COC(=O)N(C)CCN(C)C(=O)n2ccc3c(-c4cnn([C@H](CC#N)C5CCCC5)c4)ncnc32)[C@H](OC(C)=O)[C@@H](OC(C)=O)[C@@H]1OC(C)=O]

To an ice-cold solution of (2S,3S,4S,5R,6S)-2-(methoxycarbonyl)-6-(2-(((methyl(2-(methylamino) ethyl)carbamoyl)oxy)methyl)phenoxy)tetrahydro-2H-pyran-3,4,5-triyl triacetate (400 mg, 0.45 mmol) and 4-nitrophenyl (R)-4-(1-(2-cyano-1-cyclopentylethyl)-1H-pyrazol-4-yl)-7H-pyrrolo[2,3-d]pyrimidine-7-carboxylate (0.35 mmol) in DCM (20 mL) is slowly added triethylamine (0.435 mL, 2.2 mmol). The reaction mixture is stirred at room temperature for 16 h and then concentrated under reduced pressure. The crude residue is purified by column chromatography to afford the title compound.

Step 35-6—Preparation of (2S,3S,4S,5R,6S)-6-(2-(((((2-(4-(1-((R)-2-Cyano-1-cyclopentylethyl)-1H-pyrazol-4-yl)-N-methyl-7H-pyrrolo[2,3-d]pyrimidine-7-carboxamido)ethyl)(methyl)carbamoyl)oxy)methyl)phenoxy)-3,4,5-trihydroxytetrahydro-2H-pyran-2-carboxylic Acid (Compound V-1)

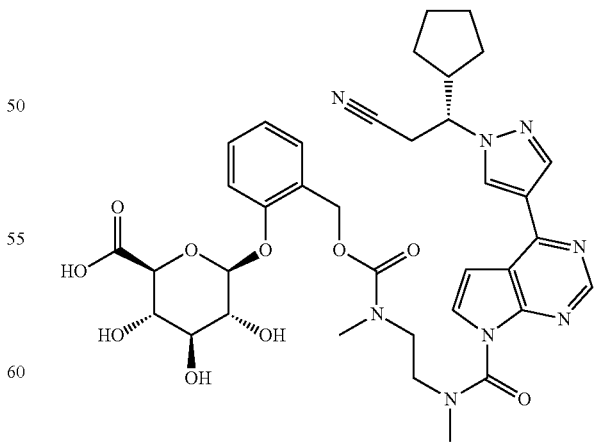

To an ice-cold solution of (2S,3R,4S,5S,6S)-2-(2-(((((2-(4-(1-((R)-2-cyano-1-cyclopentylethyl)-1H-pyrazol-4-yl)-N-methyl-7H-pyrrolo[2,3-d]pyrimidine-7-carboxamido)ethyl)(methyl)carbamoyl)oxy)methyl)phenoxy)-6-

(methoxycarbonyl)tetrahydro-2H-pyran-3,4,5-triyl triacetate (0.34 mmol) in methanol (25 mL) and water (5 mL) is added DIPEA (2.50 mL). The reaction mixture is stirred at room temperature for 16 h and then evaporated under reduced pressure. The crude residue is lyophilized to remove excess amounts of DIPEA and then purified by RP-HPLC to afford the title compound.

Example 36

Preparation of (2S,3S,4S,5R,6S)-6-(2-((((2-(4-(1-(3-(Cyanomethyl)-1-(ethylsulfonyl)azetidin-3-yl)-1H-pyrazol-4-yl)-N-methyl-7H-pyrrolo[2,3-d]pyrimidine-7-carboxamido)ethyl)(methyl)carbamoyl)oxy)methyl)phenoxy)-3,4,5-trihydroxytetrahydro-2H-pyran-2-carboxylic Acid (Compound V-2)

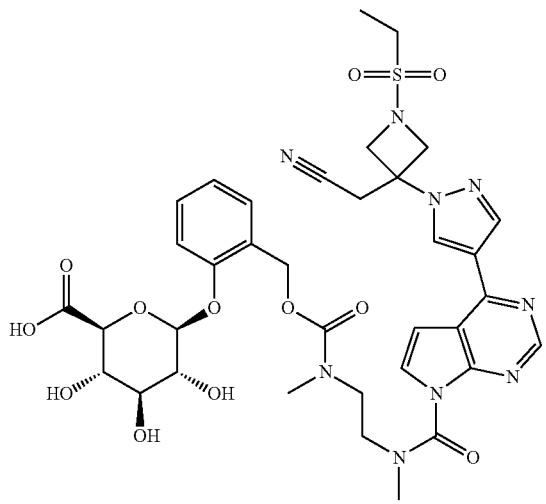 [SMILES: CCS(=O)(=O)N1CC(CC#N)(n2cc(-c3ncnc4c3ccn4C(=O)N(C)CCN(C)C(=O)OCc3ccccc3O[C@@H]3O[C@H](C(=O)O)[C@@H](O)[C@H](O)[C@H]3O)cn2)C1]

Following the procedures of Example 35 and using 4-nitrophenyl 4-(1-(3-(cyanomethyl)-1-(ethylsulfonyl)azetidin-3-yl)-1H-pyrazol-4-yl)-7H-pyrrolo[2,3-d]pyrimidine-7-carboxylate in Step 35-5, the title compound is prepared.

Example 37

Preparation of (2S,3S,4S,5R,6S)-3,4,5-Trihydroxy-6-(2-(((methyl(2-(N-methyl-4-(methyl((1r,4r)-4-((N-methylsulfamoyl)methyl)cyclohexyl)amino)-7H-pyrrolo[2,3-d]pyrimidine-7-carboxamido)ethyl)carbamoyl)oxy)methyl)phenoxy)tetrahydro-2H-pyran-2-carboxylic Acid (Compound V-3)

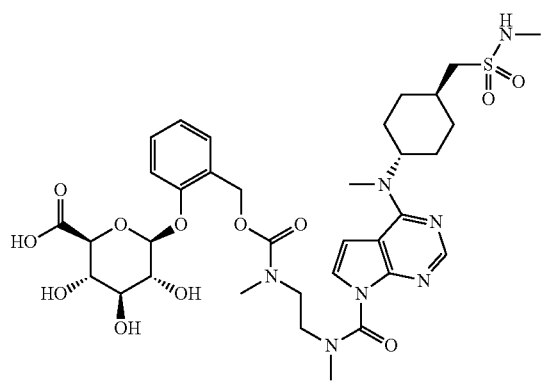 [SMILES: CNS(=O)(=O)C[C@H]1CC[C@H](N(C)c2ncnc3c2ccn3C(=O)N(C)CCN(C)C(=O)OCc2ccccc2O[C@@H]2O[C@H](C(=O)O)[C@@H](O)[C@H](O)[C@H]2O)CC1]

Following the procedures of Example 35 and using 4-nitrophenyl 4-(methyl((1r,4r)-4-((N-methylsulfamoyl)methyl)cyclohexyl)amino)-7H-pyrrolo[2,3-d]pyrimidine-7-carboxylate in Step 35-5, the title compound is prepared.

Example 38

Preparation of (2S,3S,4S,5R,6S)-6-((2-((((2-(4-(1-((R)-2-Cyano-1-cyclopentylethyl)-1H-pyrazol-4-yl)-N-methyl-7H-pyrrolo[2,3-d]pyrimidine-7-carboxamido)ethyl)(methyl)carbamoyl)oxy)methyl)pyridin-3-yl)oxy)-3,4,5-trihydroxytetrahydro-2H-pyran-2-carboxylic Acid (Compound V-4)

Step 38-1—Preparation of (2S,3R,4S,5S,6S)-2-((2-Formylpyridin-3-yl)oxy)-6-(methoxycarbonyl)tetrahydro-2H-pyran-3,4,5-triyl Triacetate

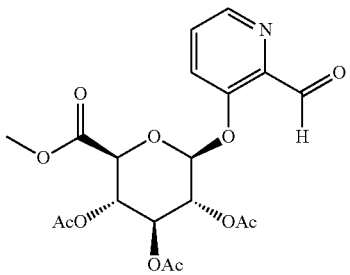 [SMILES: COC(=O)[C@H]1O[C@@H](Oc2cccnc2C=O)[C@H](OC(C)=O)[C@@H](OC(C)=O)[C@@H]1OC(C)=O]

To a flame-dried flask was added 3-hydroxypicolinaldehyde (2.5 g, 20.32 mmol), silver(I) carbonate (11.2 g, 40.65 mmol) and (2R,3R,4S,5S,6S)-2-bromo-6-(methoxycarbonyl)tetrahydro-2H-pyran-3,4,5-triyl triacetate (12.1 g, 30.49 mmol) in toluene under an inert atmosphere. The reaction mixture was heated to 80° C. and stirred at this temperature for 16 h. The solution was then filtered through a pad of diatomaceous earth and washed with EtOAc. The filtrate was concentrated under reduced pressure and the crude residue was purified by column chromatography (40% EtOAc:Hexane) to afford the title compound (4.8 g, 54%).

Step 38-2—Preparation of (2S,3R,4S,5S,6S)-2-((2-(Hydroxymethyl)pyridin-3-yl)oxy)-6-(methoxycarbonyl)tetrahydro-2H-pyran-3,4,5-triyl Triacetate

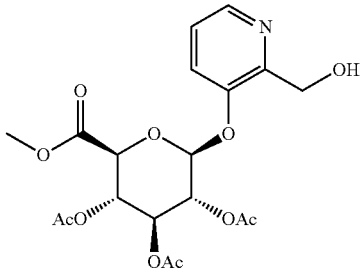 [SMILES: COC(=O)[C@H]1O[C@@H](Oc2cccnc2CO)[C@H](OC(C)=O)[C@@H](OC(C)=O)[C@@H]1OC(C)=O]

To an ice-cold solution of (2S,3R,4S,5S,6S)-2-((2-formylpyridin-3-yl)oxy)-6-(methoxycarbonyl)tetrahydro-2H-pyran-3,4,5-triyl triacetate (4.8 g, 10.92 mmol) and silica gel (4.8 g, 100-200 mesh) in a 3:7 mixture of IPA and chloroform (200 mL) was added sodium borohydride (1.10 g, 29.49 mmol) over a period of 5 min. The reaction mixture was stirred at 0° C. for 2 h and then ice-water (50 mL) was added to quench the reaction. The mixture was filtered and the filtrate was extracted with EtOAc (3×150 mL) and the combined organic layers were dried over sodium sulfate, filtered and concentration under reduced pressure. The resulting crude product was re-crystallized from ethanol to afford the title compound (3.4 g, 71%) as an off-white solid.

Step 38-3—Preparation of (2S,3S,4S,5R,6S)-2-(Methoxycarbonyl)-6-((2-(((methyl(2-(methylamino)ethyl)carbamoyl)oxy)methyl)pyridin-3-yl)oxy)tetrahydro-2H-pyran-3,4,5-triyl Triacetate

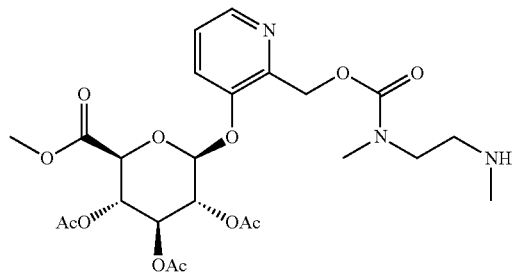

To a solution of (2S,3R,4S,5S,6S)-2-((2-(hydroxymethyl)pyridin-3-yl)oxy)-6-(methoxycarbonyl)tetrahydro-2H-pyran-3,4,5-triyl triacetate (0.20 g, 0.45 mmol) in DCM (4.53 mL) was added 1,1'-carbonyldiimidazole (0.11 g, 0.68 mmol) and the reaction mixture was stirred at room temperature for 30 min. N,N'-Dimethylethylenediamine (0.39 mL, 3.62 mmol) was added and the solution was stirred at room temperature for 1 h (at which time, LC/MS indicated formation of the product). The solution was diluted with DCM and washed with water and saturated brine solution. The organic layer was dried over sodium sulfate, filtered and concentrated under reduced pressure to afford the title compound as a yellow oil that was used without further purification.

Step 38-4—Preparation of (2S,3R,4S,5S,6S)-2-((2-((((2-(4-(1-((R)-2-Cyano-1-cyclopentylethyl)-1H-pyrazol-4-yl)-N-methyl-7H-pyrrolo[2,3-d]pyrimidine-7-carboxamido)ethyl)(methyl)carbamoyl)oxy)methyl)pyridin-3-yl)oxy)-6-(methoxycarbonyl)tetrahydro-2H-pyran-3,4,5-triyl Triacetate

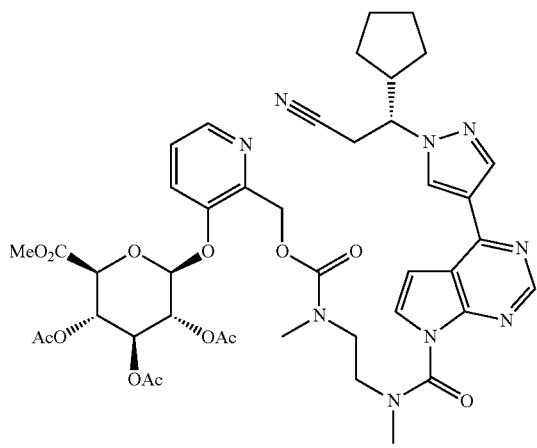 [SMILES: COC(=O)[C@H]1O[C@@H](Oc2cccnc2COC(=O)N(C)CCN(C)C(=O)n2ccc3c(-c4cnn([C@H](CC#N)C5CCCC5)c4)ncnc32)[C@H](OC(C)=O)[C@@H](OC(C)=O)[C@@H]1OC(C)=O]

To a solution of (2S,3S,4S,5R,6S)-2-(methoxycarbonyl)-6-((2-(((methyl(2-(methylamino)ethyl)carbamoyl)oxy)methyl)pyridin-3-yl)oxy)tetrahydro-2H-pyran-3,4,5-triyl triacetate (0.25 g, 0.45 mmol) dissolved in DCM (4.50 mL) is added 4-nitrophenyl (R)-4-(1-(2-cyano-1-cyclopentylethyl)-1H-pyrazol-4-yl)-7H-pyrrolo[2,3-d]pyrimidine-7-carboxylate (0.45 mmol) in one portion. The reaction mixture is stirred at room temperature for 12 h and then concentrated under reduced pressure to give the title compound.

Step 38-5—Preparation of (2S,3S,4S,5R,6S)-6-((2-((((2-(4-(1-((R)-2-Cyano-1-cyclopentylethyl)-1H-pyrazol-4-yl)-N-methyl-7H-pyrrolo[2,3-d]pyrimidine-7-carboxamido)ethyl)(methyl)carbamoyl)oxy)methyl)pyridin-3-yl)oxy)-3,4,5-trihydroxytetrahydro-2H-pyran-2-carboxylic Acid (Compound V-4)

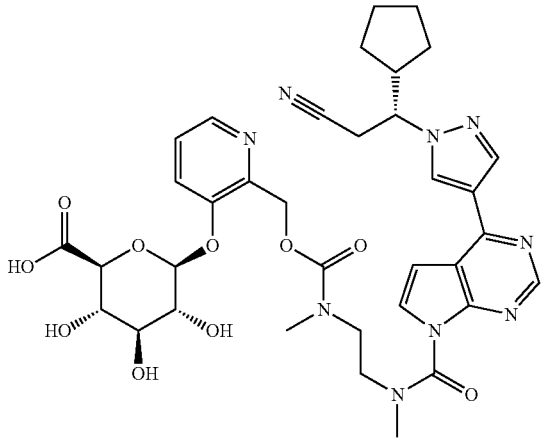 [SMILES: CN(CCN(C)C(=O)n1ccc2c(-c3cnn([C@H](CC#N)C4CCCC4)c3)ncnc21)C(=O)OCc1ncccc1O[C@@H]1O[C@H](C(=O)O)[C@@H](O)[C@H](O)[C@H]1O]

To a solution of (2S,3R,4S,5S,6S)-2-((2-((((2-(4-(1-((R)-2-cyano-1-cyclopentylethyl)-1H-pyrazol-4-yl)-N-methyl-7H-pyrrolo[2,3-d]pyrimidine-7-carboxamido)ethyl)(methyl)carbamoyl)oxy)methyl)pyridin-3-yl)oxy)-6-(methoxycarbonyl)tetrahydro-2H-pyran-3,4,5-triyl triacetate (0.45 mmol) in a 3:1 mixture of THF (3.38 mL) and water (1.13 mL) is added lithium hydroxide (0.05 g, 2.25 mmol). The reaction mixture is stirred at room temperature for 30 min and then concentrated under reduced pressure. The crude residue is purified by reverse phase column chromatography to afford the title compound.

Example 39

Preparation of (2S,3S,4S,5R,6S)-6-((2-((((2-(4-(1-(3-(Cyanomethyl)-1-(ethylsulfonyl)azetidin-3-yl)-1H-pyrazol-4-yl)-N-methyl-7H-pyrrolo[2,3-d]pyrimidine-7-carboxamido)ethyl)(methyl)carbamoyl)oxy)methyl)pyridin-3-yl)oxy)-3,4,5-trihydroxytetrahydro-2H-pyran-2-carboxylic Acid (Compound V-5)

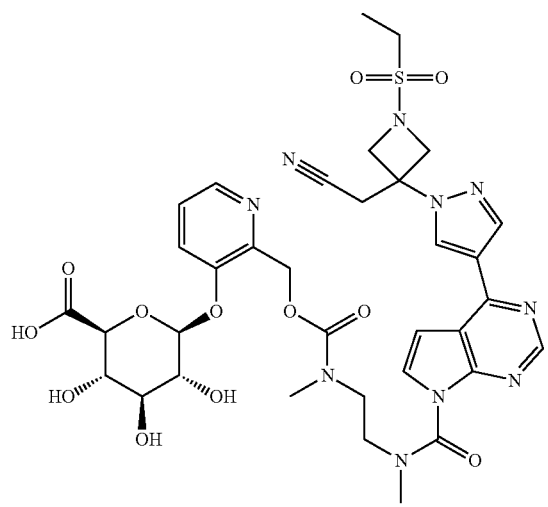 [SMILES: CCS(=O)(=O)N1CC(CC#N)(n2cc(-c3ncnc4c3ccn4C(=O)N(C)CCN(C)C(=O)OCc3ncccc3O[C@@H]3O[C@H](C(=O)O)[C@@H](O)[C@H](O)[C@H]3O)cn2)C1]

Following the procedures of Example 38 and using 4-nitrophenyl 4-(1-(3-(cyanomethyl)-1-(ethylsulfonyl)azetidin-3-yl)-1H-pyrazol-4-yl)-7H-pyrrolo[2,3-d]pyrimidine-7-carboxylate in Step 38-4, the title compound is prepared.

Example 40

Preparation of (2S,3S,4S,5R,6S)-3,4,5-Trihydroxy-6-((2-(((methyl(2-(N-methyl-4-(methyl((1r,4r)-4-((N-methylsulfamoyl)methyl)cyclohexyl)amino)-7H-pyrrolo[2,3-d]pyrimidine-7-carboxamido)ethyl)carbamoyl)oxy)methyl)pyridin-3-yl)oxy)tetrahydro-2H-pyran-2-carboxylic Acid (Compound V-6)

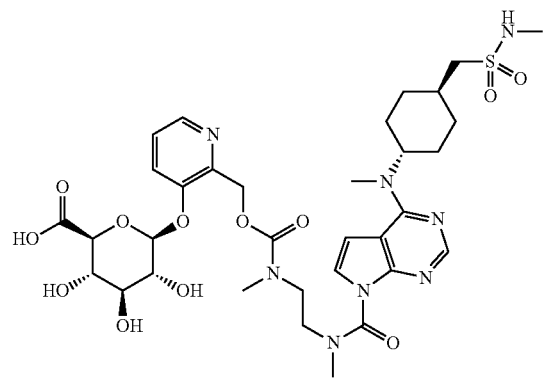 [SMILES: CNS(=O)(=O)C[C@H]1CC[C@H](N(C)c2ncnc3c2ccn3C(=O)N(C)CCN(C)C(=O)OCc2ncccc2O[C@@H]2O[C@H](C(=O)O)[C@@H](O)[C@H](O)[C@H]2O)CC1]

Following the procedures of Example 38 and using 4-nitrophenyl 4-(methyl((1r,4r)-4-((N-methylsulfamoyl)methyl)cyclohexyl)amino)-7H-pyrrolo[2,3-d]pyrimidine-7-carboxylate in Step 38-4, the title compound is prepared.

Example 41

Rat Colon Fecal Homogenate Stability Assay

The compounds of the present invention contain a glucuronide prodrug moiety that is expected to be cleaved by β-glucuronidase enzyme to release a JAK inhibitor (e.g., ruxolitinib, baricitinib or oclacitinib). The objective of this assay was to determine the half-life for compounds of the present invention in the presence of β-glucuronidase in rat colon feces.

Following sacrifice of a naïve male Sprague Dawley rat (~300 g) by cardiac puncture exsanguination, the colon was ligated and removed to an anaerobic chamber (AS-580, Anaerobe Systems). The fecal content was removed within the chamber and was diluted 1:10 with phosphate buffer (1 gram fecal content to 9 mL phosphate buffer) and the resulting mixture was homogenized using a handheld Omni Tissue Master. The fecal homogenate was centrifuged at 2000 g for 10 min to remove bulk material and the supernatant was removed and used for the incubations.

DMSO stock solutions (10 mM) of the test compounds and sulfasalazine (control) were prepared. Sulfasalazine was used as a positive control to confirm viability of the fecal supernatant-homogenate (see, e.g., Azad Khan et al., *Clinical Science* (1983) 64, 349-354). If the in vitro half-life (T½) for sulfasalazine in the fecal sample was less than 30 min, the fecal sample was deemed to be viable and in true anaerobic conditions. However, if the T½ for sulfasalazine was greater than 30 min, the fecal sample was typically contaminated with oxygen and was not viable. The final substrate concentration of each assay was 10 μM. Reactions were started by adding a 5 μL aliquot of diluted test compound stock solution into 300 μL of rat fecal supernatant-homogenate. At 0, 15, 50, 85 and 120 min post reaction initiation, a 50 μL aliquot was removed and added to a mixture of 200 μL of acetonitrile with 3% formic acid and an internal standard. All samples were centrifuged at 2000 g for 10 min after which 50 μL of supernatant was diluted into 150 μL of water for analysis on an LC-MS system. In vitro half-lives (T½) for the test compounds were calculated as follows: T½=0.693/elimination rate constant. The data for various representative compounds of the present invention are shown in Table 41-1.

TABLE 41-1

| Compound No. (JAK Inhibitor) | T½ (min) | Time (min) for Complete Conversion (JAK Inhibitor to reach 10 μM) |
| --- | --- | --- |
| VII-1 (Ruxolitinib) | <5 | 120 |
| VII-2 (Baricitinib) | <5 | 100 |
| VII-3 (Oclacitinib) | <5 | 105 |

The data in Table 41-1 demonstrate that all of the compounds of the present invention tested in this assay had a half-life in the presence of rat colon fecal homogenate of less than about 5 minutes. The data also show that such compounds were completely cleaved in about 100 to 120 minutes.

Example 42

Oral Pharmacokinetics in Mouse Assay

When cleaved by β-glucuronidase enzyme, the compounds of the present invention release a JAK inhibitor (e.g., ruxolitinib, baricitinib or oclacitinib). The object of this assay was to determine JAK inhibitor exposure (AUC$_{0-6\,h}$) in colon tissue and plasma following oral dosing of compounds of the present invention in mice.

Male Balb/c mice (n=2/time point) received a single PO oral gavage dose (5 mg/kg in 1:20 mixture of 5% DMSO and 1% HPMC) of the test compound. At 0.5, 2, 6 and 24 h post-dosing, mice were sacrificed via cardiac puncture exsanguination and blood samples were taken and placed into sample tubes (Microtainer, Becton, Dickinson and Company) containing sodium fluoride and then placed on ice. Plasma was obtained by centrifugation (Eppendorf centrifuge, 5804R) for 4 min at approximately 12,000 rpm at 4° C.

The colons were removed from the exsanguinated mice and the colon fecal contents were gently removed. The colons were flushed with saline and patted dry. The colons were then homogenized in 3× volume of sterile water using a tissue homogenizer (Precellys homogenizer, Bertin Instruments) at approximately 4° C. All samples were stored at −80° C. for later bioanalysis.

The concentration of JAK inhibitor (e.g., ruxolitinib, baricitinib or oclacitinib) in each sample was determined as follows: the plasma and colon homogenate samples were vortexed, combined with a 50 µL aliquot of rat plasma, extracted with 200 µL of ACN containing an internal standard and quantified against the internal standard by LC-MS. An area-under-the-concentration curve (AUC$_{0-6\,h}$) was calculated for plasma and colon test compound and liberated JAK inhibitor. A key parameter to assess suitability for localized delivery of the JAK inhibitor to the colon was the JAK inhibitor colon to plasma AUC ratio. The data for various representative compounds of the present invention are shown in Table 42-1.

TABLE 42-1

| Compound No. (JAK Inhibitor) | Plasma AUC (µg * hr/mL) | Colon AUC (µg * hr/g) | Colon/ Plasma AUC Ratio |
|---|---|---|---|
| VII-1 (Ruxolitinib) | 0.217 | 7.4 | 34 |
| VII-2 (Baricitinib) | 0.117 | 17.3 | 148 |
| VII-3 (Oclacitinib) | 0.141 | 13.5 | 96 |

The data in Table 42-1 demonstrate that the JAK inhibitor exposure (AUC-6 hr) following oral administration of the compound of the invention to mice was significantly higher in colon tissue compared to plasma.

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statutes and regulations, all publications, patents and patent applications cited herein are hereby incorporated by reference in their entirety to the same extent as if each document had been individually incorporated by reference herein.

What is claimed is:

1. A compound of formula I:

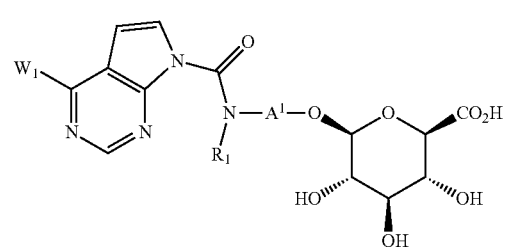

wherein
$R^1$ is hydrogen or $C_{1-3}$alkyl;
$W^1$ is selected from:

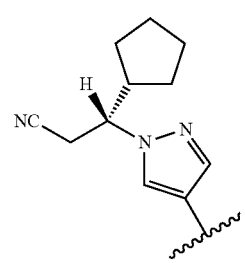

(1)

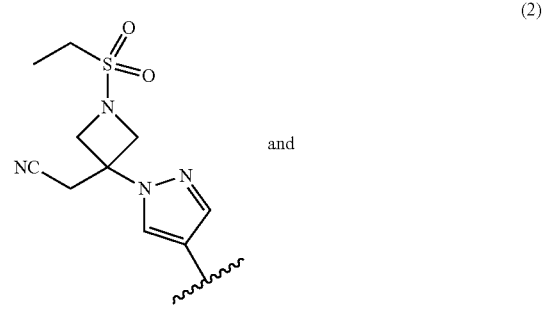

(2)

and (3)

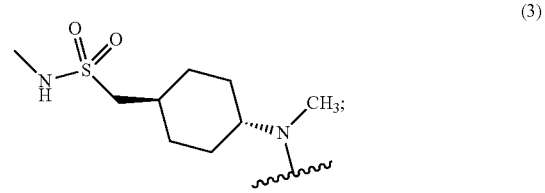

and $A^1$ is a group having the formula (iv)

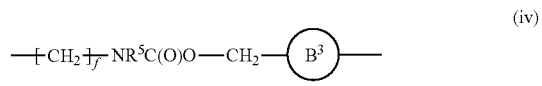

(iv)

wherein f is 2 or 3; $R^5$ is hydrogen or $C_{1-3}$alkyl; and $B^3$ is selected from $C_{6-10}$aryl and $C_{1-9}$heteroaryl; wherein the heteroaryl group contains from 1 to 4 heteroatoms selected from nitrogen, oxygen and sulfur; the aryl or heteroaryl group is unsubstituted or substituted with 1 to 3 substituents independently selected from $C_{1-4}$alkyl, $C_{1-3}$alkoxy, amino, cyano, halo, hydroxy, nitro and trifluoromethyl;

or a pharmaceutically-acceptable salt thereof.

2. The compound of claim 1, wherein $W^1$ has formula (1).
3. The compound of claim 1, wherein $W^1$ has formula (2).
4. The compound of claim 1, wherein $W^1$ has formula (3).
5. The compound of claim 1 having the formula VI:

VI

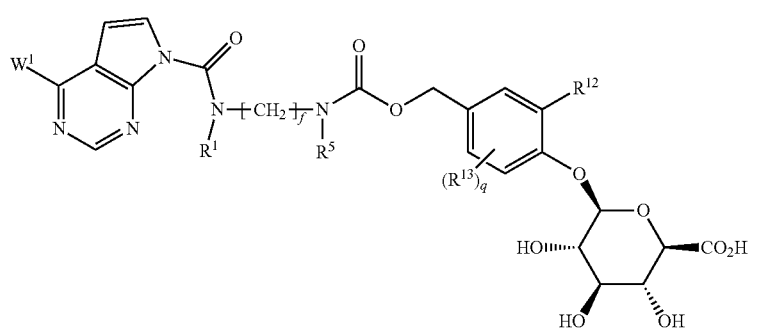

wherein
f is 2 or 3;
q is 0, 1 or 2;
$R^1$ is hydrogen or $C_{1-3}$alkyl;
$R^5$ is hydrogen or $C_{1-3}$alkyl;
$R^{12}$ is hydrogen, $C_{1-4}$alkyl, $C_{1-3}$alkoxy, amino, cyano, halo, hydroxy, nitro or trifluoromethyl;
each $R^{13}$, when present, is independently selected from $C_{1-4}$alkyl, $C_{1-3}$alkoxy, amino, cyano, halo, hydroxyl, nitro and trifluoromethyl; and
$W^1$ is selected from:

or a pharmaceutically-acceptable salt thereof.
6. The compound of claim 5, wherein $W^1$ has formula (1).
7. The compound of claim 5, wherein $W^1$ has formula (2).
8. The compound of claim 5, wherein $W^1$ has formula (3).
9. The compound of claim 5, wherein $R^1$ is methyl.
10. The compound of claim 5, wherein f is 2.
11. The compound of claim 5, wherein $R^5$ is methyl.
12. The compound of claim 5, wherein q is 0.
13. The compound of claim 5, wherein $R^{12}$ is hydrogen, $C_{1-4}$alkyl, halo, nitro or trifluoromethyl.
14. The compound of claim 5, wherein f is 2; q is 0; $R^1$ is methyl; $R^5$ is methyl; and $R^{12}$ is hydrogen, $C_{1-4}$alkyl, halo, nitro or trifluoromethyl.
15. The compound of claim 1 having the formula VII:

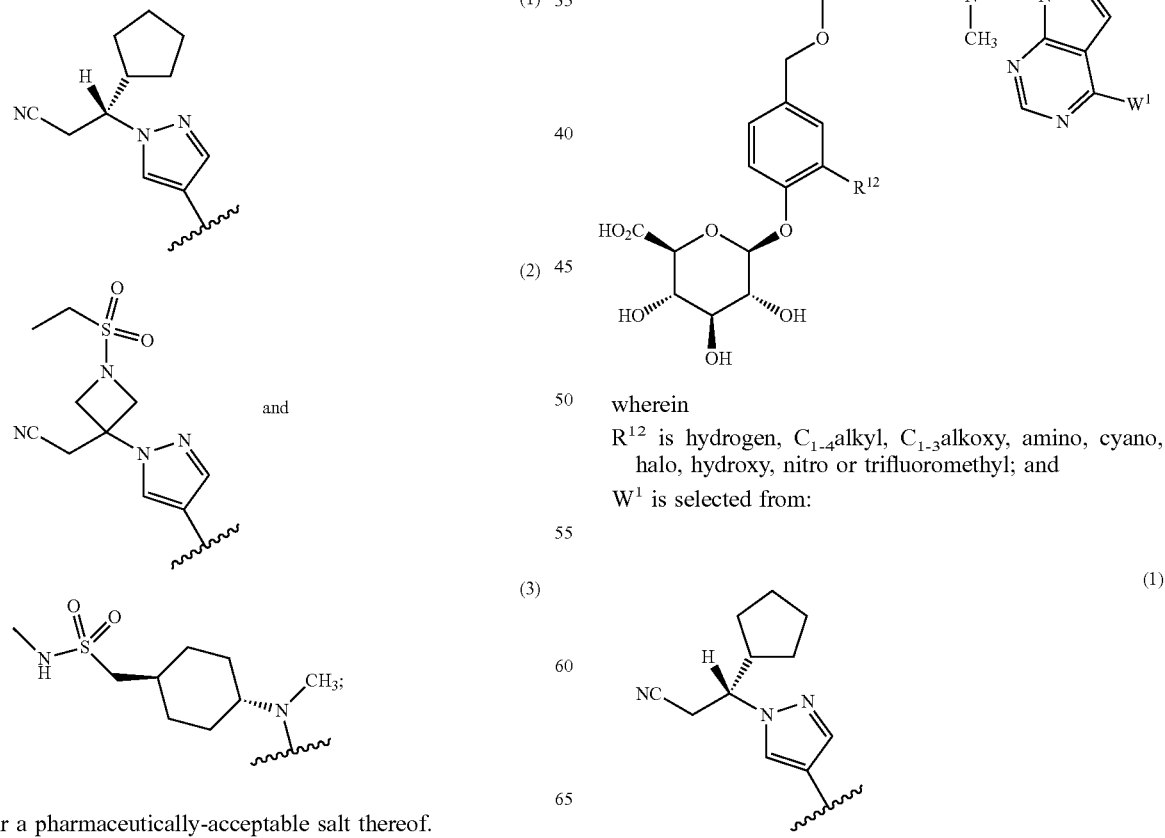

wherein
$R^{12}$ is hydrogen, $C_{1-4}$alkyl, $C_{1-3}$alkoxy, amino, cyano, halo, hydroxy, nitro or trifluoromethyl; and
$W^1$ is selected from:

-continued (2)

[Structure: azetidine with ethylsulfonyl group, CH2CN substituent, and pyrazole]

and (3)

[Structure: N-methylsulfamoylmethyl cyclohexyl with N-methylamine]

or a pharmaceutically-acceptable salt thereof.

16. The compound of claim 15, wherein $W^1$ has formula (1).

17. The compound of claim 15, wherein $W^1$ has formula (2).

18. The compound of claim 15, wherein $W^1$ has formula (3).

19. The compound of claim 15, where $R^{12}$ is hydrogen.

20. The compound of claim 15, where $R^{12}$ is nitro.

21. A pharmaceutical composition comprising a pharmaceutically acceptable-carrier and a compound of claim 1.

22. A method of treating a gastrointestinal inflammatory disease selected from the group consisting of ulcerative colitis, Crohn's disease and colitis associated with immune checkpoint inhibitor therapy, in a mammal, the method comprising administering to the mammal a pharmaceutical composition comprising a pharmaceutically acceptable-carrier and a compound of claim 1.

23. The method of claim 22, wherein the gastrointestinal inflammatory disease is ulcerative colitis.

24. The method of claim 22, wherein the gastrointestinal inflammatory disease is Crohn's disease.

25. The method of claim 22, wherein the gastrointestinal inflammatory disease is colitis associated with immune checkpoint inhibitor therapy.

26. A process for preparing a compound of claim 1, the process comprising deprotecting a compound of formula 3:

3

[Structure of formula 3]

wherein
$R^1$, $W^1$ and $A^1$ are as defined in claim 1;
$P^1$ is a carboxy-protecting group; and
each $P^2$ is independently a hydroxyl-protecting group;
or a salt thereof;
to provide a compound of claim 1.

27. A process for preparing a compound of claim 1, the process comprising:
(a) contacting a compound of formula 1:

1

[Structure of formula 1]

wherein
$W^1$ is as defined in claim 1;
$L^1$ is an acyl leaving group;
or a salt thereof;
with a compound of formula 2:

2

[Structure of formula 2]

wherein
$R^1$ and $A^1$ are as defined in claim 1;
$P^1$ is a carboxy-protecting group; and
each $P^2$ is independently a hydroxyl-protecting group;
or a salt thereof;
to provide a compound of formula 3:

3

[Structure of formula 3]

or a salt thereof; and
(b) deprotecting the compound of formula 3, or a salt thereof, to provide a compound of claim 1.

28. A process for preparing a compound of claim 1, the process comprising:
(a) contacting a compound of formula 4:

4

[Structure of formula 4]

wherein $W^1$ is as defined in claim 1;
or a salt thereof;

with a compound of formula 5:

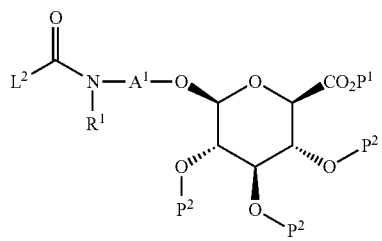

wherein
R¹ and A¹ are as defined in claim 1;
L² is an acyl leaving group;
P¹ is a carboxy-protecting group; and
each P² is independently a hydroxyl-protecting group;
or a salt thereof;

to provide a compound of formula 3:

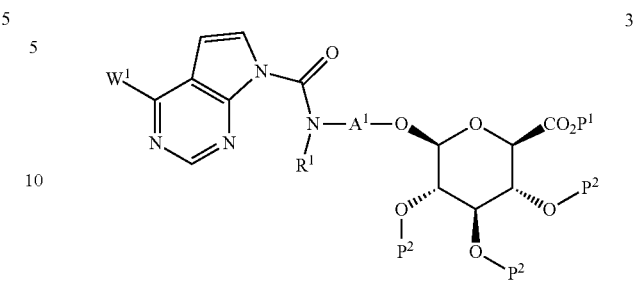

or a salt thereof, and (b) deprotecting the compound of formula 3, or a salt thereof, to provide a compound of claim 1.

29. A compound of formula VII-1:

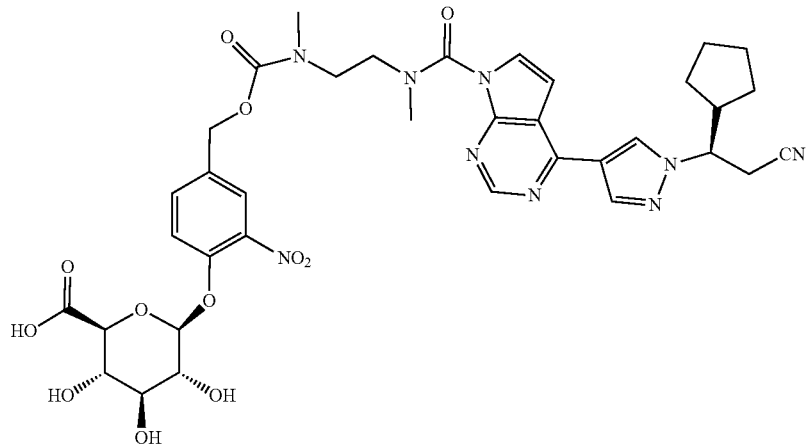

or a pharmaceutically acceptable salt thereof.

30. The compound of claim 1, wherein the compound has the formula VII-2:

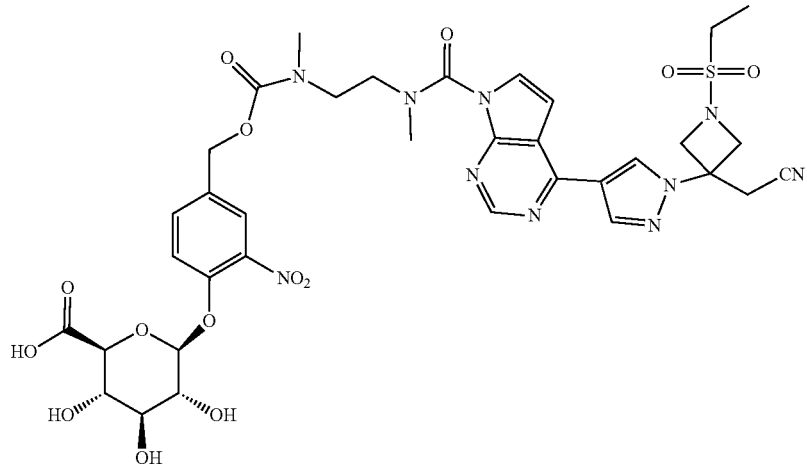

or a pharmaceutically acceptable salt thereof.

31. The compound of claim 1, wherein the compound has the formula VII-3:
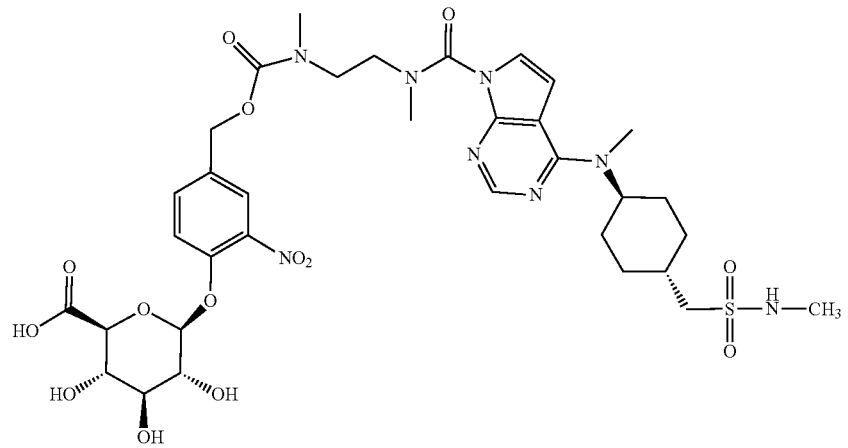
VII-3
or a pharmaceutically acceptable salt thereof.
* * * * *